US011890286B2

(12) United States Patent
Yesilkanal et al.

(10) Patent No.: US 11,890,286 B2
(45) Date of Patent: Feb. 6, 2024

(54) METHODS AND COMPOSITIONS FOR TREATING CANCER

(71) Applicant: THE UNIVERSITY OF CHICAGO, Chicago, IL (US)

(72) Inventors: Ali Ekram Yesilkanal, Chicago, IL (US); Marsha Rosner, Chicago, IL (US)

(73) Assignee: The University of Chicago, Chicago, IL (US)

( * ) Notice: Subject to any disclaimer, the term of this patent is extended or adjusted under 35 U.S.C. 154(b) by 212 days.

(21) Appl. No.: 17/048,282

(22) PCT Filed: Apr. 17, 2019

(86) PCT No.: PCT/US2019/027817
§ 371 (c)(1),
(2) Date: Oct. 16, 2020

(87) PCT Pub. No.: WO2019/204399
PCT Pub. Date: Oct. 24, 2019

(65) Prior Publication Data
US 2021/0100803 A1 Apr. 8, 2021

Related U.S. Application Data

(60) Provisional application No. 62/658,804, filed on Apr. 17, 2018.

(51) Int. Cl.
A61K 31/519 (2006.01)
A61P 35/04 (2006.01)
A61K 31/416 (2006.01)
A61K 31/4178 (2006.01)
A61K 31/437 (2006.01)
A61K 45/06 (2006.01)

(52) U.S. Cl.
CPC .......... *A61K 31/519* (2013.01); *A61K 31/416* (2013.01); *A61K 31/4178* (2013.01); *A61K 31/437* (2013.01); *A61P 35/04* (2018.01); *A61K 45/06* (2013.01)

(58) Field of Classification Search
CPC ................ A61K 31/437; A61K 31/519; A61K 31/5377; A61K 31/5383
See application file for complete search history.

(56) References Cited

U.S. PATENT DOCUMENTS 6,864,224 B1 * 3/2005 Sedivy ................. G01N 33/566
435/375
2011/0256150 A1 10/2011 Watts et al.
2017/0202842 A1 * 7/2017 Laquerre ............. A61K 31/506
2018/0065938 A1 3/2018 Chin et al.

FOREIGN PATENT DOCUMENTS

WO WO-2008123867 A1 * 10/2008 ........... C12Q 1/6886
WO WO-2015161230 A1 * 10/2015 ........... A61K 31/381

OTHER PUBLICATIONS

Magliozzi (Developmental Cell vol. 27 pp. 574-585 published 2013). (Year: 2013).*
Ju (Molecular Cancer Research vol. 15 pp. 723-734 published 2017). (Year: 2017).*
Kobayashi (Cellular Signaling vol. 26 pp. 1082-1088 published 2014). (Year: 2014).*
Kalendar (Oncology Research vol. 18 pp. 583-591 published 2010). (Year: 2010).*
Corcoran (Journal of Clinical Oncology vol. 33 pp. 4023-4031 published 2015). (Year: 2015).*
Lin (Experimental Cellular Research vol. 317 pp. 2031-3040 published 2011) (Year: 2011).*
Rhoo (PLOS One vol. 9 Issue 9 published Sep. 2014) (Year: 2014).*
Ludwik (Molecular Cancer Therapeutics vol. 15 pp. 2598-2608 published 2016) (Year: 2016).*
The International Search Report of the International Searching Authority (US) for International Application No. PCT/US2019/027817; dated Jul. 22, 2019, pp. 1-4.
Goodfellow et al., "Discovery, synthesis, and characterization of an orally bioavailable, brain penetrant inhibitor of mixed lineage kinase 3," Journal of Medicinal Chemistry, 456(20):8032-48 (Oct. 2013).

* cited by examiner

Primary Examiner — Theodore R. Howell
Assistant Examiner — George W Kosturko
(74) Attorney, Agent, or Firm — McDonnell Boehnen Hulbert & Berghoff LLP

(57) ABSTRACT

Methods and compositions for treating cancer are disclosed.

7 Claims, 78 Drawing Sheets
Specification includes a Sequence Listing.

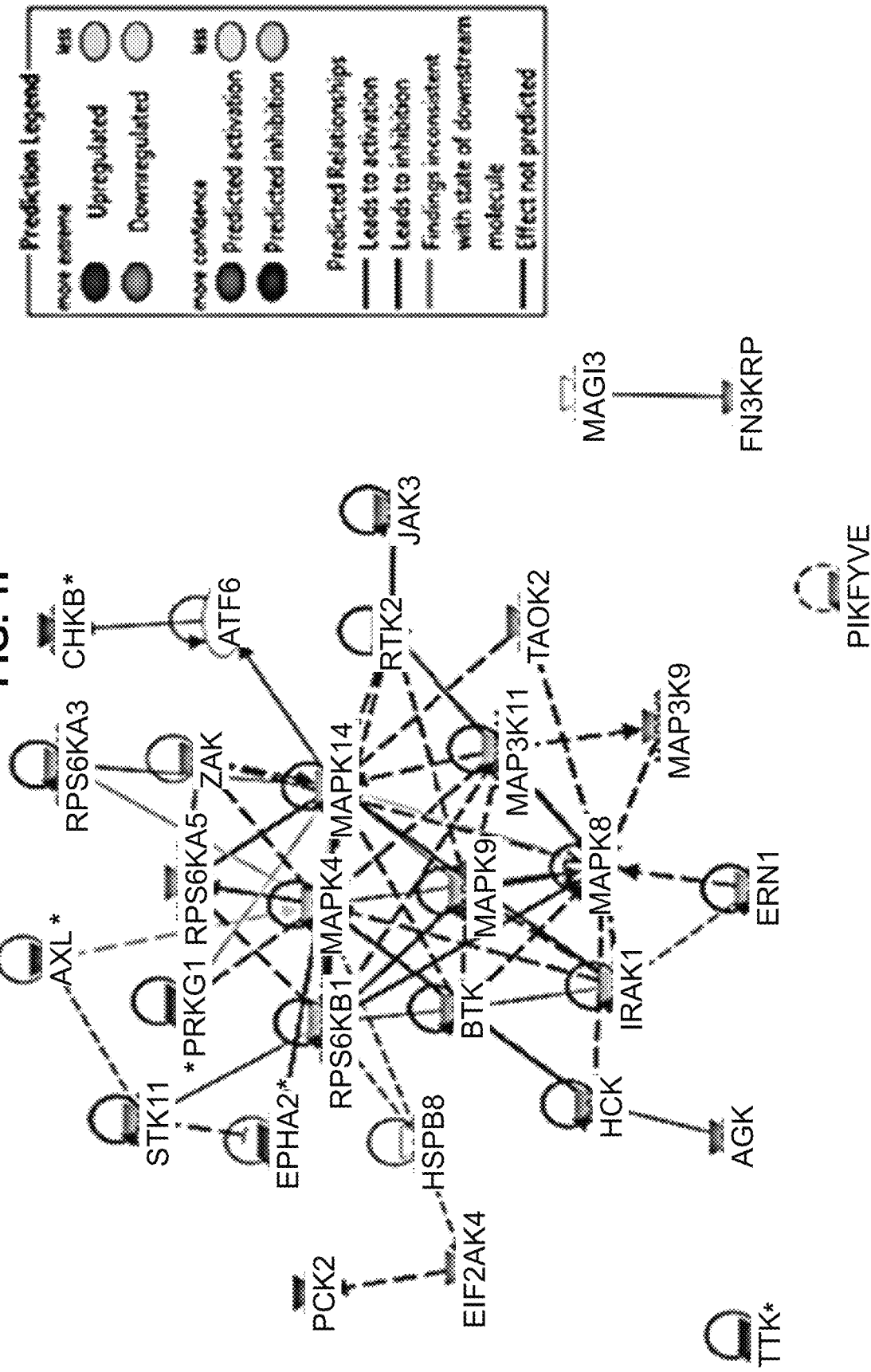

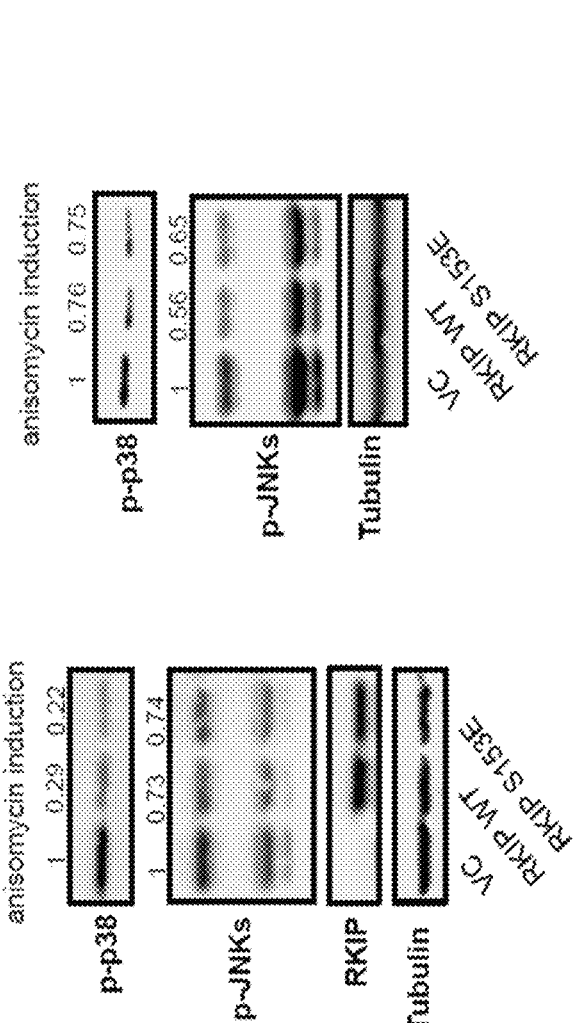
FIG. 2A
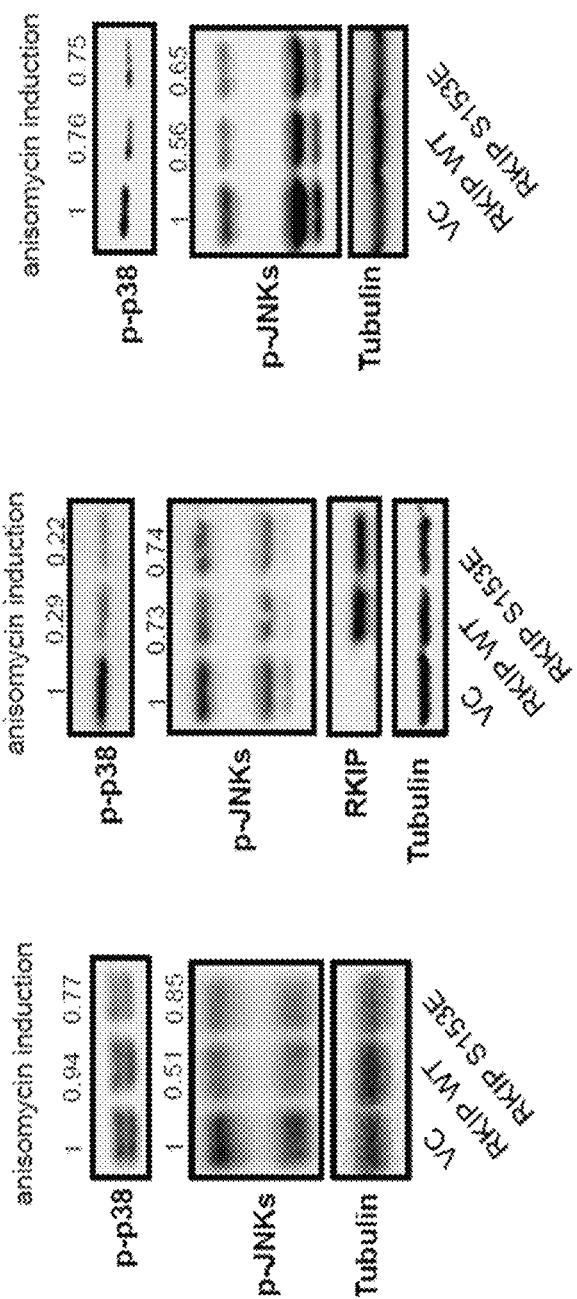
FIG. 2B
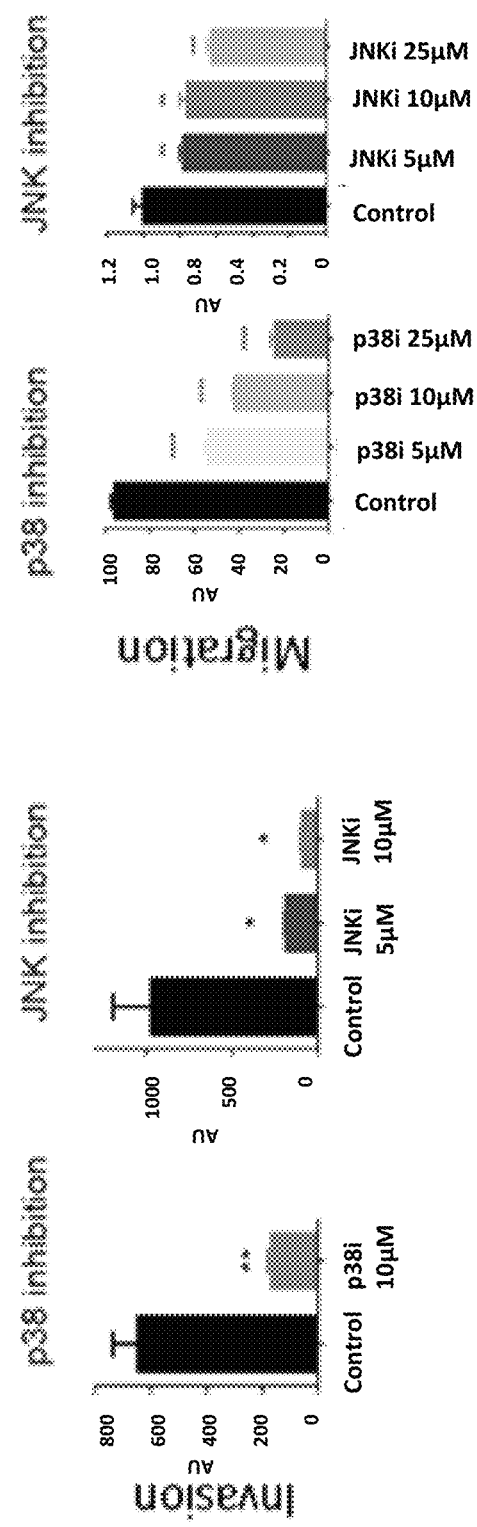

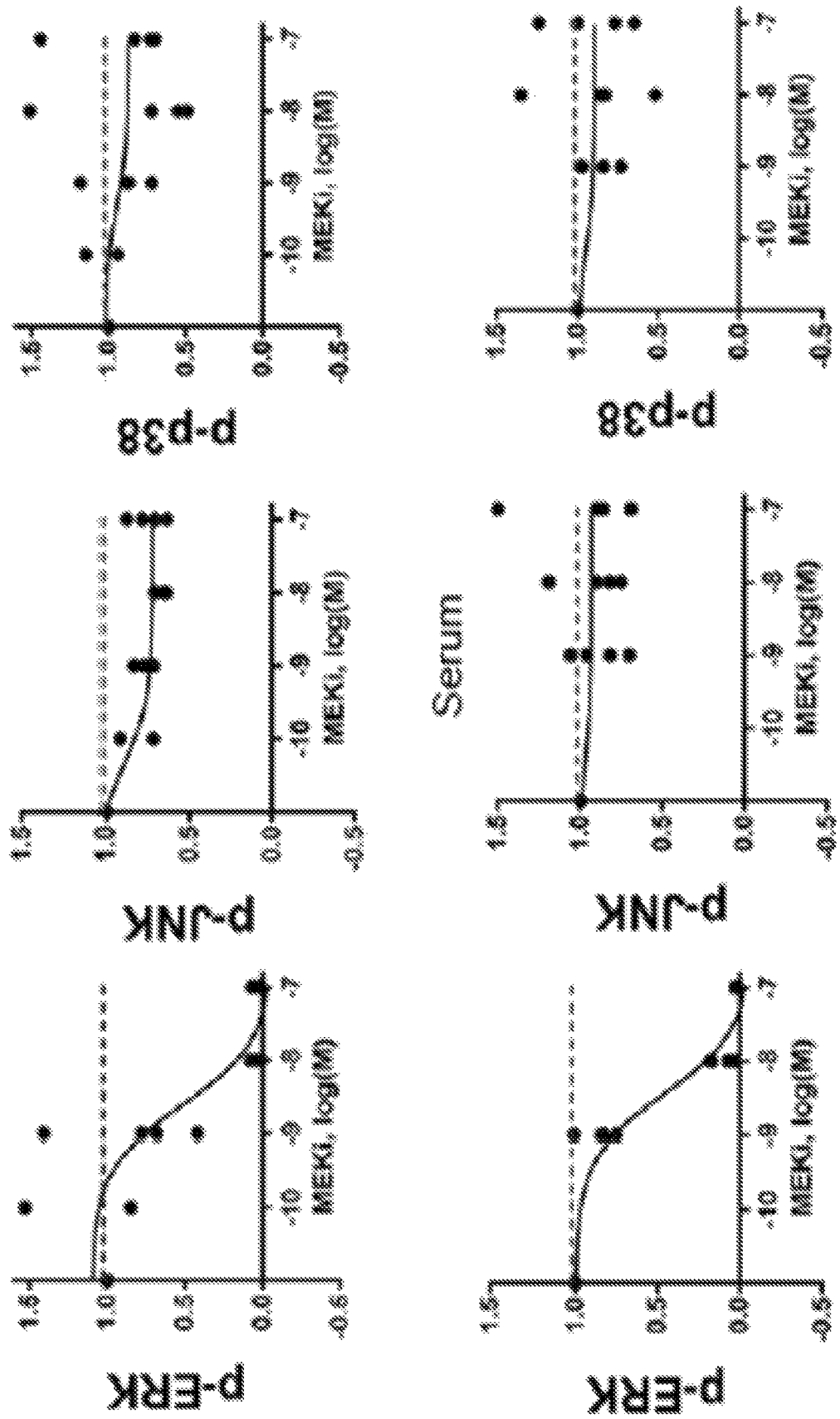

MB436 cells

LMB cells

M6C cells

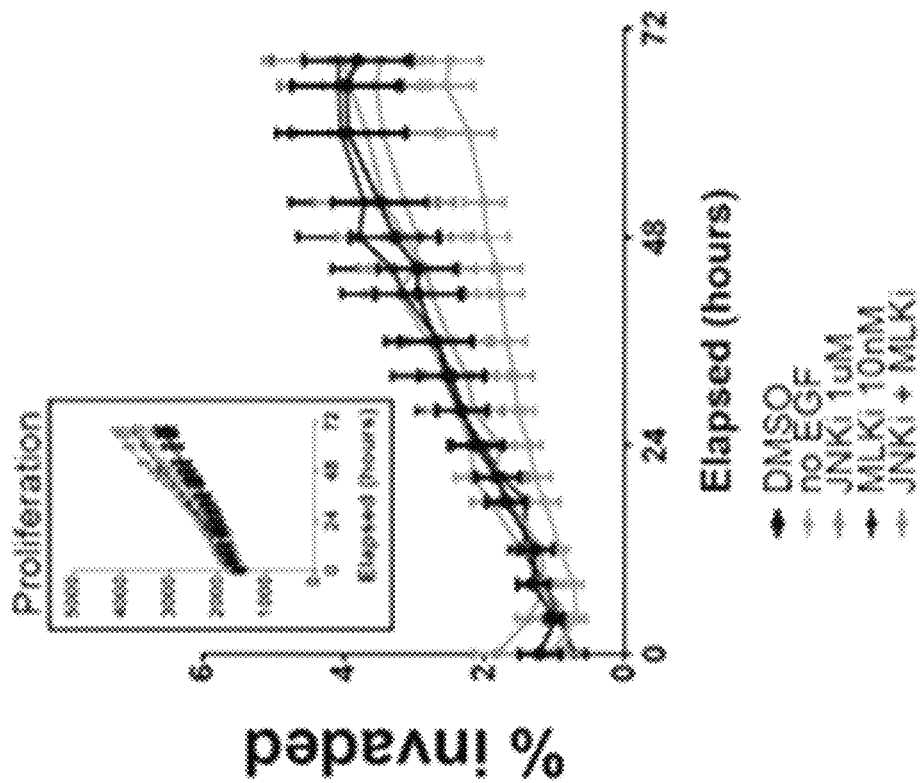
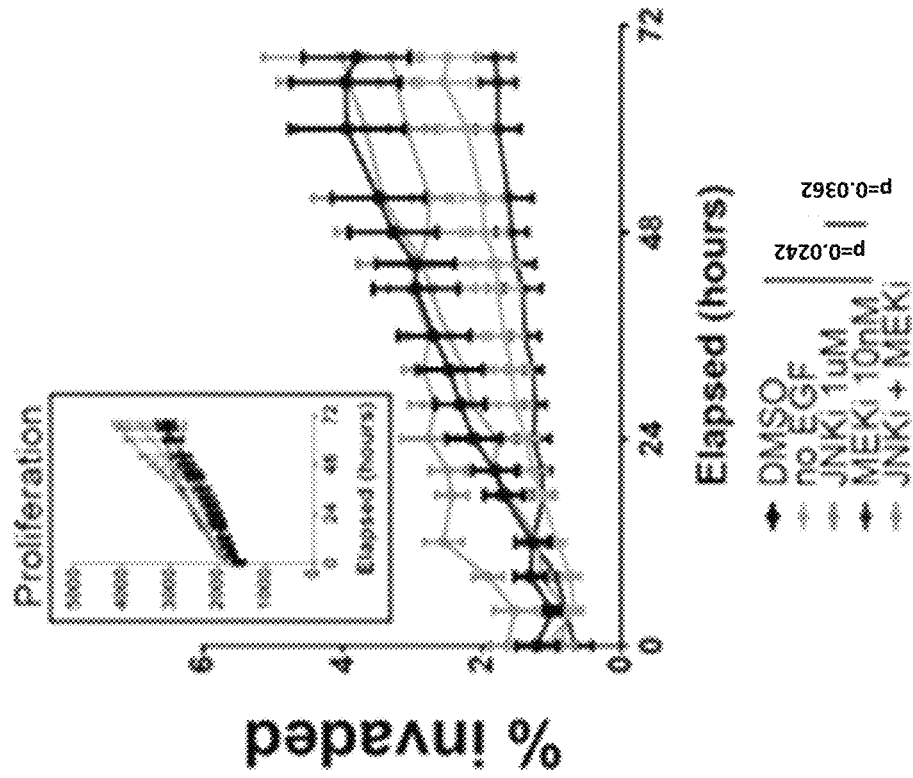
FIG. 7B - continued

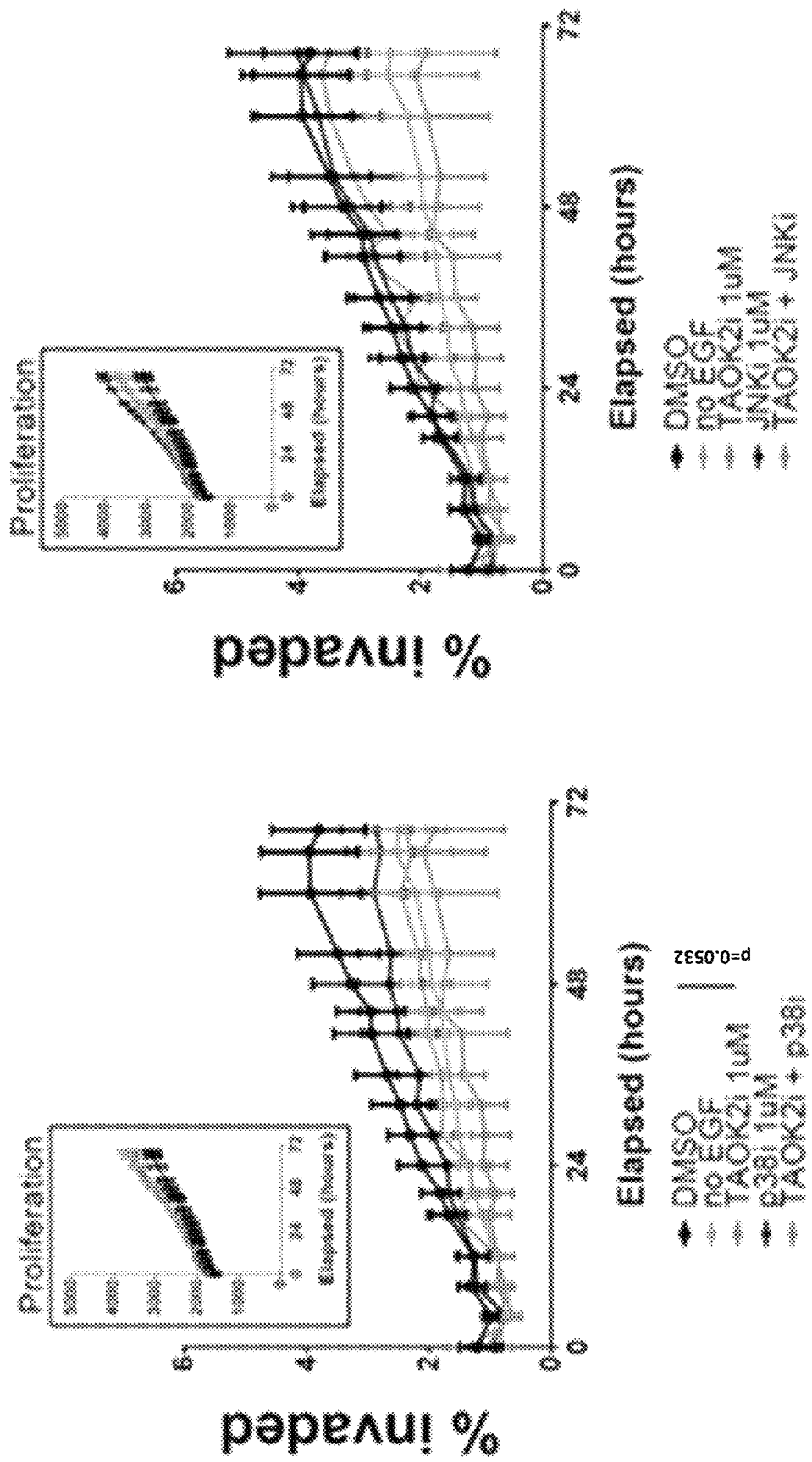
FIG. 7B - continued

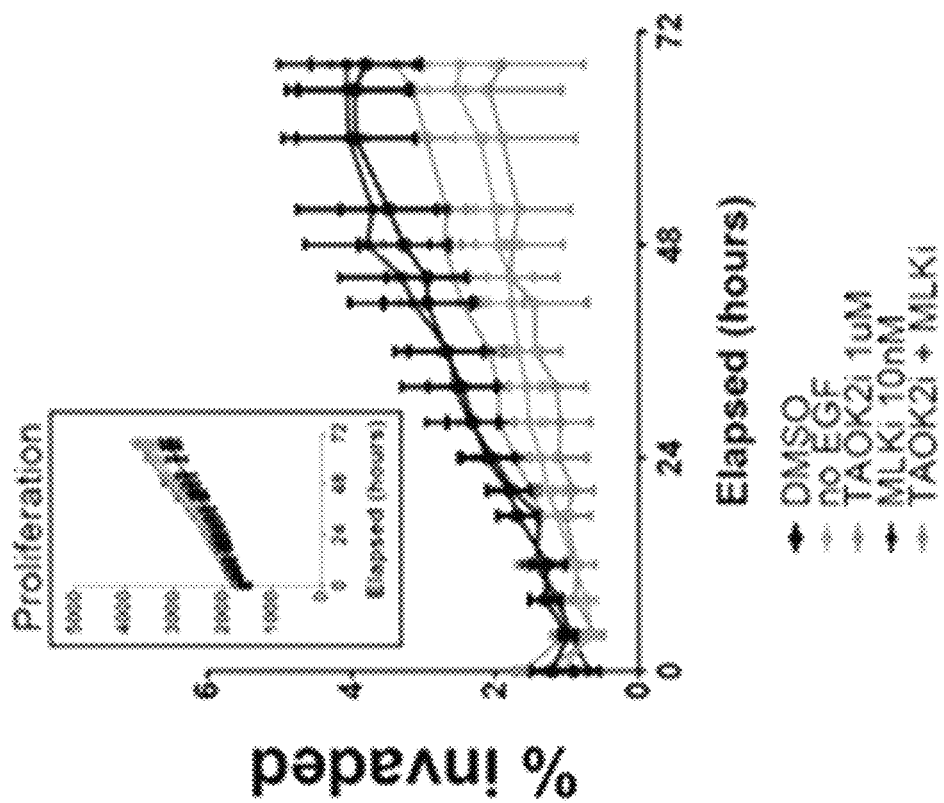
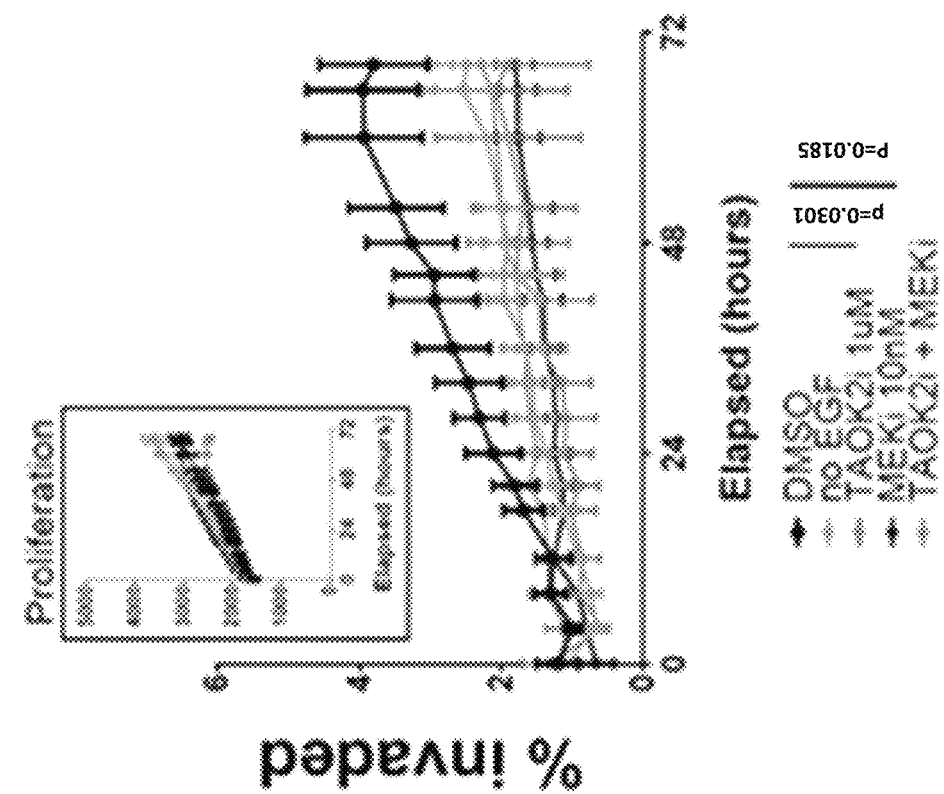
FIG. 7B - continued

FIG. 11C

| Gene | FC(log2) | P | S | JUN | ATF | MYC | BACH1 |
|---|---|---|---|---|---|---|---|
| ROCK1 | -0.51 | -0.43 | -0.46 | Yes | No | Yes | Yes |
| ROCK2 | -0.81 | -0.34 | -0.42 | Yes | Yes | Yes | No |
| ADAM10 | -0.71 | -0.39 | -0.42 | Yes | Yes | Yes | No |
| ADAM17 | -0.52 | -0.34 | -0.45 | Yes | Yes | Yes | Yes |
| EPC1 | -0.59 | -0.31 | -0.31 | Yes | Yes | Yes | No |
| PIKFYVE | -0.50 | -0.39 | -0.42 | Yes | Yes | Yes | Yes |
| DOCK4 | -0.48 | -0.36 | -0.44 | Yes | Yes | Yes | Yes |
| DOCK5 | -0.39 | -0.35 | -0.42 | Yes | Yes | Yes | Yes |
| ARL13B | -0.46 | -0.30 | -0.32 | Yes | Yes | Yes | No |
| DDR2 | -0.45 | -0.37 | -0.50 | Yes | Yes | Yes | No |
| ITGA1 | -0.41 | -0.31 | -0.36 | Yes | No | Yes | Yes |
| RAPGEF2 | -0.35 | -0.35 | -0.42 | Yes | Yes | Yes | Yes |
| RAPGEF6 | -0.39 | -0.31 | -0.36 | Yes | Yes | Yes | Yes |
| NFATC2 | -0.85 | -0.31 | -0.42 | Yes | Yes | Yes | Yes |
| APC | -0.33 | -0.32 | -0.34 | Yes | Yes | Yes | No |

FIG. 11D - continued
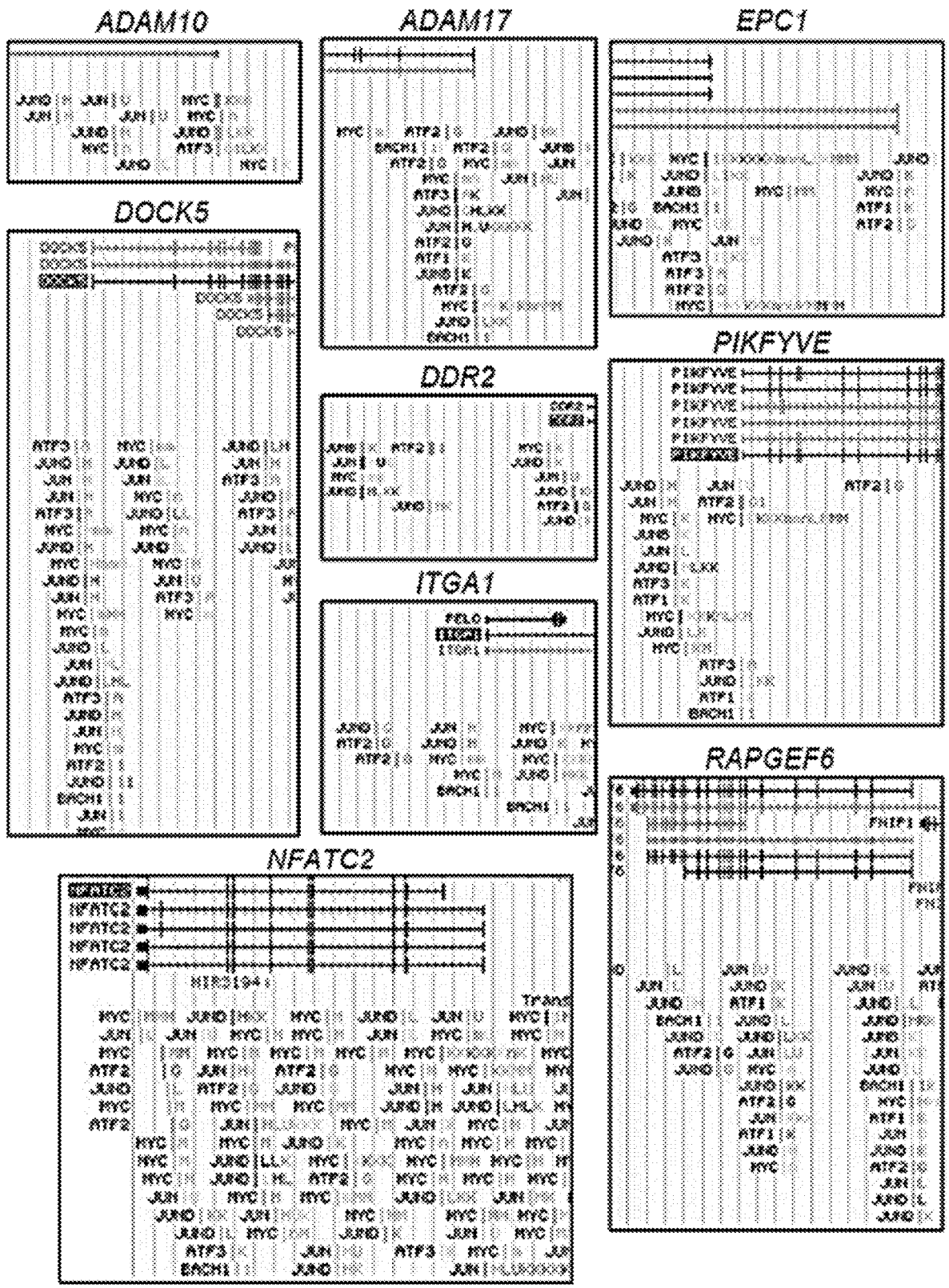

FIG. 11D - continued

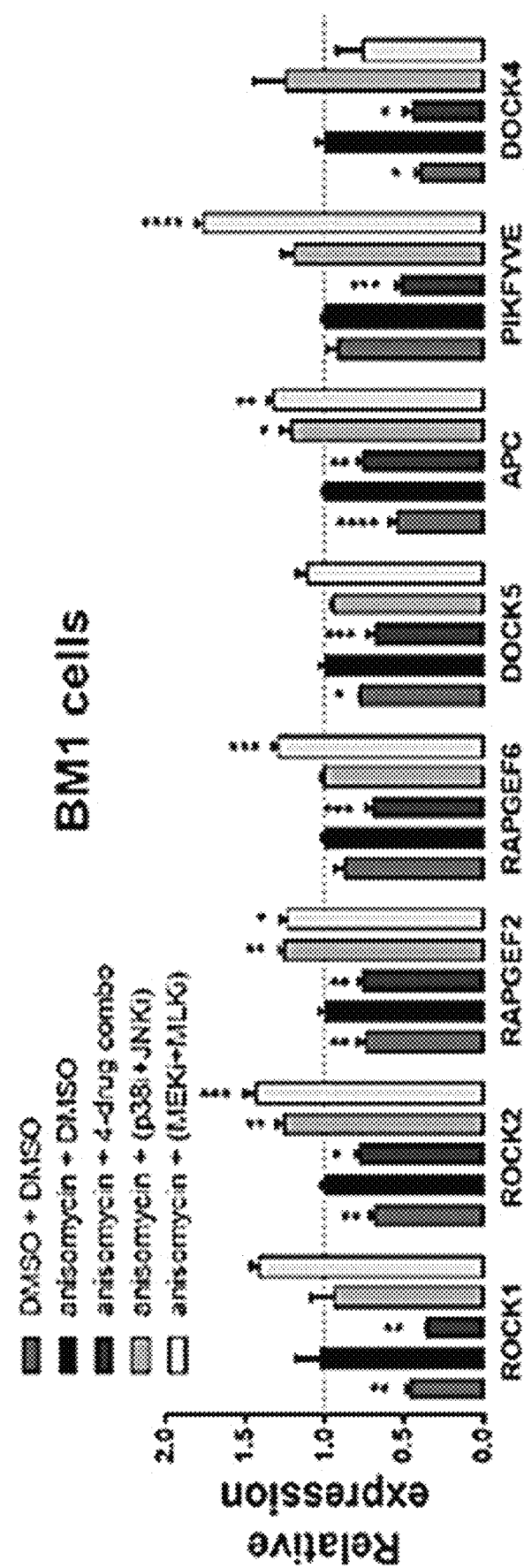

FIG. 12A xenograft
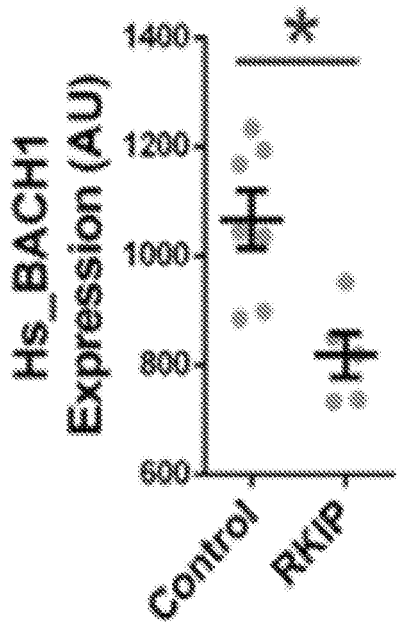
FIG. 12B syngeneic
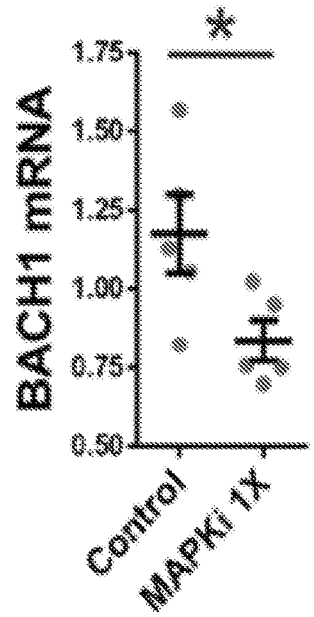
FIG. 12C
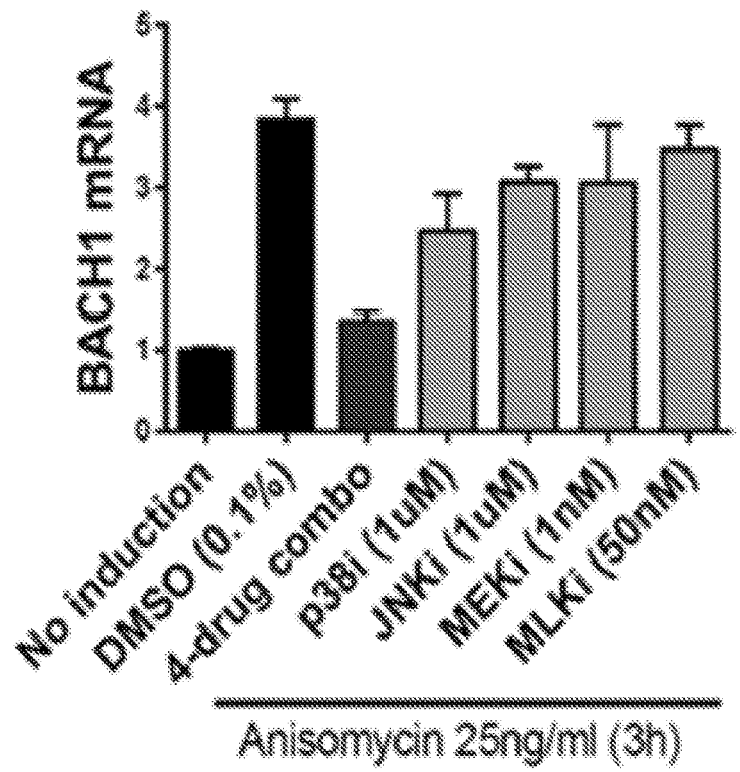

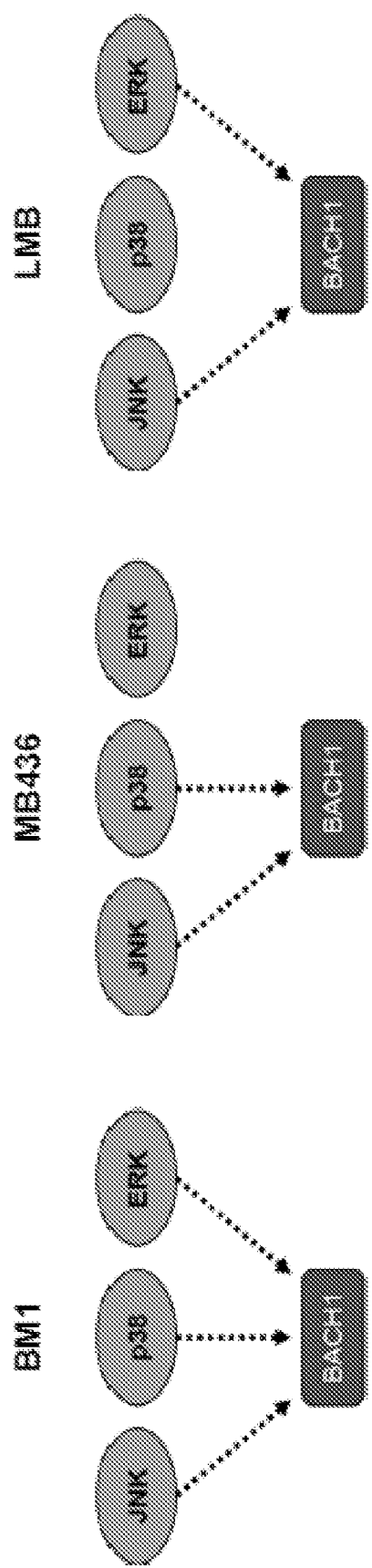

LMB tumors

SEQUENCE LISTING

<160> NUMBER OF SEQ ID NOS: 76

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 1
gctctacacc ttggtcctga ca                22

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
aatcggagag gactgtgcca ct                                             22

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
gatagtgggc aacaccaaag tcc                                            23

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
tctcgccttt ccgcagctca at                                             22

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
gaaacagtgt tccatgctag acg                                            23

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
gccgcttatt tgattcctgc tcc                                            23

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
tgcggtcaca actccaagcc tt                                             22

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 8
cgtacaggca atgaaagcca tcc                                              23

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
gaggagtgta cgtgtgccag tt                                               22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
gaccactgaa gtgcctactc ca                                               22

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
aacagcgact gcacgttgaa gg                                               22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
ctgtgcagta ggacacgcct tt                                               22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13
ccagacatgc agtacctcta cg                                               22

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
gctgtttctg catgagtgcc ag                                               22

<210> SEQ ID NO 15
```

-continued

```
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 15
ctgagtgatg ctgtgtggtc aac                                              23

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
caaggactga cacaggcact ag                                               22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
gcatgtggat gattccctgc ag                                               22

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 18
ggaggtgatg taacacgaca gg                                               22

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 19
gcttctgagc aacatcctgg ag                                               22

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 20
tccttctcag cagccgttcc at                                               22

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
```

```
gaaccagtgg tctggctgag tt                                              22

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
gtttcaggtg gcagccatca ct                                              22

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 23
aacgagagtg ccaccaatgg ct                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 24
actcactggc ttcagagcgg aa                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
ccgaagaggt acttgttgca gc                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 26
ggcttccgtg aatgcctcct tt                                              22

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 27
ctcggatcag tatcttgcca cag                                             23

<210> SEQ ID NO 28
<211> LENGTH: 22
<212> TYPE: DNA
```

```
<213> ORGANISM: Artificial Sequence
<220> FEATURE:
<223> OTHER INFORMATION: Synthetic oligonucleotide

<400> SEQUENCE: 28
aggttccact gacaggcaat gc                                              22

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 29
agacagatga ggagaagttc cag                                             23

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30
gacctcatag gcactggaga ca                                              22

<210> SEQ ID NO 31
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 31
aggctgcatg agagcacttg tg                                              22

<210> SEQ ID NO 32
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 32
cacacttcca acttctcgca acg                                             23

<210> SEQ ID NO 33
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 33
actctacacc ctggtcctca ca                                              22

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 34
tgagaggaca gtgccactgc ta                                              22
```

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
acttcacagc ggagtccaag gt                                          22

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 36
ggatgtgctt gttccgatac tcg                                         23

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 37
cacgcctaac tgacaagcac ca                                          22

<210> SEQ ID NO 38
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 38
caggtcaaca tctagcatgg aac                                         23

<210> SEQ ID NO 39
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 39
gtgacctcaa acagtctcag cag                                         23

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
gacaacgctt ctgagtttcc tgc                                         23

<210> SEQ ID NO 41
<211> LENGTH: 22
<212> TYPE: DNA
<213> ORGANISM: Artificial Sequence
<220> FEATURE:

<223> OTHER INFORMATION: Synthetic oligonucleotide

<400> SEQUENCE: 41
tgcacctgtg ccagctctga tg                                              22

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 42
gatagtccga ccactgaact gc                                              22

<210> SEQ ID NO 43
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 43
tgtgagcggt gaccacgaga at                                              22

<210> SEQ ID NO 44
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 44
ttcatccacc ctggagttgc ca                                              22

<210> SEQ ID NO 45
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 45
ctgccaggct tcagtgctaa ag                                              22

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 46
actgacagcc tgctttccta cg                                              22

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 47
tcttctgccc agtccagcaa tg                                              22

```
<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 48
acagaacatg ctcggacact gg                                              22

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 49
gataggagag gtggatggca ag                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 50
cgccttgaga tgcagatcgt ag                                              22

<210> SEQ ID NO 51
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 51
gagccgacag tctcctcaca tt                                              22

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 52
ctgcctggtt ttgaaggtgc tg                                              22

<210> SEQ ID NO 53
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 53
accagtggtc tggctgagat tg                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 54
catcactgtc cttctccacg gt                                              22

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 55
tcatcctgtg gaggcagttc tg                                              22

<210> SEQ ID NO 56
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 56
ctgttcactt ggtgatgagg agc                                             23

<210> SEQ ID NO 57
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 57
ggcagtggca agaccataag ga                                              22

<210> SEQ ID NO 58
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 58
catctctccg tggatagact gg                                              22

<210> SEQ ID NO 59
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 59
gccgaatggc atcagtcaac atg                                             23

<210> SEQ ID NO 60
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 60
caacatccag cactgtggcg tt                                              22

<210> SEQ ID NO 61
<211> LENGTH: 22
```

```
<212> TYPE: DNA
<213> ORGANISM: Artificial Sequence
<220> FEATURE:
<223> OTHER INFORMATION: Synthetic oligonucleotide

<400> SEQUENCE: 61
acagagtgag ccaggtgctt ca                                            22

<210> SEQ ID NO 62
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 62
cactcacttc ctcagttggt cc                                            22

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63
gtggactgtg agatgtatgg gc                                            22

<210> SEQ ID NO 64
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 64
cacaagtgct ctcatgcagc ct                                            22

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
cagcctcact ctcccatttt                                               20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
tccagccttt cctctgctaa                                               20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 67
```
ctggactcct tctgcctgag                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
aagactccgc cctctgtttt                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
atttgcctgg agtggaagtg                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
ctgtatccag ggggatgatg                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
taagccctag ctcctggaca                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
aggggtcaca aacactcctg                                              20

<210> SEQ ID NO 73
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 73
aaaaatgcca agaagggtt a                                             21

<210> SEQ ID NO 74
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 74
cactcatcta gacagacccc tga                                              23

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 75
cgccacagtt cattcacact                                                  20

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 76
gcgaagggtt gtttgctaga                                                  20
```

METHODS AND COMPOSITIONS FOR TREATING CANCER

PRIORITY

This application is a U.S. national stage application under 35 U.S.C. 371 of International Application No. PCT/US2019/027817, filed on Apr. 17, 2019, which claims the benefit of U.S. provisional application Ser. No. 62/658,804, filed Apr. 17, 2018, each of which is incorporated by reference herein in its entirety.

STATEMENT REGARDING FEDERALLY SPONSORED RESEARCH OR DEVELOPMENT

This invention was made with government support under GM087630 and GM121735 awarded by the National Institutes of Health. The government has certain rights in the invention.

BACKGROUND OF THE INVENTION

Field of the Invention

This disclosure relates to compositions and methods for treating cancer, and triple-negative breast cancer in particular.

Metastasis remains the deadliest aspect of cancer. Despite advancements in treating early-stage cancers, the therapeutic options for late-stage disease are limited. Recent studies suggest that targeting metastatic mechanisms can increase response to chemotherapy and improve survival even in tumors with established metastatic burden. (Odabaei et al., 2004; Steeg, 2016). Therefore, understanding molecular and cellular mechanisms that drive the spread of tumor cells to distant organs is essential to deriving treatment combinations that block metastatic cancer progression, particularly for cancers that lack effective targeted therapy, for example, triple negative breast cancer (ER-, PR-, HER2low; TNBC) (Al-Mahmood et al., 2018). Mimicking RKIP with therapeutic agents is a promising treatment strategy. However, single drug therapies that target key genes such as Raf in cancer have been largely unsuccessful (Karoulia et al., 2017). Effective combination therapy based on RKIP action is not possible at present since the RKIP regulatory network is complex and not well-defined. To really exploit this physiological anti-metastatic protein, it is important to identify the metastatic drivers targeted by RKIP in tumors. As metastasis remains the deadliest aspect of cancer, effective anti-metastatic therapies for cancer patients are needed.

SUMMARY OF THE INVENTION

This disclosure investigated the RKIP-regulated kinome in TNBC tumors with the goal of discovering essential metastatic signaling networks that can be targeted using kinase inhibitor combinations. Kinases regulated by RKIP in the MAPK network were identified and investigated in TNBC cells and showed that partially inhibiting 4 discrete nodes with a unique 4-drug MAPK inhibitor (4D-MAPKi) combination was effective at suppressing tumor invasion and metastasis as well as enhancing survival. RNA sequencing analysis of xenograft TNBCs expressing RKIP identified genes that mediate cell motility/adhesion and are similarly inhibited by the 4D-MAPKi. Finally, genes negatively regulated by RKIP in preclinical models corresponded to genes whose expression inversely correlates with RKIP expression across breast and other cancer types in TCGA patient data sets. These studies in this disclosure support the strategy of partially inhibiting multiple nodes within a critical kinase network to slow or prevent invasion and metastasis of cancer and highlight the potential clinical relevance of this signaling network. In particular, any combination of MAPK inhibitors that can inhibit multiple MAPK axes (for example, p38, JNK, and ERK) simultaneously can be an effective treatment in preventing invasion and metastasis of cancer.

In a first aspect, the invention provides a composition, comprising a combination of drugs comprising at least two or more inhibitors of the mitogen-activated protein kinase (MAPK) pathway, wherein the at least two or more inhibitors are selected from inhibitors of MEK1, MEK2, p38MAPK, JNK1, JNK2, JNK3, MLK 1, MLK2, MLK3, TAOK1, TAOK2, DLK, MAP2K4, MAP3K1, MAP3K2, MAP3K3, MAP3K4, MAP3K5, MAP3K6, MAP3K7, MAP3K8, MAP3K12, MAP3K13, MAP3K14, MAP3K15, MAP3K20, RAF1, BRAF, and ARAF. In some embodiments, each of the at least two or more inhibitors is present in a low-dose. In an embodiment of the composition, the at least two or more inhibitors comprise (a) a MEK inhibitor, (b) a p38MAPK inhibitor, (c) a JNK inhibitor, and (d) a MLK inhibitor.

In certain embodiments of the first aspect, the MEK inhibitor is selected from the group consisting of trametinib (Mekinist™), cobimetinib (Cotellic™), binimetinib (MEK162, ARRY-162), selumetinib (AZD6244), pimasertib (AS-703026), refametinib (RDEA119, Bay 86-9766), PD-325901, PD-035901, PD-184352 (CI-1040), TAK-733, U0126-EtOH, and BI-847325. In an embodiment, the MEK inhibitor is trametinib (Mekinist™), and the low-dose of trametinib (Mekinist™) in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, the p38MAPK inhibitor is selected from the group consisting of SB203580, doramapimod (BIRB 796), SB202190 (FHPI), ralimetinib (LY2228820), VX-702, PH-797804, VX-745, TAK-715, pamapimod (R-1503, Ro4402257), BMS-582949, SB239063, losmapimod (GW856553X), skepinone-L, and pexmetinib (ARRY-614). In an embodiment, the p38MAPK inhibitor is SB203580 (4-(4-Fluorophenyl)-2-(4-methylsulfinylphenyl)-5-(4-pyridyl)-1H-imidazole), and the low-dose of SB203580 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, the JNK inhibitor is selected from the group consisting of SP600125, JNK-IN-8, tanzisertib (CC-930), CC-401, doramapimod (BIRB 796), RWJ 67657, bentamapimod, BI-78D3, JNK Inhibitor IX, and vacquinol-1. In an embodiment, the JNK inhibitor is SP600125 (1,9-Pyrazoloanthrone, Anthrapyrazolone), and the low-dose of SP600125 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, the MLK inhibitor is selected from the group consisting of URMC-099, CEP-1347 (KT7515), CEP-5104, CEP-11004, and CEP-6331. In an embodiment, wherein the MLK 1/2/3 inhibitor is URMC-099 (3-(1H-indol-5-yl)-5-[4-[(4-methyl-1-piperazinyl)methyl]phenyl]-1H-pyrrolo[2,3-b]pyridine), and the low-dose of URMC-099 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, the DLK inhibitor is selected from the group consisting of URMC-099, GNE-3511, and GDC-0134. In an embodiment, the DLK inhibitor is URMC-099 (3-(1H-indol-5-yl)-5-[4-[(4-methyl-1-piperazinyl)methyl]phenyl]-1H-pyrrolo[2,3-b]pyridine), and the low-dose of URMC-099 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In a second aspect, the invention provides a composition comprising (a) trametinib, (b) SB203580, (c) SP600125, and (d) URMC-099. In certain embodiments of the second aspect, the composition comprises, (a) about 0.005 mg to about 200 mg of trametinib, (b) about 0.005 mg to about 200 mg SB203580, (c) about 0.005 mg to about 200 mg SP600125, and (d) about 0.005 mg to about 200 mg URMC-099.

In a third aspect, the invention provides a method of treating a patient with cancer, comprising administering a therapeutically effective amount of the any of the compositions disclosed herein, wherein the administration of the therapeutically effective amount of the composition prevents invasion of the cancer.

In a fourth aspect, the invention provides a method of treating a patient with cancer, comprising administering a therapeutically effective amount of the any of the compositions disclosed herein, wherein the administration of the therapeutically effective amount of the composition prevents metastasis of the cancer.

In a fifth aspect, the invention provides a method for treating a patient with cancer, comprising
(a) obtaining a cancer sample from the patient;
(b) measuring the expression level of ROCK2, DOCK4, ITGA1, APC, and RAPGEF2 in the cancer sample; and
(c) administering a therapeutically effective amount of the composition of any of compositions described herein to the patient when the expression levels of ROCK2, DOCK4, ITGA1, APC, and RAPGEF2 in the cancer sample are increased relative to the expression levels of the same genes in a control sample.

In certain embodiments of the fifth aspect, the cancer sample comprises a biopsy of a primary cancer tumor. In some embodiments, the primary cancer tumor is breast, pancreatic, ovarian, lung, head and neck, or colorectal.

In some embodiments of the third, fourth, and fifth aspects, the method further comprises administering to the patient one or more of a chemotherapy, a radiation therapy, and an immunotherapy. In certain embodiments, the method further comprises surgical removal of the primary cancer.

In some embodiments of the third, fourth, and fifth aspects, the patient has a primary cancer with decreased RKIP (PEBP1) expression compared to a control sample. In certain embodiments, the patient has a primary cancer with an increased expression of one or more of APC, DOCK4, ADAMS, DAB2, DOCK10, FLNA, FN1, HDAC4, MCAF1, RAPGEF2, and ROBO1 genes compared to a control sample. In some embodiments, the patient has a primary cancer with an increased expression of ROCK2, DOCK4, ITGA1, APC, and RAPGEF2 compared to a control sample.

In some embodiments of the third, fourth, and fifth aspects, the patient has a primary cancer selected from the group consisting of Acute Lymphoblastic Leukemia (ALL), Acute Myeloid Leukemia (AML), Adrenocortical Carcinoma, Kaposi Sarcoma (Soft Tissue Sarcoma), AIDS-Related Lymphoma, Primary CNS Lymphoma, Anal Cancer, Appendix Cancer, Astrocytomas, Brain Cancer, Atypical Teratoid/Rhabdoid Tumor, Basal Cell Carcinoma of the Skin, Bile Duct Cancer, Bladder Cancer, Bone Cancer (including Ewing Sarcoma and Osteosarcoma and Malignant Fibrous Histiocytoma), Breast Cancer, Bronchial Tumors, Burkitt Lymphoma, Non-Hodgkin Lymphoma, Carcinoid Tumor (Gastrointestinal), Cardiac (Heart) Tumors, Cervical Cancer, Cholangiocarcinoma, Chordoma, Chronic Lymphocytic Leukemia (CLL), Chronic Myelogenous Leukemia (CML), Colorectal Cancer, Craniopharyngioma, Cutaneous T-Cell Lymphoma, Ductal Carcinoma In Situ (DCIS), Endometrial Cancer (Uterine Cancer), Esophageal Cancer, Esthesioneuroblastoma (Head and Neck Cancer), Extragonadal Germ Cell Tumor, Eye Cancer, Intraocular Melanoma, Retinoblastoma, Fallopian Tube Cancer, Gallbladder Cancer, Gastric (Stomach) Cancer, Gastrointestinal Stromal Tumors (GIST), Germ Cell Tumors, Testicular Cancer, Gestational Trophoblastic Disease, Hairy Cell Leukemia, Hodgkin Lymphoma, Hypopharyngeal Cancer, Islet Cell Tumors, Pancreatic Neuroendocrine Tumors, Kidney (Renal Cell) Cancer, Langerhans Cell Histiocytosis, Laryngeal Cancer, Leukemia, Lip and Oral Cavity Cancer, Liver Cancer, Lymphoma, Melanoma, Merkel Cell Carcinoma (Skin Cancer), Mesothelioma, Multiple Myeloma/Plasma Cell Neoplasms, Mycosis Fungoides, Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, Oropharyngeal Cancer, Ovarian Cancer, Pancreatic Cancer, Paraganglioma, Parathyroid Cancer, Penile Cancer, Prostate Cancer, Rhabdomyosarcoma, Salivary Gland Cancer, Sarcoma, Uterine Sarcoma, Small Cell Lung Cancer, Small Intestine Cancer, Sèzary Syndrome, Throat Cancer, Thymoma, Thyroid Cancer, Urethral Cancer, Vaginal Cancer, Wilms Tumor, and metastatic forms thereof. In an embodiment, the primary cancer is breast cancer, in particular, triple-negative breast cancer (TNBC).

These and other features and advantages of the present invention will be more fully understood from the following detailed description taken together with the accompanying claims. It is noted that the scope of the claims is defined by the recitations therein and not by the specific discussion of features and advantages set forth in the present description.

DESCRIPTION OF DRAWINGS

FIGS. 1A-1H: RKIP partially inhibits multiple kinases within the extended MAPK network. (FIG. 1A) Heatmap shows 30 kinases whose activity is significantly regulated by RKIP in xenograft BM1 tumors that over-express RKIP (n=6) or the empty vector control (n=5). 23 kinases were downregulated and 7 kinases were upregulated by RKIP. (FIG. 1B) Kinome map highlights the changes in kinomic activity as RKIP reprograms tumors into a non-metastatic state. Shaded node indicates downregulation of activity and shaded node indicated with arrows indicates upregulation of activity for a particular kinase. (FIG. 1C) Heatmap demonstrates the distribution of kinases targeted by RKIP in an activity ranked listed of all 250 kinases. Kinases with high level activity in the control tumors are at the top, and the kinases with low activity are towards the bottom. (FIG. 1D) Bar plot shows the average effect size of changes in kinase activity induced by RKIP in the BM1 tumors included in the MIB analysis. (FIG. 1E) Gene set enrichment analysis of the 23 downregulated kinases using Metascape shows functional gene sets. Bar plot shows the significance p-value for each gene set in the −log10 scale. Stress-induced mitogen activated protein kinase (MAPK) related gene sets are indicated with an asterisk (*). (FIG. 1F) Ingenuity® Pathway Analysis (IPA) shows the predicted functional interactions between the downregulated (light grey shaded triangles) and upregulated (grey shaded triangles indicated with an asterisk (*)) MIB kinases. See the prediction legend for the types of predictions. (FIG. 1G) Protein-protein interaction network and community analysis depicts the topology of the core stress MAPK network regulated by RKIP. (FIG. 1H) Immunoblotting confirms downregulation of the stress MAPKs by wild type RKIP and the Raf-binding S153E mutant in the human BM1 TNBC cell line in vitro. Quantification for each band is normalized to the Tubulin signal in the same blot and depicted above the corresponding blots. Representative of two independent experiments. See also FIGS. 2A-2B.

FIGS. 2A-2B: RKIP targets stress MAPKs p38 and JNK, which are important for TNBC cell migration and invasion. (FIG. 2A) Immunoblotting confirms downregulation of the stress MAPKs by the wild type RKIP and the Raf-binding S153E mutant in the human MB436 cell line and mouse LMB and M6C cell lines in vitro. Quantification for each band is normalized to the Tubulin signal in the same blot and depicted relative to the vector control on the corresponding blots. (FIG. 2B) Chemotactic invasion assays and wound healing migration assays in BM1 cells with the indicated doses of the JNK inhibitor SP600125 and the p38 inhibitor SB203580 show that stress kinases JNK and p38 are necessary for BM1 migration and invasion. Data are shown as mean±SEM of n=3 technical replicates per experimental group. Statistical significance was tested with respect to the control (untreated) group using a two-tailed t-test. *p<0.05, p<0.01, *p<0.001, ****p<0.0001.

FIGS. 3A-3E: Inhibiting the stress MAPKs mimics RKIP function. (FIG. 3A) Immunoblots demonstrate dose-dependent partial downregulation of p-JNK, but not p-p38, by MEK inhibition in anisomycin and serum-induced BM1 cells in vitro. See also FIG. 4A. (FIG. 3B) Dose response curves show the quantification of p-ERK, p-JNK, and p-p38 signal upon treatment with the indicated doses of the MEK inhibitor in four TNBC cell lines under anisomycin- or serum-induced conditions. Each dot on the graph represents the response of a cell line normalized to the signal in the non-treated cells. Dashed bars represent the p-ERK, p-JNK, and p-p38 signaling in the non-treated cells which is set to an average of 1. See also FIG. 4B. (FIG. 3C) Chemotactic invasion assay demonstrates a decrease in BM1 invasion when TAO kinases are knocked down by siRNAs individually or all together. Data are shown as mean±SEM of n=3 technical replicates per experimental group. Representative of two independent experiments. Statistical significance was tested with respect to the control (non-targeting siRNA) group using a two-tailed t-test. See also FIG. 4G for the similar data in MB436 cells. (FIG. 3D) Chemotactic invasion assay shows dose-dependent downregulation of BM1 invasion when treated with increasing doses of the MLK inhibitor URMC-099. Data are shown as mean±SEM of n=3 technical replicates per experimental group. Representative of two independent experiments. Statistical significance was tested with respect to the control (0.1% DMSO treated) group using a two-tailed t-test. See also FIGS. 4F and 4G for similar data in MB436 cells. (FIG. 3E) Diagram summarizing the regulation of the MAPK network by RKIP in BM1 cells in vitro. *p<0.05, p<0.01, *p<0.001, ****p<0.0001.

(FIG. 4A) Immunoblots demonstrate the context-dependent responses of p38 and JNK kinases to MEK inhibition (MEKi) in TNBC cell lines MB436, LMB, and M6C under anisomycin or serum induction. (FIG. 4B) Immunoblots (top panel) show activity of TAOK1/2/3 in syngeneic M6C tumors with exogenous RKIP expression. Densitometry quantification (bottom panel) of phosphorylated TAOKs demonstrates the inhibition of TAOK2, but not TAOK1 and TAOK3 by RKIP in n=8 RKIP tumors with respect to n=7 control tumors. Data are shown as mean ±SEM. Statistical significance was tested using a two-tailed t-test. (FIG. 4C) Immunoblots show the downregulation of TAOK1/2/3 and MLK3 activity in BM1 and MB436 cells expressing wild type RKIP or the S153E mutant. (FIG. 4D) Immunoblots demonstrate the downregulation of p38 and JNK stress kinase activity in vitro when TAO kinases were knocked down in BM1 and MB436 cells by siRNAs against TAOK1, TAOK2, and TAOK3 individually or all together (si-Combo) (si-NT, non-targeting siRNA). (FIG. 4E) Dose response immunoblot shows MLK inhibition (MLKi) with URMC-099 decreases JNK and p38 activity in anisomycin-induced BM1 or MB436 cells in vitro. (FIG. 4F) Chemotactic invasion assay demonstrates a decrease in MB436 invasion when TAO kinases are knocked down by siRNAs individually or all together. Data are shown as mean±SEM of n=3 technical replicates per experimental group. Representative of two independent experiments. Statistical significance was tested with respect to the control (non-targeting siRNA) group using a two-tailed t-test. (FIG. 4G) Chemotactic invasion assay shows dose-dependent downregulation of MB436 invasion when treated with increasing doses of the MLK inhibitor URMC-099. Data are shown as mean±SEM of n=3 technical replicates per experimental group. Representative of two independent experiments. Statistical significance was tested with respect to the control (0.1% DMSO treated) group using a two-tailed t-test. *p<0.05, p<0.01, *p<0.001, ****p<0.0001.

(FIG. 5A) Immunoblots show the differential crosstalk between p38 and JNK signaling in serum-induced BM1 cells (p38i=p38 inhibition; JNKi=JNK inhibition). Representative of two independent experiments. (FIG. 5B) Immunoblots show the differential cross-talk between p38 and JNK signaling in anisomycin-induced BM1 cells. Representative of two independent experiments. (FIG. 5C) Immunoblots demonstrate the negative feedback between p38 and JNK signaling under serum conditions in MB436, LMB, and M6C cells. (FIG. 5D) SB203580 induced JNK activation, but not SP600125 induced p38 activation, is mediated through the MLKs.

(FIG. 6A) Diagram shows the small molecule inhibitors used in the high-throughput invasion assays for potential drug combinations. (FIG. 6B) Chemotactic invasion assay demonstrating the efficacy of the 4-drug combination vs. the 2-drug combinations in blocking invasion over time at 1× or 2×doses. The insets show the 3D proliferation of the cells under the same conditions as the invasion assay. Data are plotted as mean±SEM of n=3 technical replicates per experimental group. Statistical significance was determined by a two-way ANOVA with Tukey's multiple tests correction. The p-values are for the 72-hour time point comparisons. See also FIGS. 7A-C for the single drug dose response experiments, 2-drug and 3-drug combinations tested in the high throughput invasion assays. (FIG. 6C) Immunoblots show that the 4-drug combination is more effective than the dual combinations in inhibiting all three MAPKs in anisomycin-induced BM1 cells. The heatmap shows the densitometry intensity for p-p38, p-JNK, and p-ERKs, normalized the Tubulin signal for each blot and calibrated to the control (DMSO treated) samples. Representative of two independent experiments. See also FIG. 7D for the results in MB436 and LMB cell lines. (FIG. 6D) 3D proliferation assays (left panel) and chemotactic invasion assays (right panel), for each cell line tested, showing that the 4-drug combination inhibits invasion of MB436, LMB, and M6C cells without inhibiting their growth. Data are plotted as mean±SEM of n=3 technical replicates per experimental group. Statistical significance was determined by a two-way ANOVA test with Tukey's multiple comparison correction for the proliferation assays, and by a two-tailed student's t-test for the invasion assays. (FIG. 6E) Proliferation assay confirming that the 4-drug MAPKi combination is not toxic to the normal mammary epithelial 184A1 cells. Data are plotted as mean±SEM of n=3 technical replicates per experimental group. Statistical significance was determined by a two-way ANOVA test with Tukey's multiple comparison correction. See also FIG. 7E for similar results in the MCF10A cell line. For all plots: *p<0.05, p<0.01, *p<0.001, ****p<0.0001.

(FIG. 7A) Dose escalation experiments with the six inhibitors of the MAPK network demonstrating the range of doses for each inhibitor at which nuclear-labeled BM1 invasion is at least partially reduced over 72 hours, but proliferation is unaffected. Insets show 3D proliferation overtime (elapsed time of 72 hours) of BM1 cells at the same doses over 72 hours. (FIG. 7B) Dual combinations of MAPK inhibitors tested. The two combinations that showed potential combinatorial effect on BM1 invasion (MEKi+MLKi, p38i+JNKi) are highlighted in the top panel box. (FIG. 7C) BM1 invasion and proliferation when a third inhibitor is added to the dual combinations reveal non-additive nature of MAPK inhibitors used. (FIG. 7D) Immunoblots show that the 4-drug combination is more effective than the dual combinations in inhibiting all three MAPKs in anisomycin-induced MB436 and LMB cells. The heatmap shows the densitometry intensity for p-p38, p-JNK, and p-ERKs, normalized the Tubulin signal for each blot and calibrated to the control (DMSO treated) samples. (FIG. 7E) Proliferation assay confirming that the 4-drug MAPKi combination is not toxic to normal mammary epithelial MCF10A cells. For all graphs, data are plotted as mean±SEM of n=3 technical replicates per experimental group. Statistical significance was determined by a two-way ANOVA test with Tukey's multiple comparison correction. P-values are for the comparisons at 72 hours. *p<0.05, p<0.01, *p<0.001, ****p<0.0001.

(FIG. 8A) 4-drug MAPKi combination reduces metastatic tumor burden in the lungs of LMB syngeneic mice. Top panel depicts the experimental design and the treatment timeline. H&E staining demonstrates the metastatic lesions in cross-sections of the lungs in mice treated with 1× (undiluted, n=10 biological replicates) MAPKi, 0.5× (diluted, n=8) MAPKi, or the control (vehicle, n=8). Bottom panel shows the quantification of the metastatic lesions on the lung surface. Data are shown as mean±SEM. Statistical significance was determined by a one-way ANOVA test with Dunnett's correction for multiple testing. Exact p-values are reported with respect to the control group. For the dose-response experiments conducted to determine the doses to be used in the 4-drug combination, see FIG. 9A. (FIG. 8B) Effect of MAPKi treatment on the primary LMB tumor growth. Data are plotted as mean±SEM of n=5 biological replicates per experimental group. Statistical significance was determined by a two-way ANOVA test. (FIG. 8C) 4-drug MAPKi combination reduces metastatic tumor burden in the lungs of LMB syngeneic mice even after 2 days (2 doses over 48 hours, on day 0 and day 1) of treatment. Data are shown as mean±SEM of n=10 control tumors and n=8 MAPKi (1×) treated tumors. Statistical significance was determined by unpaired two-tailed student's t-test. (FIG. 8D) Bioluminescence images showing that 4-drug MAPKi combination reduces metastatic tumor burden in the bones of athymic nude mice inoculated with luciferase-expressing BM1 cells. Top panel depicts the experimental design and the treatment timeline. Bottom panel shows the quantification of the metastatic lesions on the lung surface (total flux, luminescence values were evaluated as total photon flux and expressed as photons/sec (p/s)). Statistical significance was determined by a one-way ANOVA test with Dunnett's correction for multiple testing. (FIG. 8E) Kaplan-Meier curve shows overall survival benefit after 3 weeks of MAPKi treatment in xenograft mice injected with BM1 cells via the intracardiac route. Statistical significance was determined by log-rank (Mantel-Cox) test. (FIG. 8F) Primary BM1 tumor growth in athymic nude mice is inhibited in mice treated with MAPKi combination for 4 weeks. Data are plotted as mean±SEM of n=8 control tumors, n=8 MAPKi (0.5×) treated tumors, and n=6 MAPKi (1×) treated tumors. Statistical significance was determined by a two-way ANOVA test with multiple comparisons at the end of the 4-week treatment period.

(FIG. 9A) Dose-response experiments reveal that p38i, JNKi, and MLKi do not affect primary LMB tumor growth determined by final tumor weight in a syngeneic model at 10 mg/kg/day or lower. MEKi, on the other hand, decreases tumor growth in a dose-dependent manner. Dashed lines indicate the doses chosen to be used in the 4-drug combination in vivo. Biological replicates are shown as mean±SEM. (FIG. 9B) Comparison of mouse weights before and after MAPKi treatment reveal no overall toxicity to the mice due to drug treatment in syngeneic or xenograft models. Statistical significance was tested with a paired t-test.

(FIG. 10A) MA plot summarizes the RNA-seq data highlighting the genes differentially regulated between BM1 and BM1-RKIP tumors. Darker grey indicates (encircled) the genes that are expressed at significantly different levels in n=5 RKIP tumors with respect to n=7 control tumors. Genes that have negative log fold change are downregulated (2824 genes), and the ones with the positive log fold change are upregulated (2922). For principle component analysis of the samples, see FIG. 11A. (FIG. 10B) Diagram describes the bioinformatic strategy used to identify clinically-relevant putative RKIP target genes. Heatmap shows FDR corrected p-values for the indicated gene sets in the −log10 scale. Putative targets were filtered by (1) literature evidence for involvement in the metastatic phenotype and (2) ENCODE chip-seq data for having binding sites for ATF, JUN, and MYC transcription factors. 15 candidate RKIP target genes upon this filtering are listed on the right. For the gene set enrichment analysis of downregulated genes in the BM1 tumor RNA-seq data, see FIG. 11B. (FIG. 10C) Heatmap showing relative expression levels of the 15 putative RKIP target genes in the RNA-seq data from n=7 control tumors and n=5 RKIP tumors. Expression values are scaled row-wise. (FIG. 10D) Genes from the heatmap in (C) are plotted individually. Normalized counts for the indicated genes are shown as mean±SEM. Significance was determined two-tailed t-test. (FIG. 10E) Expression of the RKIP target genes in LMB syngeneic tumors treated with MAPKi combination for 3 weeks or the vehicle. Data are plotted as mean±SEM of n=5 control tumors, and n=5 MAPKi (1×) treated tumors. Statistical significance is determined by two-tailed t-test. *p<0.05, p<0.01, *p<0.001, ****p<0.0001.

FIGS. 11A-11G: RKIP regulates cell motility and adhesion genes in vivo and in vitro. Related to FIGS. 10A-10E. (FIG. 11A) Principle component analysis of n=7 BM1-control tumors and n=5 BM1-RKIP tumors used the RNA-seq analysis. (FIG. 11B) Gene set enrichment analysis by Metascape of genes downregulated by RKIP in the RNA-seq data. FDR corrected p-values are ranked in −log(10) scale. (FIG. 11C) Summary table listing RKIP target genes, their fold change in RKIP-expressing BM1 xenograft tumors in the RNA-seq data (FC(log2)), their Pearson (P) and Spearman (S) correlation coefficients with RKIP in TCGA breast cancer dataset, and whether these genes have binding sites for the transcription factors JUN, ATF, MYC, and BACH1 in the ENCODE database. (FIG. 11D) Transcription factor binding according to ENCODE data around the transcription start site for the individual motility/adhesion target genes displayed on USCS Gene Browser. (FIG. 11E) Quantitative RT-PCR shows regulation of motility and adhesion gene transcripts by RKIP (wild type or S153E mutant) in BM1 cells under anisomycin-induced stress conditions in vitro. Data are shown as mean±SEM of n=3 technical replicates. Statistical significance was determined using one-way ANOVA with multiple testing. (FIG. 11F) Quantitative RT-PCR shows regulation of motility and adhesion gene transcripts by RKIP (wild type or S153E mutant) in MB436 cells under anisomycin-induced stress conditions in vitro. Data are shown as mean±SEM of n=3 technical replicates. Statistical significance was determined using one-way ANOVA with multiple testing. (FIG. 11G) Quantitative RT-PCR shows regulation of motility and adhesion gene transcripts by the 4-drug MAPKi combination vs. the dual combinations in BM1 cells under 3D anisomycin-induced stress conditions in vitro. Data are shown as mean±SEM of n=3 technical replicates. Statistical significance was determined using one-way ANOVA with multiple testing and reported with respect to the anisomycin-induced untreated samples (black). *p<0.05, p<0.01, *p<0.001, ****p<0.0001.

FIGS. 12A-12H: BACH1, an RKIP target, mediates stress-induced transcription of invasion genes. (FIG. 12A) mRNA expression shows that RKIP downregulates BACH1 transcription in BM1 tumors (RNA-seq results from FIGS. 9A-B and 10A-10E replotted). Normalized read counts for BACH1 gene are plotted as mean±SEM of n=7 control tumors and n=5 RKIP tumors. Multiple testing corrected p-value was calculated using a Wald test as a part of the DEseq2 R package. (FIG. 12B) Quantitative RT-PCR shows downregulation of BACH1 gene transcript in LMB syngeneic tumors treated with MAPKi combination for 3 weeks. Data are shown as mean±SEM of n=5 control tumors and n=5 MAPKi (1×) treated tumors. The values are normalized to the control group. Statistical significance is determined by two-tailed t-test. *p<0.05, p<0.01, *p<0.001, ****p<0.0001. (FIG. 12C) Quantitative RT-PCR analysis demonstrates that 4D-MAPKi combination blocks BACH1 induction under anisomycin-induced stress conditions in BM1 cells. Data are shown as mean±SEM of n=3 technical replicates. Representative of three independent experiments. Statistical significance was determined with respect to the control samples, using ANOVA with multiple testing. (FIG. 12D) In BM1 cells, BACH1 expression can be regulated by all three MAPKs. Bars with the pound symbol (#) in the bar graphs indicate the doses used in 4D-MAPKi for each inhibitor. Data are shown as mean±SEM of n=3 technical replicates. Statistical significance was determined using one-way ANOVA with multiple testing. For the results in MB436 and LMB cell lines, see FIGS. 13A-D. (FIG. 12E) Immunoblots confirm the inhibition of BACH1 protein expression by the MAPKi combination in human TNBC cell lines. Representative of two independent experiments. (FIG. 12F) Heatmap shows the corrected p-values for the motility and adhesion related gene sets enriched with genes negatively regulated by RKIP, and positively correlated with BACH1. (FIG. 12G) Quantitative RT-PCR analysis of RKIP target gene expression in BM1 shBACH1 cells under anisomycin-induced stress. Data are shown as mean±SEM of n=3 technical replicates. Statistical significance was determined with respect to the control samples, using ANOVA with multiple testing. For the results in MB436 cells, see FIG. 13G. (FIG. 12H) Chromatin immunoprecipitation analysis indicates direct binding of BACH1 transcription factor on the indicated regions of the RKIP target genes. Data are shown as mean±SEM of two independent experiments (average of n=3 technical replicates per experiment was plotted).

FIGS. 13A-13G: BACH1 expression is regulated by different MAPKs in different TNBC cell lines. Related to FIGS. 12A-12H. Quantitative RT-PCR analysis demonstrates that the 4-drug MAPKi combination blocks BACH1 induction under anisomycin-induced stress conditions in MB436 (FIG. 13A) and LMB (FIG. 13B) (representative of two independent experiments). BACH1 expression is regulated by p38 and JNK in MB436 (FIG. 13C) cells, but by JNK and MEK in LMB (FIG. 13D) cell. Bars with the pound symbol (#) in the bar graphs indicate the doses used in the 4-drug combination for each inhibitor. Data are shown as mean±SEM of n=3 technical replicates. Statistical significance was determined using one-way ANOVA with multiple testing. (FIG. 13E) Diagrams summarize the regulation of BACH1 by MAPKs in different TNBC cell lines. (FIG. 13F)

Immunoblot show the inhibition of BACH1 protein expression by the MAPKi combination in LMB cells. (FIG. 13G) Quantitative RT-PCR analysis of RKIP target gene expression in MB436 shBACH1 cells under anisomycin-induced stress. Data are shown as mean±SEM of n=3 technical replicates. Statistical significance was determined with respect to the control samples, using ANOVA with multiple testing.

(FIG. 14A) Heatmap displays distribution of RKIP target gene expression based on TNBC status in the TCGA breast cancer data set. TNBC status is determined as negative IHC signal for ER, PR, and HER2 receptors in the patient data. Each column represents a breast cancer sample (n=1100). (FIG. 14B) Graphs show the genes that are significantly enriched in the TNBC portion of the TCGA breast cancer patient data set. z-transformed expression value for the indicated genes are plotted as mean±SEM of n=115 TNBC cases, and n=985 other cases. Statistical significance was determined with a two-tailed t-test. (FIG. 14C) Heatmap shows expression of RKIP target genes in individual breast cancer patients in the TCGA data set based on RKIP-high (z-score>0.5) vs. RKIP-low (z-score<0.5) status. (FIG. 14D) Gene signature consisting of 5 motility/adhesion target genes (TG) predicts overall survival in TCGA breast cancer data set in a univariate analysis. Statistical significance was determined by a log-rank test. (FIG. 14E) Gene sets enriched with genes negatively correlated with RKIP across multiple TCGA cancer types. The heatmap shows the corrected p-values in −log(10) scale. (FIG. 14F) Heatmap summarizes the Spearman correlation coefficient for motility and adhesion related genes in correlation with RKIP in TCGA cancers. Correlation coefficients higher than −0.3 was displayed as a black box. (FIG. 14G) Genes that negatively correlate with the indicated metastasis suppressors in the TCGA breast cancer data are enriched in motility and adhesion related gene sets. The heatmap shows the corrected p-values in −log(10) scale. (FIG. 14H) Diagram summarizing the findings about RKIP-mediated metastasis suppression in this disclosure.

(FIG. 15A) Graph of inhibition of macrophage infiltration in LMB tumors. Macrophage infiltration was quantified in n=5 untreated tumors, and n=5 4D-MAPKi treated tumors, and normalized to the average infiltration in the control set. Data are shown as mean±SEM and statistical significance was determined by a two-tailed t-test. (FIG. 15B) Immunohistochemical analysis of macrophage infiltration within the primary LMB tumor tissues. Tumors sections from FIG. 15A were stained for F4/80 macrophage marker.

DETAILED DESCRIPTION

Figure 1A:
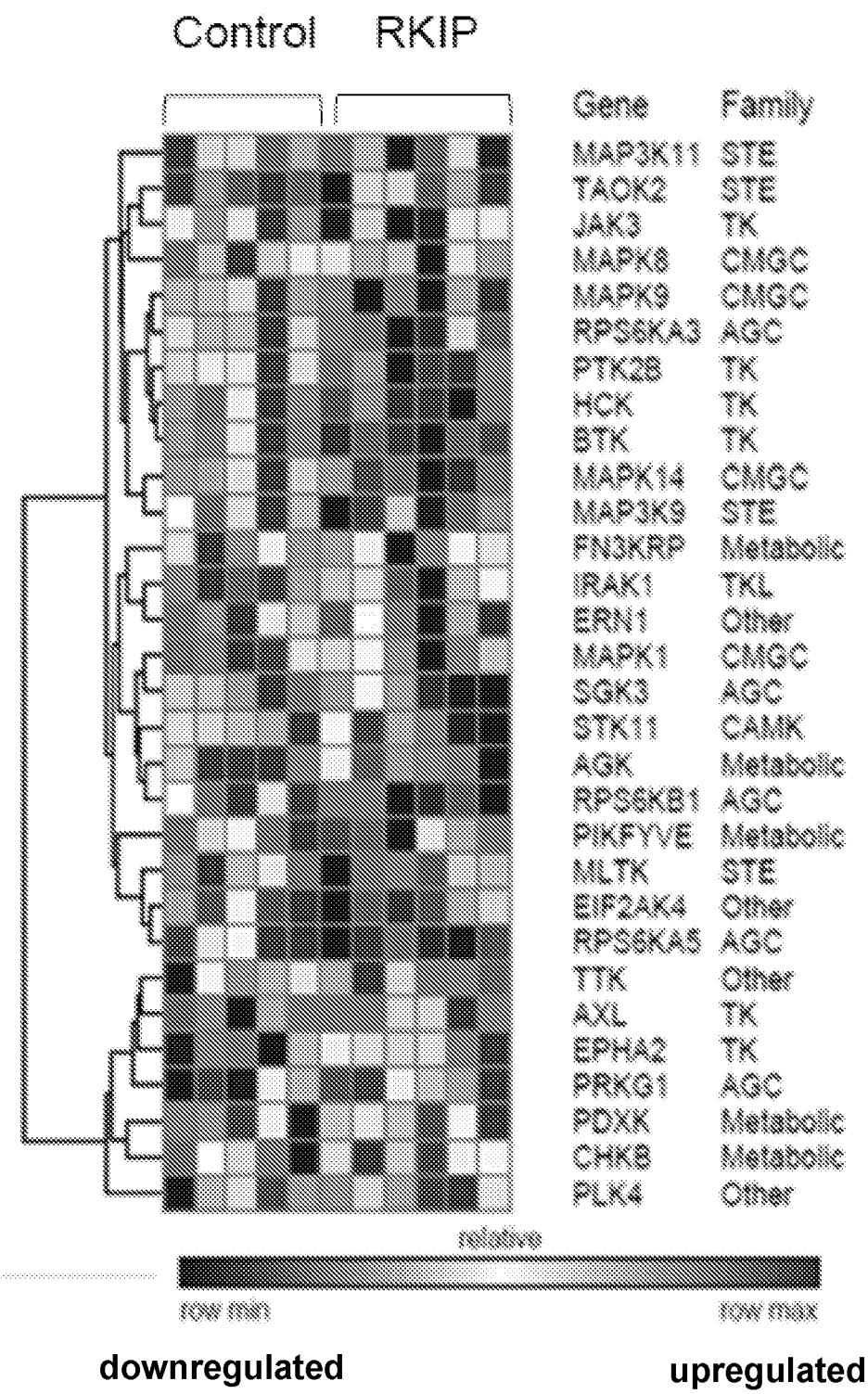

Cancer metastasis is estimated to account for approximately 90% of human cancer related deaths. For example, metastatic progression of tumors is the major cause of death in patients with triple negative breast cancer (TNBC). However, since metastasis is a multi-step process, unraveling its complexity is a major challenge. One effective way of tackling this question is to study natural blockers of the metastatic process, metastasis suppressors, and identify the mechanisms by which they regulate metastasis. Raf kinase inhibitory protein (RKIP), a protein that regulates kinase activity, is a suppressor of TNBC metastasis. Although RKIP inhibits the activity of key kinases such as Raf-1, GRK2, and NIK/IKK in cultured cells, the kinase targets of RKIP in tumors are not known. To address this question, a mass spectrometry approach involving inhibitor-conjugated beads was used to identify kinases that are down-regulated by RKIP in human TNBC xenograft tumors. The results identified a network of stress kinases targeted by RKIP, including kinases that have not been previously reported as RKIP targets. In order to unravel the effect of this stress network on metastatic gene expression, genes that correlate with RKIP expression in the cancer genome atlas (TCGA) breast cancer patient data set were investigated. Pro-metastatic genes such as APC and DOCK4 were identified as novel RKIP targets in in vitro and in vivo models of TNBC. It was also demonstrated that these genes are downstream of the RKIP-stress network. By using a high-throughput invasion assay, a low-dose, multi-drug cocktail of small-molecule kinase inhibitors that mimic RKIP's anti-metastatic role in TNBCs was identified. Elucidating RKIP function at a systems level reveals the interplay between key metastatic signaling cascades, particularly in relation to cell motility and invasion. These findings suggest that the low-dose multi-drug combination that targets a network of stress kinases is a viable anti-metastatic therapy for cancer patients. In particular, combinations of MAPK inhibitors that can inhibit multiple MAPK axes (for example, p38, JNK, and ERK) simultaneously can be an effective treatment in preventing invasion and metastasis of cancer.

All publications, patents, and patent applications cited herein are hereby expressly incorporated by reference in their entirety for all purposes.

Before describing the present invention in detail, a number of terms will be defined. As used herein, the singular forms "a," "an," and "the" include plural referents unless the context clearly dictates otherwise.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" as used herein represents the inherent degree of uncertainty that can be attributed to any quantitative comparison, value, measurement, or other representation. The term "substantially" is also used herein to represent the degree by which a quantitative representation can vary from a stated reference without resulting in a change in the basic function of the subject matter at issue.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is also contemplated that anything listed using the term "or" may also be specifically excluded.

As used herein, the term "about" refers to±10% of a given value.

The present disclosure is directed, in part, to a novel approach for anti-metastatic therapies against cancer utilizing a combination of at least two inhibitors of the MAPK pathway. Additional aspects and embodiments of the disclosure are presented below.

In a first aspect, the invention provides a composition, comprising combination of drugs comprising at least two or more inhibitors of the mitogen-activated protein kinase (MAPK) pathway, wherein the at least two or more inhibitors are selected from inhibitors of: MEK1, MEK2, p38MAPK, JNK1, JNK2, JNK3, MLK 1, MLK2, MLK3, TAOK1, TAOK2, DLK, MAP2K4, MAP3K1, MAP3K2, MAP3K3, MAP3K4, MAP3K5, MAP3K6, MAP3K7, MAP3K8, MAP3K12, MAP3K13, MAP3K14, MAP3K15, MAP3K20, RAF1, BRAF, and ARAF. In some embodiments, each of the at least two or more inhibitors is present in a low-dose. In an embodiment of the composition, the at least two or more inhibitors comprise (a) a MEK inhibitor, (b) a p38MAPK inhibitor, (c) a JNK inhibitor, and (d) a MLK inhibitor.

As used herein, the term "low-dose" refers to a dose which is pharmaceutically effective in inbiting metastasis and/or invasion of cancer cells while not affecting proliferation and/or growth rate of the cancer cells or normal cells. A "low-dose" composition also results in the substantial absence of toxic side effects, for example, in the substantial absence of grade 3 or higher of National Cancer Institute (NCI) Common Toxicity Criteria (CTC) v2.0, April 1999, or in the substantial absence of grade 2 or higher, or in the substantial absence of grade 1 or higher (also see Common Terminology Criteria for Adverse Events (CTCAE) v5.0, November 2017). In certain embodiments, a "low-dose" of each of the at least two or more MAPK inhibitors improves the efficacy of radiation therapy, chemotherapy, and/or immunotherapy. In some embodiments, due to the non-toxic nature of the low-dose composition comprising the at least two or more inhibitors of the MAPK pathway, the composition can be effective as a continuous therapy.

In certain embodiments of the first aspect, the MEK inhibitor is selected from the group consisting of trametinib (Mekinist™), cobimetinib (Cotellic™), binimetinib (MEK162, ARRY-162), selumetinib (AZD6244), pimasertib (AS-703026), refametinib (RDEA119, Bay 86-9766), PD-325901, PD-035901, PD-184352 (CI-1040), TAK-733, U0126-EtOH, and BI-847325. In an embodiment, the MEK inhibitor is trametinib (Mekinist™), and the low-dose of trametinib (Mekinist™) in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, the p38MAPK inhibitor is selected from the group consisting of SB203580, doramapimod (BIRB 796), SB202190 (FHPI), ralimetinib (LY2228820), VX-702, PH-797804, VX-745, TAK-715, pamapimod (R-1503, Ro4402257), BMS-582949, SB239063, losmapimod (GW856553X), skepinone-L, and pexmetinib (ARRY-614). In an embodiment, the p38MAPK inhibitor is SB203580 (4-(4-Fluorophenyl)-2-(4-methylsulfinylphenyl)-5-(4-pyridyl)-1H-imidazole), and the low-dose of SB203580 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, the INK inhibitor is selected from the group consisting of SP600125, JNK-IN-8, tanzisertib (CC-930), CC-401, doramapimod (BIRB 796), RWJ 67657, bentamapimod, BI-78D3, JNK Inhibitor IX, and vacquinol-1. In an embodiment, the INK inhibitor is SP600125 (1,9-Pyrazoloanthrone, Anthrapyrazolone), and the low-dose of SP600125 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, the MLK inhibitor is selected from the group consisting of URMC-099, CEP-1347 (KT7515), CEP-5104, CEP-11004, and CEP-6331. In an embodiment, wherein the MLK 1/2/3 inhibitor is URMC-099 (3-(1H-indol-5-yl)-5-[4-[(4-methyl-1-piperazinyl)methyl]phenyl]-1H-pyrrolo[2,3-b]pyridine), and the low-dose of URMC-099 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

In certain embodiments of the first aspect, wherein the DLK inhibitor is selected from the group consisting of URMC-099, GNE-3511, and GDC-0134. In an embodiment, the DLK inhibitor is URMC-099 (3-(1H-indol-5-yl)-5-[4-[(4-methyl-1-piperazinyl)methyl]phenyl]-1H-pyrrolo[2,3-b]pyridine), and the low-dose of URMC-099 in the combination is about 0.005 mg, or about 0.01 mg, or about 0.05 mg, or about 0.1 mg, or about 0.2 mg, or about 0.3 mg, or about 0.4 mg, or about 0.5 mg, or about 0.6 mg, or about 0.7 mg, or about 0.8 mg, or about 0.9 mg, or about 1.0 mg, or about 1.5 mg, or about 2.0 mg, or about 5.0 mg, or about 10 mg, or about 20 mg, or about 30 mg, or about 40 mg, or about 50 mg, or about 100 mg, or about 200 mg or more.

TABLE 1

| List of potential targets. | | | |
|---|---|---|---|
| Official Symbol (by HGNC) | Official Full Name (by HGNC) | Also known as | Other |
| MAP2K1 | mitogen-activated protein kinase kinase 1 | CFC3; MEK1; MKK1; MAPKK1; PRKMK1 | Gene ID: 5604 |
| MAP2K2 | mitogen-activated protein kinase kinase 2 | CFC4; MEK2; MKK2; MAPKK2; PRKMK2 | Gene ID: 5605 |
| MAPK1 | mitogen-activated protein kinase 1 | ERK; p38; p40; p41; ERK2; ERT1; ERK-2; MAPK2; PRKM1; PRKM2; P42MAPK; p41mapk; p42-MAPK | Gene ID: 5594 |

TABLE 1-continued

List of potential targets.

| Official Symbol (by HGNC) | Official Full Name (by HGNC) | Also known as | Other |
|---|---|---|---|
| MAPK14 | mitogen-activated protein kinase 14 | RK; p38; CSBP; EXIP; Mxi2; CSBP1; CSBP2; CSPB1; PRKM14; PRKM15; SAPK2A; p38ALPHA | Gene ID: 1432 |
| MAPK11 | mitogen-activated protein kinase 11 | P38B; SAPK2; p38-2; PRKM11; SAPK2B; p38Beta; P38BETA2 | Gene ID: 5600 |
| MAPK8 | mitogen-activated protein kinase 8 | JNK; JNK1; PRKM8; SAPK1; JNK-46; JNK1A2; SAPK1c; JNK21B1/2 | Gene ID: 5599 |
| MAPK9 | mitogen-activated protein kinase 9 | JNK2; SAPK; p54a; JNK2A; JNK2B; PRKM9; JNK-55; SAPK1a; JNK2BETA; p54aSAPK; JNK2ALPHA | Gene ID: 5601 |
| MAPK10 | mitogen-activated protein kinase 10 | JNK3; JNK3A; PRKM10; SAPK1b; p493F12; p54bSAPK | Gene ID: 5602 |
| MAP2K4 | mitogen-activated protein kinase kinase 4 | JNKK; MEK4; MKK4; SEK1; SKK1; JNKK1; SERK1; MAPKK4; PRKMK4; SAPKK1; SAPKK-1 | Gene ID: 6416 |
| MAP3K1 | mitogen-activated protein kinase kinase kinase 1 | MEKK; MEKK1; SRXY6; MEKK 1; MAPKKK1 | Gene ID: 4214 |
| MAP3K2 | mitogen-activated protein kinase kinase kinase 2 | MEKK2; MEKK2B | Gene ID: 10746 |
| MAP3K3 | mitogen-activated protein kinase kinase kinase 3 | MEKK3; MAPKKK3 | Gene ID: 4215 |
| MAP3K4 | mitogen-activated protein kinase kinase kinase 4 | MTK1; MEKK4; MEKK 4; MAPKKK4; PRO0412 | Gene ID: 4216 |
| MAP3K5 | mitogen-activated protein kinase kinase kinase 5 | ASK1; MEKK5; MAPKKK5 | Gene ID: 4217 |
| MAP3K6 | mitogen-activated protein kinase kinase kinase 6 | ASK2; MEKK6; MAPKKK6 | Gene ID: 9064 |
| MAP3K7 | mitogen-activated protein kinase kinase kinase 7 | CSCF; FMD2; TAK1; MEKK7; TGF1a | Gene ID: 6885 |
| MAP3K8 | mitogen-activated protein kinase kinase kinase 8 | COT; EST; ESTF; TPL2; AURA2; MEKK8; Tpl-2; c-COT | Gene ID: 1326 |
| MAP3K9 | mitogen-activated protein kinase kinase kinase 9 | MLK1; MEKK9; PRKE1 | Gene ID: 4293 |
| MAP3K10 | mitogen-activated protein kinase kinase kinase 10 | MST; MLK2; MEKK10 | Gene ID: 4294 |
| MAP3K11 | mitogen-activated protein kinase kinase kinase 11 | MLK3; PTK1; SPRK; MLK-3; MEKK11 | Gene ID: 4296 |
| MAP3K12 | mitogen-activated protein kinase kinase kinase 12 | DLK; MUK; ZPK; ZPKP1; MEKK12 | Gene ID: 7786 |
| MAP3K13 | mitogen-activated protein kinase kinase kinase 13 | LZK; MLK; MEKK13 | Gene ID: 9175 |
| MAP3K14 | mitogen-activated protein kinase kinase kinase 14 | HS; NIK; HSNIK; FTDCR1B | Gene ID: 9020 |
| MAP3K15 | mitogen-activated protein kinase kinase kinase 15 | ASK3; bA723P2.3 | Gene ID: 389840 |
| TAOK1 | TAO kinase 1 | MAP3K16; PSK2; TAO1; KFC-B; MARKK; PSK-2; hKFC-B; hTAOK1; | Gene ID: 57551 |
| TAOK2 | TAO kinase 2 | MAP3K17; PSK; PSK1; TAO1; TAO2; PSK1-BETA | Gene ID: 9344 |
| RAF1 | Raf-1 proto-oncogene, serine/threonine kinase | NS5; CRAF; Raf-1; c-Raf; CMD1NN | Gene ID: 5894 |
| BRAF | B-Raf proto-oncogene, serine/threonine kinase | NS7; B-raf; BRAF1; RAFB1; B-RAF1 | Gene ID: 673 |
| ARAF | A-Raf proto-oncogene, serine/threonine kinase | PKS2; A-RAF; ARAF1; RAFA1 | Gene ID: 369 |
| MAP3K20 | mitogen-activated protein kinase kinase kinase 20 | ZAK; pk; AZK; MLT; MRK; CNM6; MLK7; MLTK; SFMMP; mlklak; MLTKbeta; MLTKalpha | Gene ID: 51776 |

Information in this table was obtained on the World Wide Web from: ncbi.nlm.nih.gov/gene One of skill in the art would understand that the naming of a particular gene or target can vary (e.g., the same gene can have multiple synonyms); as such, contemplated targets can include any such alternative names of a target as understood by one of skill in the art.

In a second aspect, the invention provides a composition comprising (a) trametinib, (b) SB203580, (c) SP600125, and (d) URMC-099. In certain embodiments of the second aspect, the composition comprises (a) about 0.005 mg to about 200 mg of trametinib, (b) about 0.005 mg to about 200 mg SB203580, (c) about 0.005 mg to about 200 mg SP600125, and (d) about 0.005 mg to about 200 mg is URMC-099. In certain embodiments, the composition comprises about 10 mg/kg of the p38 inhibitor, about 10 mg/kg of the JNK inhibitor, about 10 mg/kg of the MLK inhibitor, and about 5 mg/kg of the MEK inhibitor. In some embodiments, the administered dose for SB203580 is 10 mg/kg/day, URMC-099 is 10 mg/kg/day, SP600125 is 10 mg/kg/day, and Trametinib is 0.5 mg/kg/day.

In a third aspect, the invention provides a method of treating a patient with cancer, comprising administering a therapeutically effective amount of the any of the compositions disclosed herein, wherein the administration of the therapeutically effective amount of the composition prevents invasion of the cancer.

In a fourth aspect, the invention provides a method of treating a patient with cancer, comprising administering a therapeutically effective amount of the any of the compositions disclosed herein, wherein the administration of the therapeutically effective amount of the composition prevents metastasis of the cancer.

In a fifth aspect, the invention provides a method for treating a patient with cancer, comprising:
(a) obtaining a cancer sample from the patient;
(b) measuring the expression level of ROCK2, DOCK4, ITGA1, APC, and RAPGEF2 in the cancer sample;
(c) administering a therapeutically effective amount of the composition of any of compositions described herein to the patient when the expression levels of ROCK2, DOCK4, ITGA1, APC, and RAPGEF2 in the cancer sample are increased relative to the expression levels of the same genes in a control sample.

As used herein, the terms "subject" or "patient" refer to any single subject for which treatment is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

A sample may include, but is not limited to, tissue, cells, or biological material derived from cells of a subject. The sample may be a tumor, a cancer, or cancer cells. The sample may be obtained using any method known to the art that can provide a sample suitable for the analytical methods described herein. In certain embodiments, the sample may be obtained by non-invasive methods including but not limited to: scraping of the skin or cervix, swabbing of the cheek, saliva collection, urine collection, feces collection, collection of menses, tears, or semen. In some embodiment, the sample can be obtained by an invasive procedure including but not limited to: biopsy, needle aspiration, excision, or phlebotomy. The method of needle aspiration may further include fine needle aspiration, core needle biopsy, vacuum assisted biopsy, or large core biopsy. In some embodiments, the sample may be obtained by a physician, nurse, or other medical professional such as a medical technician, endocrinologist, cytologist, phlebotomist, radiologist, or a pulmonologist.

In some embodiments of the fifth aspect, the patient is predicted to have a decreased overall survival or decreased chance of have metastatic-free survival when the cancer cells from the patient are determined to have increased expression levels of ROCK2, DOCK4, ITGA1, APC, and RAPGEF2. The expression levels of ROCK2, DOCK4, ITGA1, APC, and RAPGEF2 can be compared to reference expression levels using various methods. These reference levels can be determined using expression levels of a reference based on cancer samples from all cancer patients. Alternatively, it can be based on an internal reference such as a gene that is expressed in all cells. In some embodiments, the reference is a gene expressed in cancer cells at a higher level than any biomarker. Any comparison can be performed using the fold change or the absolute difference between the expression levels to be compared.

In certain embodiments of the fifth aspect, the cancer sample comprises a biopsy of a primary cancer tumor. In some embodiments, the primary cancer tumor is breast, pancreatic, ovarian, lung, head and neck, or colorectal.

As used herein, the term "primary tumor" or "primary cancer" or "primary cancer tumor" can be used interchangeably and refer to the original, or first, tumor or cancer in the body of the patient. A primary tumor is a tumor growing at the anatomical site where tumor progression began and proceeded to yield a cancerous mass. Cancer cells from a primary tumor may spread (i.e., metastasize) to other parts of the body and form new, or secondary, tumors. Secondary tumors are the same type of cancer as the primary tumor.

As used herein, the term "metastasis" refers to the spread of cancer cells from its original, primary site to another, secondary part of the body. Metastasis attributes to the most life-threatening aspect of cancer, accounting for approximately 90% of human cancer related deaths. Metastasis is a complex process and depends on detachment of malignant cells from a primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In certain embodiments, the term "metastasis" can refer to "distant metastasis" which relates to a metastasis which is remote from the primary tumor and the regional lymph node system.

As used herein, cancer cell "invasion" refers to the ability of cells to become motile and to navigate through the extracellular matrix within a tissue or to infiltrate neighboring tissues. In cancer, cell invasion can lead to metastasis (i.e., the development of tumors in secondary locations away from the primary tumor). Cell invasion is required for cancer cells to reach blood vessels, get into and out of circulation, and eventually colonize in distant organs. Experimentally, the ability of cancer cells to invade can be determined by studying their ability to navigate through a thin layer of extracellular matrix and make it to the other side of a porous membrane. A number of cell invasion assays are commercially available, these assays mimic the immediate surrounding of a cell, and can be used to determine cell invasion. Such cell invasion assays can include, but are not limited to, Boyden Chamber assay, chemotactic invasion assay, and variations thereof.

Based on the disclosure herein, the person of ordinary skill in the art can select an appropriate dosage for the combination of drugs comprising the at least two or more inhibitors. For example, in certain embodiments of the methods as described herein, a MEK inhibitor can be provided at a dosage in the range of about 0.005 mg to about 200 mg, for example, about 3 mg to about 50 mg, about 6 mg to about 50 mg, or about 10 mg to about 25 mg per administration. However, in certain embodiments, no more than about 250 mg, or no more than about 200 mg, no more than about 100 mg, no more than about 75 mg, no more than about 50 mg, no more than about 25 mg, no more than about 10 mg, no more than about 6 mg, or no more than about 3 mg of the MEK inhibitor is administered to a patient in any 24 hour period. For example, in certain embodiments of the methods as described herein, a p38 MAPK inhibitor can be provided at a dosage in the range of about 0.005 mg to about 200 mg, for example, about 3 mg to about 50 mg, about 6 mg to about 50 mg, or about 10 mg to about 25 mg per administration. However, in certain embodiments, no more than about 250 mg, or no more than about 200 mg, no more than about 100 mg, no more than about 75 mg, no more than about 50 mg, no more than about 25 mg, no more than about 10 mg, no more than about 6 mg, or no more than about 3 mg of the p38 MAPK inhibitor is administered to a patient in any 24 hour period. For example, in certain embodiments of the methods as described herein, a JNK inhibitor can be provided at a dosage in the range of about 0.005 mg to about 200 mg, for example, about 3 mg to about 50 mg, about 6 mg to about 50 mg, or about 10 mg to about 25 mg per administration. However, in certain embodiments, no more than about 250 mg, or no more than about 200 mg, no more than about 100 mg, no more than about 75 mg, no more than about 50 mg, no more than about 25 mg, no more than about 10 mg, no more than about 6 mg, or no more than about 3 mg of the JNK inhibitor is administered to a patient in any 24 hour period. For example, in certain embodiments of the methods as described herein, a MLK inhibitor can be provided at a dosage in the range of about 0.005 mg to about 200 mg, for example, about 3 mg to about 50 mg, about 6 mg to about 50 mg, or about 10 mg to about 25 mg per administration. However, in certain embodiments, no more than about 250 mg, or no more than about 200 mg, no more than about 100 mg, no more than about 75 mg, no more than about 50 mg, no more than about 25 mg, no more than about 10 mg, no more than about 6 mg, or no more than about 3 mg of the MLK inhibitor is administered to a patient in any 24 hour period. In certain embodiments, the composition comprises about 10 mg/kg of the p38 inhibitor, about 10 mg/kg of the JNK inhibitor, about 10 mg/kg of the MLK inhibitor, and about 5 mg/kg of the MEK inhibitor. In some embodiments, the concentration for SB203580 is 10 mg/kg/day, URMC-099 is 10 mg/kg/day, SP600125 is 10 mg/kg/day, and Trametinib is 0.5 mg/kg/day in the combination. The timing of the administration and the amounts of each of the two or more inhibitors can be selected based on disease severity, amount of necrosis, tumor volume, patient weight, age, or sex, and other considerations familiar to the person of ordinary skill in the art.

As a general matter, suitable dosage amounts and dosing regimens may be selected in accordance with a variety of factors, including one or more particular cancers being treated, the severity of the one or more cancers, the genetic profile, age, health, sex, diet, and/or weight of the subject, the route of administration alone or in combination with pharmacological considerations including the activity, efficacy, bioavailability, pharmacokinetic, and toxicological profiles of the particular compound employed, whether a drug delivery system is utilized and whether the drug is administered as part of a drug combination. Therefore, the dosing regimen to be employed may vary widely and may necessarily deviate from the dosage regimens set forth herein. In some embodiments, the composition comprising the at least two or more inhibitors of the MAPK pathway can be effective as a continuous therapy. For example, the continuous therapy can be administered for a day, a week, a month, a years, or multiples thereof.

In some embodiments, the method of treatment can be adjuvant therapy. Adjuvant therapy is any treatment given after primary therapy to increase the chance of long-term disease-free survival. Primary therapy is the main treatment used to reduce or eliminate the cancer. Primary therapy can typically include surgery (physical removal of the tumor, and/or a small amount of normal tissue around the tumor). During the surgery, one or more nearby lymph nodes can also be removed to see if cancer cells have spread to the lymphatic system. In certain embodiments, primary therapy can also include radiation therapy, chemotherapy, immunotherapy, or combinations thereof. In certain embodiments, the combination of at least two or more MAPK inhibitors is administered as an adjuvant therapy for at least 3 days, 5 days, 7 days, 10 days, 14 days, 20 days, 21 days, 24 days, 28 days, or more and any derivable range therein, after administration of a primary therapy.

In some embodiments, the method of treatment can be neoadjuvant therapy. Neoadjuvant therapy is treatment given before a primary therapy. A patient may receive neoadjuvant therapy according to the compositions and methods disclosed herein to prevent metastasis of a tumor, and/or sensitize the tumor to a primary therapy (for example, radiation therapy, chemotherapy, immunotherapy, or combinations thereof). In some embodiments, neoadjuvant therapy is combined with radiation therapy, chemotherapy, immunotherapy, or combinations thereof. In certain embodiments, neoadjuvant therapy combined with radiation therapy, chemotherapy, immunotherapy, or combinations thereof can be used to prevent metastasis of a tumor and to shrink the tumor before a surgery to remove the tumor. In certain embodiments, the combination of at least two or more MAPK inhibitors is administered as a neoadjuvant therapy at least 3 days, 5 days, 7 days, 10 days, 14 days, 20 days, 21 days, 24 days, 28 days, or more and any derivable range therein, before administration of a primary therapy.

In some embodiments, the methods of treatment further comprise administering to the patient one or more of a chemotherapy, a radiation therapy, and an immunotherapy. In certain embodiments, the method further comprises surgical removal of the primary cancer.

In certain embodiments, a chemotherapy can include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant thereof.

In certain embodiments, a radiation therapy is used. Radiation therapy (also known as radiotherapy) uses high doses of radiation to kill cancer cells and shrink tumors. Dosage ranges for X-rays can range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. Different routes of administration of radiation therapy contemplated herein are familiar to the person of ordinary skill in the art.

In some embodiments, immunotherapies can also be used to treat the cancer. Immunotherapy typically refers to the use of immune effector cells and/or molecules to target and destroy cancer cells. An immune effector molecule may be, for example, an antibody specific for some marker on the surface of a tumor cell. The antibody alone may serve as an effector of therapy or it may recruit other cells (e.g., immune cells) to effect cancer cell killing The antibody also may be conjugated to a drug and/or toxin (e.g., a chemotherapeutic, a radionuclide, a ricin A chain, a cholera toxin, a pertussis toxin, etc.) and serve merely as a targeting agent. Alternatively, the effector may be an immune effector cell, such as a lymphocyte carrying a surface molecule that interacts, either directly or indirectly, with a tumor cell target. Various effector cells include cytotoxic T cells and NK cells.

In some embodiments, surgery can be used to treat the cancer. Surgery can include resection of all or part of cancerous tissue. Tumor resection refers to physical removal, excision, and/or destruction of at least part of a tumor. In addition to tumor resection, treatment by surgery includes laser surgery, cryosurgery, electrosurgery, and microscopically controlled surgery (Mohs' surgery). It is further contemplated that the treatment methods described herein may be used in conjunction with removal of superficial cancers, precancers, or incidental amounts of normal tissue.

In some embodiments, the methods and compositions are effective at treating all types of cancers including solid cancerous tumors and hematological cancers. In certain non-limiting embodiments, the patient has a primary cancer selected from the group consisting of Acute Lymphoblastic Leukemia (ALL), Acute Myeloid Leukemia (AML), Adrenocortical Carcinoma, Kaposi Sarcoma (Soft Tissue Sarcoma), AIDS-Related Lymphoma, Primary CNS Lymphoma, Anal Cancer, Appendix Cancer, Astrocytomas, Brain Cancer, Atypical Teratoid/Rhabdoid Tumor, Basal Cell Carcinoma of the Skin, Bile Duct Cancer, Bladder Cancer, Bone Cancer (including Ewing Sarcoma and Osteosarcoma and Malignant Fibrous Histiocytoma), Breast Cancer, Bronchial Tumors, Burkitt Lymphoma, Non-Hodgkin Lymphoma, Carcinoid Tumor (Gastrointestinal), Cardiac (Heart) Tumors, Cervical Cancer, Cholangiocarcinoma, Chordoma, Chronic Lymphocytic Leukemia (CLL), Chronic Myelogenous Leukemia (CML), Colorectal Cancer, Craniopharyngioma, Cutaneous T-Cell Lymphoma, Ductal Carcinoma In Situ (DCIS), Endometrial Cancer (Uterine Cancer), Esophageal Cancer, Esthesioneuroblastoma (Head and Neck Cancer), Extragonadal Germ Cell Tumor, Eye Cancer, Intraocular Melanoma, Retinoblastoma, Fallopian Tube Cancer, Gallbladder Cancer, Gastric (Stomach) Cancer, Gastrointestinal Stromal Tumors (GIST), Germ Cell Tumors, Testicular Cancer, Gestational Trophoblastic Disease, Hairy Cell Leukemia, Hodgkin Lymphoma, Hypopharyngeal Cancer, Islet Cell Tumors, Pancreatic Neuroendocrine Tumors, Kidney (Renal Cell) Cancer, Langerhans Cell Histiocytosis, Laryngeal Cancer, Leukemia, Lip and Oral Cavity Cancer, Liver Cancer, Lymphoma, Melanoma, Merkel Cell Carcinoma (Skin Cancer), Mesothelioma, Multiple Myeloma/Plasma Cell Neoplasms, Mycosis Fungoides, Myelodysplastic Syndromes, Myelodysplastic/Myeloproliferative Neoplasms, Nasal Cavity and Paranasal Sinus Cancer, Nasopharyngeal Cancer, Neuroblastoma, Non-Small Cell Lung Cancer, Oral Cancer, Oropharyngeal Cancer, Ovarian Cancer, Pancreatic Cancer, Paraganglioma, Parathyroid Cancer, Penile Cancer, Prostate Cancer, Rhabdomyosarcoma, Salivary Gland Cancer, Sarcoma, Uterine Sarcoma, Small Cell Lung Cancer, Small Intestine Cancer, Sèzary Syndrome, Throat Cancer, Thymoma, Thyroid Cancer, Urethral Cancer, Vaginal Cancer, Wilms Tumor, and metastatic forms thereof. In an embodiment, the cancer is breast cancer, in particular, triple-negative breast cancer (TNBC).

In some embodiments of the methods of treatment as disclosed herein, the patient has a cancer with decreased RKIP (PEBP1) expression levels compared to a control. In an embodiment, the patient has a cancer with decreased RKIP protein levels compared to a control. In certain embodiments, the patient has a cancer with an increased expression of one or more of APC, DOCK4, ADAMS, DAB2, DOCK10, FLNA, FN1, HDAC4, MCAF1, RAPGEF2, and ROBO1 genes when compared to expression levels of the same genes in a control sample. In some embodiments, the patient has a cancer with an increased expression of ROCK2, DOCK4, ITGA1, APC, and RAPGEF2 when compared to expression levels of the same genes in a control sample.

As used herein, the terms "control" or "normalized sample" can be based on one or more cancer samples that are not from the patient being tested. For example, TG-high refers to expression levels above the median expression level for all cancer samples. In certain embodiments, a cancer cell or tumor may be determined to have a relative increased or decreased level of expression by comparing the expression levels of genes in the sample from the patient to the median expression levels of these genes across all cancer patients.

As used herein, the terms "increased expression," "overexpressed," or "up-regulated" can be used interchangeably and refer to a gene or gene product that is transcribed or translated at a detectably greater level, usually in a cancer cell, in comparison to a non-cancer cell or a cancer cell that is not associated with an increased risk of metastasis or decreased overall patient survival. For example, for the survival analyses, disclosed herein, "survival" and "survminer" R packages were used, and TCGA breast cancer patients were separated into two groups: target-gene high expressors (TG-high) and target-gene low expressors (TG-low) based on the expression of ROCK2, DOCK4, ITGA1, APC, and RAPGEF6. If a patient sample falls above the median for all 5 genes, that patient is deemed TG-high. If a patient sample falls below the median for all 5 genes, that patient is deemed TG-low. Survival probability with respect to time (in months) can be plotted in a Kaplan-Meier curve and statistical significance can be determined using a logrank test.

Increased expression can also include overexpression due to transcription, post transcriptional processing, translation, post-translational processing, cellular localization, and/or RNA and protein stability, as compared to a non-cancer cell or a cancer cell that is not associated with an increased risk of metastasis or decreased overall patient survival. Overexpression can be detected using conventional techniques for detecting mRNA (i.e., RT-PCR, PCR, hybridization, next generation sequencing, or combinations thereof) or proteins (i.e., ELISA, immunohistochemical techniques, mass spectroscopy, RIA, FACS, dot blot, Western blot, or combinations thereof). Increased expression can be an increase of 10%, 20%, 30%, 40%, 50%, 60%, 70%, 80%, 90%, or more (or any range derivable therein) in comparison to a normal cell or cancer cell that is not associated with an increased risk of metastasis or decreased overall patient survival. In some embodiments, increased expression can be an increase that is 1.5-fold, 2-fold, 3-fold, 4-fold 5, 6, 7, 8, 9, 10, or 15-fold or more greater (or any range derivable therein) in comparison to a non-cancer cell or cancer cell that is not associated with an increased risk of metastasis or decreased overall patient survival. The comparison may be a direct comparison where the expression level of a control is measured at the same time as the test sample or it may be a level of expression that is determined from a previously evaluated sample or an average of levels of expression of previously evaluated sample(s). In certain embodiments, a patient may be determined to have a relatively increased or decreased level of expression by comparing the expression levels of genes in the cancer sample taken from the patient to the median expression levels of these genes across all cancer patients.

Pharmaceutical Compositions and Dosage Forms

As used herein the term "a therapeutically effective" amount refers to an amount of the combination of drugs that may prevent or inhibit (i.e., slow to some extent and particularly stop) cancer cell invasion or infiltration; prevent or inhibit (i.e., slow to some extent and particularly stop) cancer cell metastasis; and/or relieve to some extent one or more of the symptoms associated with cancer. In certain embodiments, the composition and methods described herein have the potential to prevent recurrence with continued treatment. In some embodiments, the therapeutically effective amount of the combination of drugs, when combined with a radiation therapy, a chemotherapy, or an immunotherapy (or combinations thereof), may prevent cancer invasion or metastasis, prevent growth/proliferation and/or kill existing cancer cells, and/or it may be cytostatic and/or cytotoxic. For cancer therapy, efficacy in vivo can, for example, be measured by assessing the duration of overall patient survival, time to disease progression (TTP), the response rates (RR), duration of response, and/or quality of life.

The compositions as disclosed herein may further contain other therapeutically valuable substances for different applications, like solubilizers, stabilizers, tonicity enhancing agents, buffers and/or preservatives. The pharmaceutical compositions and dosage forms can include at least two or more inhibitors of the MAPK pathway, or pharmaceutically acceptable salts or derivatives thereof.

Depending on the dosing regimen, each administration of a pharmaceutical composition including at least two or more inhibitors of the MAPK pathway can be performed, for example, by giving a patient a single unit dose (e.g., pill, capsule, other oral dosage form) or injection, multiple unit doses or injections, or continuously (e.g., intravenous or slow-release patch), or otherwise as disclosed herein. For example, a pharmaceutical composition including the at least two or more MAPK inhibitors can be formulated for oral, transdermal, intraspinal, intrathecal, inhalation, subcutaneous, intravenous, intramuscular, or transmucosal administration, or for administration via osmotic pump, microcapsule, implant, or suspension. It is further contemplated that the at least two or more MAPK inhibitors can be formulated for different routes of administration at the same time or within the same administration. Precise amounts of the therapeutically effective compositions also depend on the judgment of the practitioner and are specific to each patient. Factors affecting the dose to be administered to a patient in need thereof include the physical and/or clinical state of the patient, the route of administration, the intended goal of treatment (e.g., alleviation of symptoms versus cure) and the potency, stability, and toxicity of the particular therapeutic substance.

The invention will be further described in the following examples, which do not limit the scope of the invention described in the claims.

EXAMPLES

The Examples that follow are illustrative of specific embodiments of the invention, and various uses thereof. They are set forth for explanatory purposes only and are not taken as limiting the invention.

Metastatic TNBC is a fatal disease with a 5-year survival rate of only 24%. Raf Kinase Inhibitory Protein (RKIP) is a member of the evolutionarily-conserved PEBP family. RKIP is both a regulator and a target of kinases. In cell culture, it modulates primarily the Raf-Mek-Erk cascade, but has also been implicated in NFκB and GPCR signaling pathways. RKIP regulates spindle checkpoint. RKIP can potentiate chemosensitivity. RKIP expression is lost or decreased in virtually all metastatic cancers. RKIP inhibits metastasis experimentally and is associated with metastasis clinically.

Methods

MIB-MS Method for isolating active kinases: Multiplexed Inhibitor Beads/Mass Spec (MIB-MS) method for investigating kinome activity: Multiple kinase inhibitors conjugated to beads; Pull-down active kinases; Identify via mass spec. (BoM1 cells: Bone-tropic derivative of MDA-MB-231 cell line).

Cell lines: MDA-MB-231 (MB231), MDA-MB-436 (MB436), MCF10A, 184A1, and 293T cells were received from American Type Culture Collection (ATCC®). E0771-LMB (LMB) cells were received from Robin Anderson (Johnstone et al., 2015). M6C cells were received from Jeffrey Green (Holzer et al., 2003). MDA-MB-231-BM1 (BM1) cells were obtained from Andy Minn, but they were originally generated by Massague and colleagues (Kang et al., 2003). BM1, MB436, LMB, and M6C cells were cultured in DMEM media with 10% fetal bovine serum (FBS), penicillin (50 U/ml), and streptomycin (50 ug/ml). MCF10A and 184A1 cells were grown in DMEM/F-12 (50/50) with 10% FBS and penicillin-streptomycin. The cells were used in experiments within 15 passages after their arrival in the laboratory.

Small molecule inhibitors: For in vitro and in vivo studies, JNK inhibitor SP600125, MEK inhibitor Trametinib (GSK1120212), and MLK inhibitor URMC-099 were purchased from APExBIO (Cat. Nos. A4604, A3018, and B4877, respectively). p38 inhibitor SB203580 was purchased from Selleckchem (Cat. No. S1076) for the in vitro experiments. For in vivo studies, water soluble SB203580 hydrochloride was purchased from APExBIO (Cat. No. B1285).

Signaling studies in vitro: In order to investigate the changes in stress kinase signaling upon stress in the presence of RKIP, or small molecule inhibitors of the MAPKs, cells were plated at sub-confluence. Once they reached roughly 70% confluence, they were starved overnight (16-24 hours) in serum-free media, and then induced with either anisomycin (Sigma-Aldrich, Cat. No. A9789) at 25 ng/ml or 100 ng/ml final concentration, or by 10% serum for 30 minutes to activate MAPK pathways. In studies with small molecule inhibitors of the MAPK pathway, all inhibitors were re-suspended in DMSO and used at indicated concentrations. The cells were pre-treated with the inhibitors in serum-free media for 30 minutes after overnight starvation, immediately before induction with anisomycin or serum for 30 minutes. In this case, the inducing agent was directly added to the pre-treatment media that already had the inhibitors, or the pre-treatment media was replaced by fresh media containing the inducer and the inhibitors. This was to ensure the inhibitors were present during induction of the MAPK pathways. Upon induction for 30 minutes, the cells were washed three time with cold PBS and immediately lysed in RIPA buffer for protein collection.

Protein isolation and western blots: Cultured cells were washed with cold PBS and lysed in RIPA buffer with protease inhibitors (Millipore Sigma, Cat. No. 539134) and phosphatase inhibitors (GoldBio, Cat. No. GB-450). Tumor samples were snap-frozen in liquid nitrogen, pulverized, and lysed in RKIP buffer with protease and phosphatase inhibitors. All samples were sonicated 3×10 seconds at 35% power and centrifuged at max speed for 15 minutes at 4° C. Supernatant was collected and the protein concentration measured using the Bradford assay. All samples were boiled in 6×Laemmli buffer immediately after protein concentration measurement.

For western blots, equal amounts of protein, ranging from 10 μg to 50 μg, across all samples were used. Blots were blocked for 1 hour at ambient temperature with either Odyssey® Blocking Buffer (LI-COR Biosciences, Cat. No. 927-40010, diluted 1:1 with PBS) or with 5% FBS in TBS-T. Then, blots were incubated with primary antibodies at 4° C. overnight, and with secondary antibodies at ambient temperature for 1 hour. Finally, blots were treated with ECL reagent (Pierce ECL Western Blotting Substrate, Thermo Scientific, Cat. No. 32106) when HRP-conjugated secondary antibodies were used and developed under the Chemiluminescence channel of the LI-COR® Fc Imaging System. Blots with fluorescent secondary antibodies were imaged under 700 nm or 800 nm channels of LI-COR® Fc.

Primary antibodies used:
a. Phospho-RSK2 (Ser227) (Cell Signaling, 3556)
b. Phospho-ATF2 (Thr71) (Cell Signaling, 9221, no longer available)
c. Phospho-SEK1/MKK4 (Ser257/Thr261) (Cell Signaling, 9156)
d. Phospho-TAOK3 (Ser177)+Phospho TAOK2 (Ser181)+Phospho-TAOK1 (Ser181) (Abcam, ab124841)
e. MLK3 (Cell Signaling, 2817)
f. Phopsho-p44/42 MAPK (ERK1/2)(Thr202/Tyr204) (Cell Signaling, 9101)
g. Phospho-MSK1 (Thr581) (Cell Signaling, 9595)
h. Phospho-SAPK/JNK (Thr183/Tyr185) (Cell Signaling, 9251)
i. p44/42 MAPK (ERK1/2) (Cell Signaling, 9107)
j. SAPK/JNK (Cell Signaling, 9252)
k. Phospho-p38 MAPK (Thr180/Tyr182) (Cell Signaling, 4511)
l. Phospho-AKT1 (S129) (Abcam, ab133458)
m. Phospho-MKK3 (Ser189)/MKK6 (Ser207) (Cell Signaling, 12280)
n. Phospho-c-Jun (Ser73) (Cell Signaling, 3270)
o. Phospho-p70 S6 Kinase (Thr389) (Cell Signaling, 9205)
p. MLK3 (Abcam, ab51068)
q. MLK3 (Santa Cruz, sc-166639)
r. Phopsho-MLK3 (T277/5281) (Abcam, ab191530)
s. DOCK4 (Santa Cruz, sc-100718)
t. Casein Kinase 2\textbeta (Santa Cruz, sc-12739)
u. Casein Kinase 2\textalpha (Santa Cruz, sc-9030)
v. TAOK1 (Abcam, ab197891)
w. TAOK1/PSK2 (Santa Cruz, sc-136094)
x. TAOK2 (Santa Cruz, sc-47447)
y. TAOK3 (Abcam, ab150388)
z. alpha-Tubulin (Santa Cruz, sc-8035).

Secondary antibodies used:
a. Goat anti-Mouse IgG (LI-COR, IRDye® 800CW, 926-32210)
b. Goat anti-Mouse IgM (LI-COR, IRDye® 800CW, 926-32280)
c. Goat anti-Rabbit IgG (LI-COR, IRDye® 680RD, 926-68071)
d. Goat anti-Rabbit IgG, HRP conjugate (EMD Millipore, AP187P)
e. Goat anti-Mouse IgM, HRP conjugate (Invitrogen, 31440)
f. Goat anti-Mouse IgG, HRP conjugate (Sigma Aldrich, A4416).

Transient transfection: Prior to transfection, the cells were plated in 6-well plates and grown to ~70% confluence. siRNA vectors were used at a final concentration of 50 nM per well of cells. The vectors were incubated with 10 μl of Lipofectamine 3000 (Invitrogen, Cat. No. L3000-015) in OPTI-MEM media (Gibco, Cat. No. 31985062) for 15-30 minutes. The DNA-lipid complex was then added onto the cells in a drop-wise fashion. Cells were incubated with the siRNAs for at least 24 hours before harvesting for experimental use. All experiments were performed 24-72 hours post-transfection. All siRNA constructs were purchased from Dharmacon: Individual siGENOME human TAOK1 siRNA, Dharmacon, D-004846-02-0005); Individual siGENOME human TAOK2 siRNA, Dharmacon, D-004171-13-0005); Individual siGENOME human TAOK3 siRNA, Dharmacon, D-004844-02-0005); and siGENOME Non-Targeting siRNA Pool \#1, Dharmacon, D-001206-13-05).

Stable Lenti-viral cell line generation: 293T cells were plated in T-75 plates and were grown to ~70% confluence prior to transfection. 1 hour prior to transfection, the media was replaced with fresh media. Lentiviral vectors were incubated with 3rd generation viral packaging vectors (pCMV-VSV-G, pMDLg/pRRE, pRSV-Rev) and LT-1 (Mirus, Cat. No. MIR-2305) in OPTI-MEM media for 30 minutes as described by the provider's instructions. This transfection mix was then added onto the 293T cells in a drop-wise fashion. Virus-containing media was collected 24-48 hours after transfection. Cellular content and debris were removed by centrifugation, and the supernatant was filtered through 0.45 μm PES syringe (Millex, Cat. No. SLHP033RS) to remove any remaining cells in the media. Polybrene was added to the media at the final concentration of 8 ng/ml to facilitate viral transduction of the target cell line. The target cell lines were transduced with the virus-containing media for 24-48 hours. At the end of the transduction period, cells were washed, trypsinized, and re-plated for selection. Transduced cells were exposed to high concentration antibiotic selection (3 μg/ml puromycin) up to 2 weeks (approximately 3 passages). All lentiviral procedures were carried out following Biosafety Level 3 (BSL3) practices in BSL2 tissue culture hoods according to institutional biosafety rules.

Boyden Chamber Invasion Assay: Each Boyden chamber membrane (Fisher Scientific, Cat. No. 353097) was coated with a thin layer of BME (200 μl of 0.25 mg/ml stock, or total of 50 μg of BME per membrane) and incubated at 37° C. for 1 hour. Cells were trypsinized and centrifuged at 500×g for 5 minutes followed by two rounds of PBS washes to remove remaining serum-containing media. Then, the cells were resuspended in serum-free media and diluted to the desired concentration for plating onto the Boyden chambers. Each Boyden chamber received 20,000-100,000 cells in 300 µl serum-free media, depending on the cell line. 10% serum was used as the chemoattractant for these assays. For the experiments testing the effect of MAPK inhibitors on invasion, the cells were resuspended in drug-containing serum-free media immediately. After 16-24 hours, the membranes were stained with Calcein AM (Fisher Scientific, Cat. No. 354217) for 1 hour at 37° C. in the dark to stain for live cells. Cells that are in the top chamber were removed from the membrane with a wet cotton swab. Cells in the bottom chamber were dissociated from the membrane by incubating in cell dissociation buffer (Trevigen, Cultrex®, Cat. No. 3455-096-05) in a shaker at 37° C. for 1 hour. Calcein AM signal was measured in Perkin Elmer Victor X3 plate reader as a read-out of invaded cells.

High-throughput chemotactic invasion assays: For testing anti-invasive drug combinations, IncuCyte® ClearView 96-Well Chemotaxis plates (Essen BioScience) were used. 2000 cells per well were embedded in 2 mg/ml BME and plated onto the chemotaxis plate following the manufacturer's instructions. Media containing 2% FBS was used in both top and bottom chambers to maintain cell viability over 72 hours or more. 200 ng/ml human EGF (Bio-Techne, 236-EG-01M) was used as the chemotactic agent in the bottom chamber, and the control wells only had the vehicle for the chemotactic agent.

This assay is more accurate when nuclear-labeled cells are used. Therefore, BM1-mKate2 (nuclear red) cells were generated using IncuCyte® NucLight Red Lentivirus Reagent (Essen BioScience, Cat. No. 4478) following the manufacturer's instructions. After transduction, cells with the highest nuclear red signal intensity (top 25%) were sorted by FACS.

The chemotaxis module in IncuCyte® can accurately count the number of cell in the top chamber and the bottom chamber of the ClearView plates separately. Invasive capability of the cells in the presence of various small molecule inhibitors was measured as the percentage of cells that moved to the bottom chamber over the period of 72 hours. The formula used for this calculation is (number of cells in the bottom chamber)/(number of cells in the bottom chamber+number of cells in the top chamber)×100. The total number of cells in the top and bottom chambers is used as a readout of proliferation, which was important for determining drug combinations that blocked invasion without affecting growth properties of the cells.

Proliferation Assays: For proliferation assays, 1,000-20,000 cells (depending on the cell line) were plated in 96-well plates and quantified over 5 days in IncuCyte by measuring confluence in Phase-Contrast images taken every 4 hours. For experiments testing the effect of MAPK inhibitors on proliferation, the cells were plated in 100 µl per well and allowed to adhere overnight. Then, 100 µl growth media containing 2×drug was added directly on top of the initial media.

3D Cultures: For 3D proliferation experiments, we used Cultrex® 3D Basement Membrane Matrix, Reduced Growth Factor (Trevigen, Cat. No. 3445-005-01, Lot No 37353J16, Lot concentration: 15.51 mg/ml, referred to as BME). For all experiments, the cells in growth media were mixed with BME at a final concentration of 2 mg/ml. For 3D proliferation assays, 100 µl of the cell/BME mixture was dispensed into each well of a 96-well plate. Upon solidification of BME, 100 µl of growth media was added on top of the solidified gel. For experiments where the cells were treated with inhibitors, the inhibitors were prepared in the growth media at 2× of their desired final concentration and added after the gel is solidified to assure 1×final concentration. The growth of the cells was monitored in IncuCyte® Zoom or S3 models for the indicated duration of time.

Scratch Wound assays: Migration assays are conducted using IncuCyte's "Scratch wound" module. 20,000-30,000 cells were plated on IncuCyte® ImageLock Plates (Essen BioScience, 4379). Once the cells reached 100% confluence, the wells were scratched with IncuCyte® WoundMaker (Essen BioScience, 4493) following the provider's instructions, washed with PBS twice, and supplied with fresh growth media. For experiments testing the effect of MAPK inhibitors on cell migration, fresh growth media containing the inhibitors at the desired final concentration was added onto the cells after the PBS washes. Wound-healing process was monitored over 72 hours in IncuCyte, and wound density was measured over time as a readout of cell migration.

RNA isolation and qRT-PCR: Cells were washed with cold PBS twice and lysed in TRI Reagent (Zymo Research, Cat. No. R2050-1-200). RNA was isolated using Direct-zol™ RNA MiniPrep (Zymo Research, Cat. No. R2052). 4 µg of total RNA from each sample was converted to cDNA using High Capacity cDNA Reverse Transcription Kit (Applied Biosystems, Cat. No. 4368813). Primer pairs used herein are listed in the Tables below.

TABLE 2

| Human primers: | | |
|---|---|---|
| Hs_PEBP1 Forward | GCTCTACACCTTGGTCCTGACA | (SEQ ID NO: 01) |
| Hs_PEBP1 Reverse | AATCGGAGAGGACTGTGCCACT | (SEQ ID NO: 02) |
| Hs_NFATC2 Forward | GATAGTGGGCAACACCAAAGTCC | (SEQ ID NO: 03) |
| Hs_NFATC2 Reverse | TCTCGCCTTTCCGCAGCTCAAT | (SEQ ID NO: 04) |
| Hs_ROCK1 Forward | GAAACAGTGTTCCATGCTAGACG | (SEQ ID NO: 05) |
| Hs_ROCK1 Reverse | GCCGCTTATTTGATTCCTGCTCC | (SEQ ID NO: 06) |
| Hs_ROCK2 Forward | TGCGGTCACAACTCCAAGCCTT | (SEQ ID NO: 07) |
| Hs_ROCK2 Reverse | CGTACAGGCAATGAAAGCCATCC | (SEQ ID NO: 08) |
| Hs_ADAM10 Forward | GAGGAGTGTACGTGTGCCAGTT | (SEQ ID NO: 09) |
| Hs_ADAM10 Reverse | GACCACTGAAGTGCCTACTCCA | (SEQ ID NO: 10) |

TABLE 2-continued

| Human primers: | |
| --- | --- |
| Hs_ADAM17 Forward | AACAGCGACTGCACGTTGAAGG (SEQ ID NO: 11) |
| Hs_ADAM17 Reverse | CTGTGCAGTAGGACACGCCTTT (SEQ ID NO: 12) |
| Hs_EPC1 Forward | CCAGACATGCAGTACCTCTACG (SEQ ID NO: 13) |
| Hs_EPC1 Reverse | GCTGTTTCTGCATGAGTGCCAG (SEQ ID NO: 14) |
| Hs_PIKFYVE Forward | CTGAGTGATGCTGTGTGGTCAAC (SEQ ID NO: 15) |
| Hs_PIKFYVE Reverse | CAAGGACTGACACAGGCACTAG (SEQ ID NO: 16) |
| Hs_DOCK4 Forward | GCATGTGGATGATTCCCTGCAG (SEQ ID NO: 17) |
| Hs_DOCK4 Reverse | GGAGGTGATGTAACACGACAGG (SEQ ID NO: 18) |
| Hs_DOCK5 Forward | GCTTCTGAGCAACATCCTGGAG (SEQ ID NO: 19) |
| Hs_DOCK5 Reverse | TCCTTCTCAGCAGCCGTTCCAT (SEQ ID NO: 20) |
| Hs_ARL13B Forward | GAACCAGTGGTCTGGCTGAGTT (SEQ ID NO: 21) |
| Hs_ARL13B Reverse | GTTTCAGGTGGCAGCCATCACT (SEQ ID NO: 22) |
| Hs_DDR2 Forward | AACGAGAGTGCCACCAATGGCT (SEQ ID NO: 23) |
| Hs_DDR2 Reverse | ACTCACTGGCTTCAGAGCGGAA (SEQ ID NO: 24) |
| Hs_ITGA1 Forward | CCGAAGAGGTACTTGTTGCAGC (SEQ ID NO: 25) |
| Hs_ITGA1 Reverse | GGCTTCCGTGAATGCCTCCTTT (SEQ ID NO: 26) |
| Hs_RAPGEF2 Forward | CTCGGATCAGTATCTTGCCACAG (SEQ ID NO: 27) |
| Hs_RAPGEF2 Reverse | AGGTTCCACTGACAGGCAATGC (SEQ ID NO: 28) |
| Hs_RAPGEF6 Forward | AGACAGATGAGGAGAAGTTCCAG (SEQ ID NO: 29) |
| Hs_RAPGEF6 Reverse | GACCTCATAGGCACTGGAGACA (SEQ ID NO: 30) |
| Hs_APC Forward | AGGCTGCATGAGAGCACTTGTG (SEQ ID NO: 31) |
| Hs_APC Reverse | CACACTTCCAACTTCTCGCAACG (SEQ ID NO: 32) |

TABLE 3

| Mouse primers: | |
| --- | --- |
| Mm_PEBP1 Forward | ACTCTACACCCTGGTCCTCACA (SEQ ID NO: 33) |
| Mm_PEBP1 Reverse | TGAGAGGACAGTGCCACTGCTA (SEQ ID NO: 34) |
| Mm_NFATC2 Forward | ACTTCACAGCGGAGTCCAAGGT (SEQ ID NO: 35) |
| Mm_NFATC2 Reverse | GGATGTGCTTGTTCCGATACTCG (SEQ ID NO: 36) |
| Mm_ROCK1 Forward | CACGCCTAACTGACAAGCACCA (SEQ ID NO: 37) |
| Mm_ROCK1 Reverse | CAGGTCAACATCTAGCATGGAAC (SEQ ID NO: 38) |
| Mm_ROCK2 Forward | GTGACCTCAAACAGTCTCAGCAG (SEQ ID NO: 39) |
| Mm_ROCK2 Reverse | GACAACGCTTCTGAGTTTCCTGC (SEQ ID NO: 40) |
| Mm_ADAM10 Forward | TGCACCTGTGCCAGCTCTGATG (SEQ ID NO: 41) |
| Mm_ADAM10 Reverse | GATAGTCCGACCACTGAACTGC (SEQ ID NO: 42) |
| Mm_ADAM17 Forward | TGTGAGCGGTGACCACGAGAAT (SEQ ID NO: 43) |
| Mm_ADAM17 Reverse | TTCATCCACCCTGGAGTTGCCA (SEQ ID NO: 44) |
| Mm_EPC1 Forward | CTGCCAGGCTTCAGTGCTAAAG (SEQ ID NO: 45) |
| Mm_EPC1 Reverse | ACTGACAGCCTGCTTTCCTACG (SEQ ID NO: 46) |

TABLE 3-continued

| Mouse primers: | | |
|---|---|---|
| Mm_PIKFYVE Forward | TCTTCTGCCCAGTCCAGCAATG | (SEQ ID NO: 47) |
| Mm_PIKFYVE Reverse | ACAGAACATGCTCGGACACTGG | (SEQ ID NO: 48) |
| Mm_DOCK4 Forward | GATAGGAGAGGTGGATGGCAAG | (SEQ ID NO: 49) |
| Mm_DOCK4 Reverse | CGCCTTGAGATGCAGATCGTAG | (SEQ ID NO: 50) |
| Mm_DOCK5 Forward | GAGCCGACAGTCTCCTCACATT | (SEQ ID NO: 51) |
| Mm_DOCK5 Reverse | CTGCCTGGTTTTGAAGGTGCTG | (SEQ ID NO: 52) |
| Mm_ARL13B Forward | ACCAGTGGTCTGGCTGAGATTG | (SEQ ID NO: 53) |
| Mm_ARL13B Reverse | CATCACTGTCCTTCTCCACGGT | (SEQ ID NO: 54) |
| Mm_DDR2 Forward | TCATCCTGTGGAGGCAGTTCTG | (SEQ ID NO: 55) |
| Mm_DDR2 Reverse | CTGTTCACTTGGTGATGAGGAGC | (SEQ ID NO: 56) |
| Mm_ITGA1 Forward | GGCAGTGGCAAGACCATAAGGA | (SEQ ID NO: 57) |
| Mm_ITGA1 Reverse | CATCTCTCCGTGGATAGACTGG | (SEQ ID NO: 58) |
| Mm_RAPGEF2 Forward | GCCGAATGGCATCAGTCAACATG | (SEQ ID NO: 59) |
| Mm_RAPGEF2 Reverse | CAACATCCAGCACTGTGGCGTT | (SEQ ID NO: 60) |
| Mm_RAPGEF6 Forward | ACAGAGTGAGCCAGGTGCTTCA | (SEQ ID NO: 61) |
| Mm_RAPGEF6 Reverse | CACTCACTTCCTCAGTTGGTCC | (SEQ ID NO: 62) |
| Mm_APC Forward | GTGGACTGTGAGATGTATGGGC | (SEQ ID NO: 63) |
| Mm_APC Reverse | CACAAGTGCTCTCATGCAGCCT | (SEQ ID NO: 64) |

CHIP assays: BM1 cells were crosslinked with 10% formaldehyde for 10 minutes and quenched with 0.125 mM glycine for 3 minutes. Cells were then lysed for sonication at 80% output for 4×10 seconds with a 10 second pause in between each cycle. The lysate was pre-cleared with IgG (Santa Cruz, sc-2028) for 1 hour at 4° C. and the supernatant was precipitated with antibodies against BACH1 (AF5776, R&D System), or IgG (normal mouse IgG, Santa Cruz, sc-2025) overnight at 4° C. Primers for ChIP quantitative RT-PCR are listed in Table 4 below.

TABLE 4

| Human primers used for the CHIP assay quantitative RT-PCR | | |
|---|---|---|
| Hs_ROCK1 Forward | CAGCCTCACTCTCCCATTTT | (SEQ ID NO: 65) |
| Hs_ROCK1 Reverse | TCCAGCCTTTCCTCTGCTAA | (SEQ ID NO: 66) |
| Hs_PIKFYVE Forward | CTGGACTCCTTCTGCCTGAG | (SEQ ID NO: 67) |
| Hs_PIKFYVE Reverse | AAGACTCCGCCCTCTGTTTT | (SEQ ID NO: 68) |
| Hs_DOCK4 (upstream) Forward | ATTTGCCTGGAGTGGAAGTG | (SEQ ID NO: 69) |
| Hs_DOCK4 (upstream) Reverse | CTGTATCCAGGGGGATGATG | (SEQ ID NO: 70) |
| Hs_DOCK4 (downstream) Forward | TAAGCCCTAGCTCCTGGACA | (SEQ ID NO: 71) |
| Hs_DOCK4 (downstream) Reverse | AGGGGTCACAAACACTCCTG | (SEQ ID NO: 72) |
| Hs_RAPGEF2 Forward | AAAAATGCCAAGAAGGGGTTA | (SEQ ID NO: 73) |
| Hs_RAPGEF2 Reverse | CACTCATCTAGACAGACCCCTGA | (SEQ ID NO: 74) |
| Hs_RAPGEF6 Forward | CGCCACAGTTCATTCACACT | (SEQ ID NO: 75) |
| Hs_RAPGEF6 Reverse | GCGAAGGGTTGTTTGCTAGA | (SEQ ID NO: 76) |

Mouse Studies: Mice were procured and housed by the Animal Resources Center and handled according to the Institutional Animal Care and Use Committee at the University of Chicago. Athymic nude mice were purchased from Harlan Sprague Dawley and C57B$^{1/6}$ mice were purchased from the Jackson Laboratories. C3-1-TAg-REAR mice were received from Jeffrey Green and maintained in-house.

For primary tumor growth experiments, 2×10$^6$ BM1 cells, 5×10$^5$ LMB cells, or 1×10$^6$ M6C cells were injected orthotopically near the mammary fat pad of athymic nude, C57B1/6, or C3-1-TAg-REAR mice, respectively. Tumor growth was monitored over time by caliper measurements of the width and length of tumors. Tumor volumes were calculated with the formula:

$$\text{volume} = \frac{\pi}{6} \times width^2 \times \text{length}$$

The mice were sacrificed when the tumors reached approximately 1 cm$^3$.

For metastasis assays, 1×10$^5$ luciferase-expressing BM1 cells (BM1-luc) were injected into the left ventricle of the heart to allow for systemic distribution of the bone-tropic tumor cells. 5×10$^5$ LMB cells and 1×10$^6$ M6C cells were injected into the tail vein. Mice were monitored for 3-6 weeks (depending on the model) for tumor development. At the earliest sign of respiratory problems or paralysis of the limbs, the experiment was ended, and the mice were euthanized Tumor burden was measured at the end of the experiment via Xenogen IVIS® 200 Imaging System (PerkinElmer) for BM1-luc tumors. For LMB and M6C tumors, tumor burden was measured by counting overt surface metastases in the lungs after perfusion and formalin fixation, as well as counting tumors in cross-sections of the lungs after H&E staining (described below).

For the in vivo studies involving MAPK inhibitors and the 4-drug MAPKi combination treatment, small molecule inhibitors were resuspended under sterile conditions. Since not all of the inhibitors were water-soluble, all inhibitors were initially resuspended in DMSO at the volumes that will result in less than 5% final DMSO concentration. p38 inhibitor SB203580 and MLK inhibitor URMC-099 were further diluted to the desired concentration with 50% PEG-400 (Sigma, Cat. No. 91893)+50% saline. JNK inhibitor SP600125 and MEK inhibitor Trametinib were diluted in corn oil (Sigma, Cat. No. C8267). For the 4-drug combinatorial treatment, all inhibitors were dissolved in their own solvent at 4×higher concentration then the desired final concentration. Then, SB203580 and URMC-099 were mixed at a 1:1 ratio, reducing the concentration for each drug down to 2×. Similarly, SP600125 and Trametinib were mixed at a 1:1 ratio. These dual combination solutions were then filtered through 0.22 μm PES filter syringes to assure sterility. Each mouse received 50 μl of each dual combination on the same day, resulting in a total of 100 μl of drug mix (2 injections per mouse) with each drug at their desired 1×final concentration. Final concentration for SB203580, URMC-099, SP600125, or Trametinib in the 4-drug MAPKi combination was 10 mg/kg/day, 10 mg/kg/day, 10 mg/kg/day, or 0.5 mg/kg/day, respectively. All injections were intraperitoneal.

For the tumor growth experiments with the MAPK inhibitors, tumors were allowed to reach the size 50-100 mm$^3$ size before the MAPKi treatment began. Then, the mice were treated with the respective MAPKi treatment (or the control) for up to 3 weeks. Tumor size was monitored twice a week with a caliper. For the metastasis assays, the tumor cells were treated with the 4-drug MAPKi combination at the in vitro doses for 24 hours prior to injections to allow for anti-metastatic reprogramming of the cells. Homing to metastatic tissues upon intracardiac or tail vein injections can take up to 48 hours. To ensure that the reprogrammed tumor cells do not revert back to their untreated state in the circulation, we pre-treated the mice with the MAPKi combination 2-6 hours before tumor cell inoculation as well. After the inoculation, the mice were treated with the inhibitors daily for up to 3 weeks until the experimental endpoints discussed above were reached.

Histology: Tumor tissues were fixed in 10% formalin upon dissection for 72 hours and then transferred into 70% Ethanol for long-term storage. Mouse lungs were perfused with PBS before formalin fixation step to allow for tissue expansion and high-quality histological analysis. Fixed tissues were embedded in paraffin and sliced into 5 μm sections prior to hematoxylin & eosin (H&E) staining All tissue processing and staining for this body of work was performed by the University of Chicago Human Tissue Resource Center. For the detection of tissue morphology as well as tumor populations within the lung, lung sections were deparaffinized, immersed in hematoxylin, rinsed in warm distilled water, and treated with eosin. Stained slides were scanned at 10× on a Nikon Eclipse Ti2 Inverted Microscope System.

MIB-MS analysis: Multiplexed inhibitor beads—mass spectrometry analysis on BM1-VC and BM1-RKIP tumors was conducted as previously described. (Duncan et al., 2012). Tumors were grown in athymic nude mice as described previously. Once the tumors reached the size of ~300 mm$^3$ they were isolated, flash-frozen in liquid nitrogen, and shipped to the Johnson Laboratories in Chapel Hill. Preparation of the lysate for the MIB-MS analysis, and the mass spectrometry were all performed as described by Duncan et al., 2012.

RNA-seq: To compare the transcriptomes of metastatic BM1-VC and non-metastatic BM1-RKIP tumors, 1×10$^6$ cells were injected orthotopically. Tumors were harvested when they reached approximately 200 mm$^3$ size (about 3-weeks post inoculation), and then flash-frozen in liquid nitrogen. Tumor samples were pulverized immediately, and lysed in TRI Reagent® (Zymo Research, Cat. No. R2050-1-200). RNA was extracted using the Direct-zol™ RNA MiniPrep Kit (Zymo Research, Cat. No. R2052) following the manufacturer's instructions under RNAse-free conditions. In order to prevent contamination of the RNA samples by genomic DNA, the samples were treated with DNAse-I (Zymo Research, Cat. No. E1011-A) for 15 minutes at ambient temperature on the RNA extraction column. Total RNA was eluted in RNAse/DNAse-free water (Zymo Research, Cat. No. W1001-30) and submitted to the University of Chicago Genomics Facility for further analysis.

RNA quality assessment, library preparation, and sequencing of the tumor RNA samples were all performed by the Genomics Facility staff following the facility's standardized protocols. Quality of the samples were assessed using a Bioanalyzer, and the samples were determined to be of high quality with an average RNA integrity number (RIN) of 8.6. For the RNA-seq analysis there were 7 control tumors and 5 RKIP-overexpressing tumors, so an individual oligo dT selected was generated, mRNA directional library for each tumor sample without any pooling scheme. All 12 samples were run on the same lane in HiSEQ4000 to generate 50 base-pair long single-end reads.

Bioinformatic analysis of the RNA-seq results were all carried out using the web-based bioinformatics platform Galaxy (usegalaxy.org). Raw "*.fastq" files were uploaded to the Galaxy servers via a file transfer protocol (FTP) software. The reads were analyzed for GC content using "FastQC" and trimmed to remove adaptor sequences using "Trim Galore!". The reads were mapped to the human genome (hg19) using RNA STAR. In all samples, 70-75% of the reads were uniquely mapped. The resulting "*.bam" files were used to count reads per gene with "featureCounts". Finally, read counts were normalized and analyzed for differential expression between Control and RKIP-overexpressing samples using "DESeq2". Principle component analysis on the normalized read counts demonstrated two distinct clusters of samples, separated by the RKIP status.

The Cancer Genome Atlas Program (TCGA) data analysis: For the analysis of patient data, normalized RNA-seq results were accessed through the cBioportal database (Gao et al., 2013). For every TCGA cancer type, the provisional data sets were used for analysis (tagged "TCGA, Provisional" on cBioportal). Lists of genes that correlate with RKIP and BACH1 were also downloaded directly from cBioportal, as the data base already has these correlation matrices generated for each TCGA cancer type. Oncotype and expression heatmap plots were directly generated by cBioportal. Prior to generation of these plots, z-score threshold of 0.5 was arbitrarily chosen to classify patients into high versus low expressors for a particular gene of interest. For example, if a patient's tumor sample has an RKIP expression level that has a z-score higher than 0.5, then the sample was deemed "RKIP-high", and if the z-score was below –0.5, the sample was deemed "RKIP-low". If the z-score falls within –0.5 and 0.5, then the sample was considered as "Intermediate", or "Other". Both Pearson and Spearman correlations were used in determining gene-gene correlations and a coefficient cut-off of 0.3 was chosen arbitrarily for both correlation metrics.

The clinical metadata regarding the TCGA breast cancer data set was downloaded from cBioportal. The clinical information on breast cancer patients does not contain TNBC status information. TNBC vs. Non-TNBC status was assigned to breast cancer samples by considering immunohistochemistry-based assessment of ER, PR, and HER-2 expression. If the sample was negative for all three of these parameters by IHC, the sample was deemed "TNBC" (n=115). Otherwise, the sample was considered as "Non-TNBC". For the survival analysis, "survival" and "survminer" R packages were used. TCGA breast cancer patients were separated into two groups: target-gene high expressors (TG-high) and target-gene low expressors (TG-low) based on the expression of 5 motility and adhesion genes (ROCK2, DOCK4, ITGA1, APC, and RAPGEF6). If a patient sample falls above the median for all 5 genes, that patient was deemed TG-high. If a patient sample falls below the median for all 5 genes, that patient was deemed TG-low. Survival probability with respect to time (in months) was plotted in a Kaplan-Meier curve and statistical significance was determined using a logrank test.

GSEA and METASCAPE: Functional gene set enrichment analysis of the differentially expressed genes in the RNA-seq data as well as the genes that correlate with RKIP and BACH1 was performed using the web-based interface of the Metascape software (Tripathi et al., 2015). For the identification of pathways and processes enriched in the input gene lists, both "Gene Ontology" (GO) and "Kyoto Encyclopedia of Genes and Genomes" (KEGG) categories were considered. A minimum overlap of 5 genes and an enrichment score of 1.5 were chosen as the enrichment parameters. An adjusted p-value cut-off of 0.05 was chosen as the significance threshold.

Tissue fixation and Immunohistochemistry: Tumor tissues were fixed in 10% formalin upon dissection for 72 hours and then transferred into 70% Ethanol for long-term storage. Fixed tissues were embedded in paraffin and sliced into 5-micron sections prior to immunohistochemical analysis. All immunohistochemistry for this body of work was performed by the University of Chicago Human Tissue Resource Center staff. Briefly, tissue sections were stripped of the paraffin through xylene treatment and rehydrated with an ethanol-to-water gradient washes. Then the sections were incubated in antigen retrieval buffer at 97° C. for 20 minutes Immunohistochemical analysis of macrophage infiltration within the primary tumor tissues was performed by using primary antibodies against mouse macrophage marker F4/80. Both primary and secondary antibody treatments were carried out at room temperature in a humidity chamber. After secondary antibody incubation, the slides were developed using Elite Kit (Vector Laboratories, Cat. No. PK-6100). Finally slides were counterstained with hematoxylin and bluing reagent and mounted with a cover glass. Stained slides were scanned at 10× on Nikon Eclipse Ti2 Inverted Microscope System. Macrophage infiltration of the tumors was quantified on FIJI (ImageJ) software using the IHC Image Analysis Toolbox plugin. For each tissue, five randomly-selected fields were exposed to same quantication parameters and the average signal from all five fields was used to compare macrophage infiltration between different tumor tissues.

Example 1: RKIP Partially Inhibits Multiple Kinases Within the Extended MAPK Network MIB-MS analysis using beads bound to kinase inhibitors (MIBs) followed by mass spectrometry to isolate and quantify active kinases (Duncan et al., 2012) was used to discover kinase networks targeted by RKIP in TNBC tumors. Of the 250 active kinases that were present in both control tumors and RKIP-expressing BM1 tumors from mouse xenografts, RKIP significantly altered the activity of 30 (FIG. 1A). Consistent with its role as a kinase suppressor, RKIP inhibited most of these kinases (23) including the previously identified RKIP target ERK2 (Yeung et al., 1999); the remaining 7 kinases were upregulated.

Figure 1B:
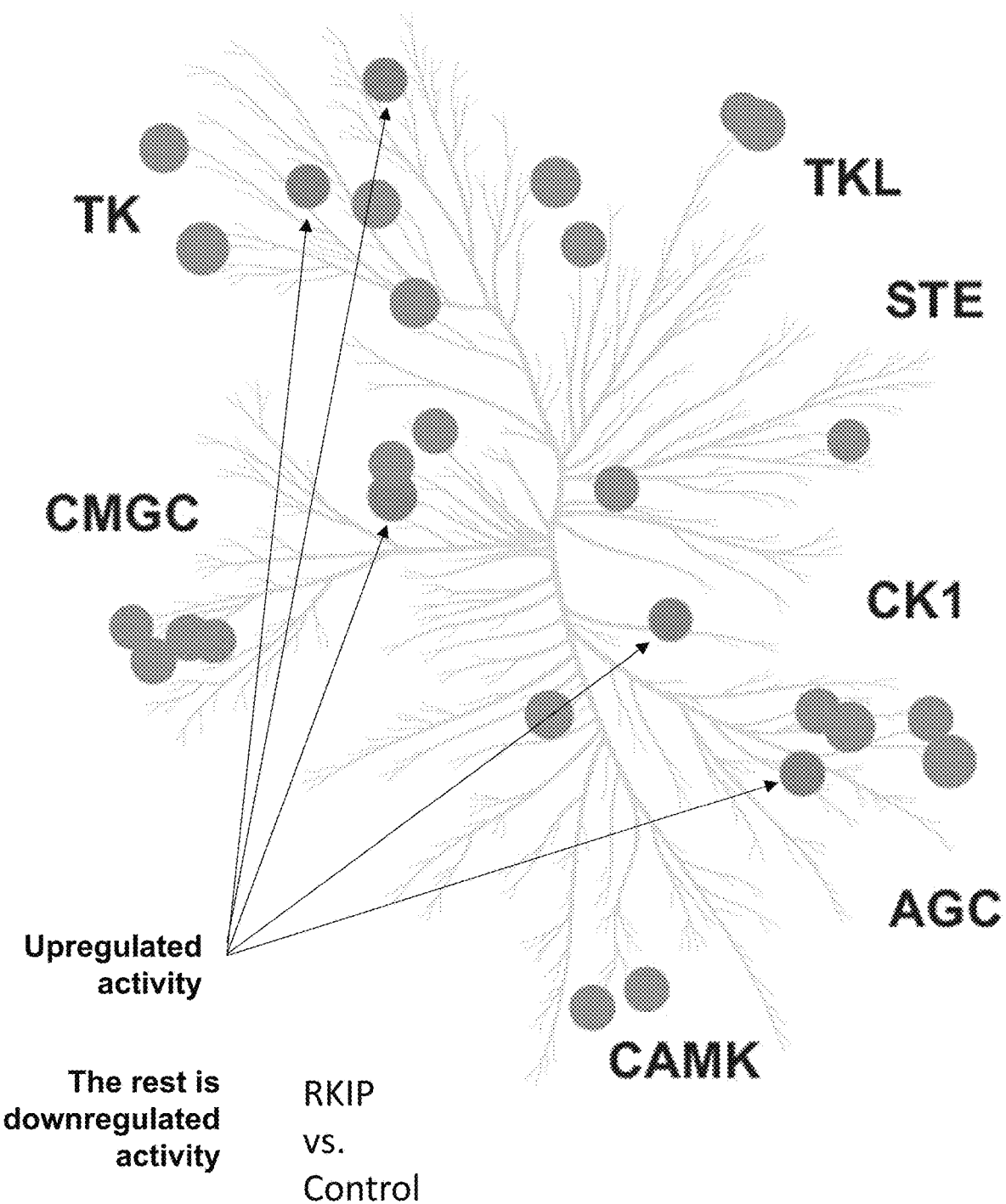
Figure 1C:
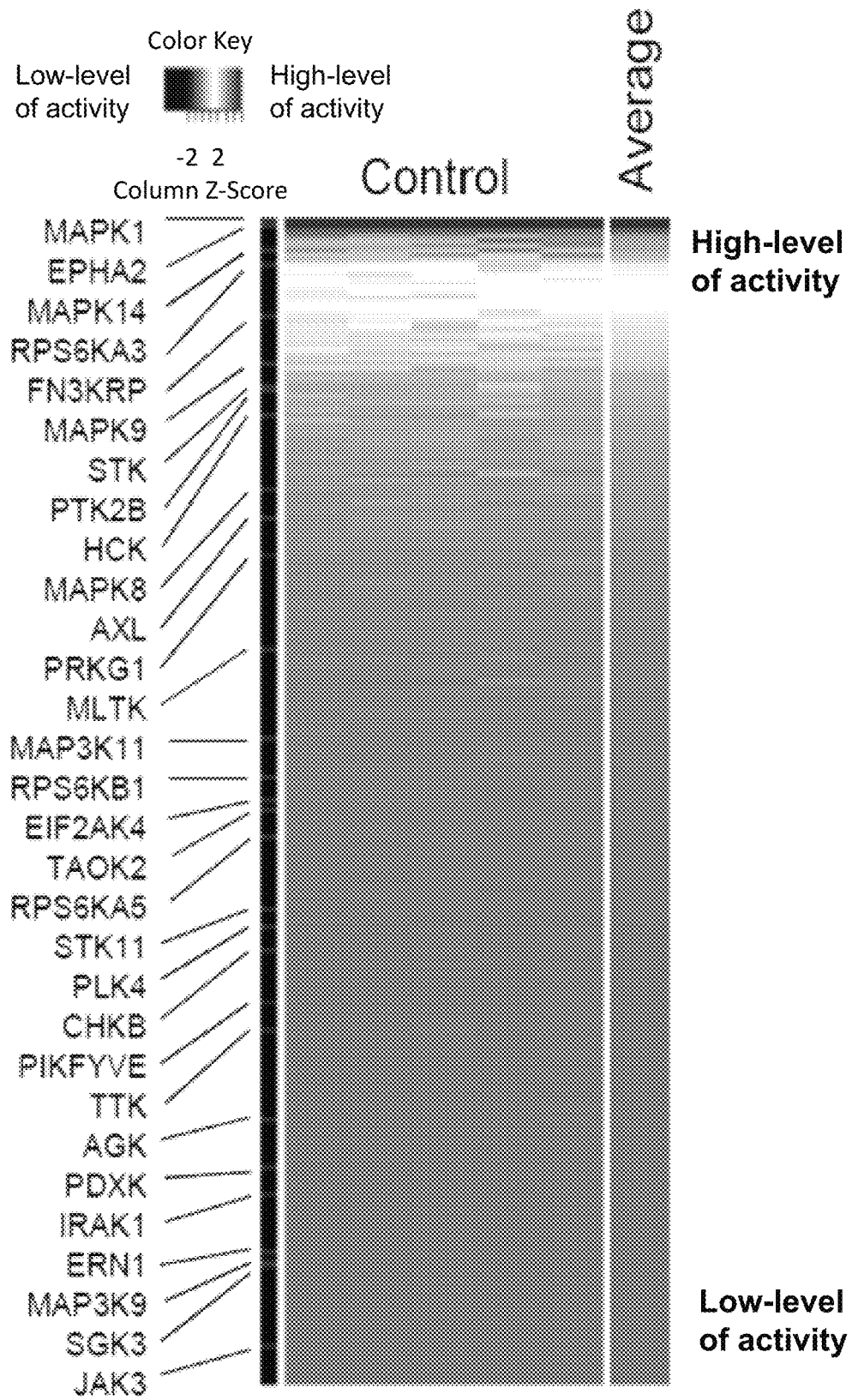
Figure 1D:
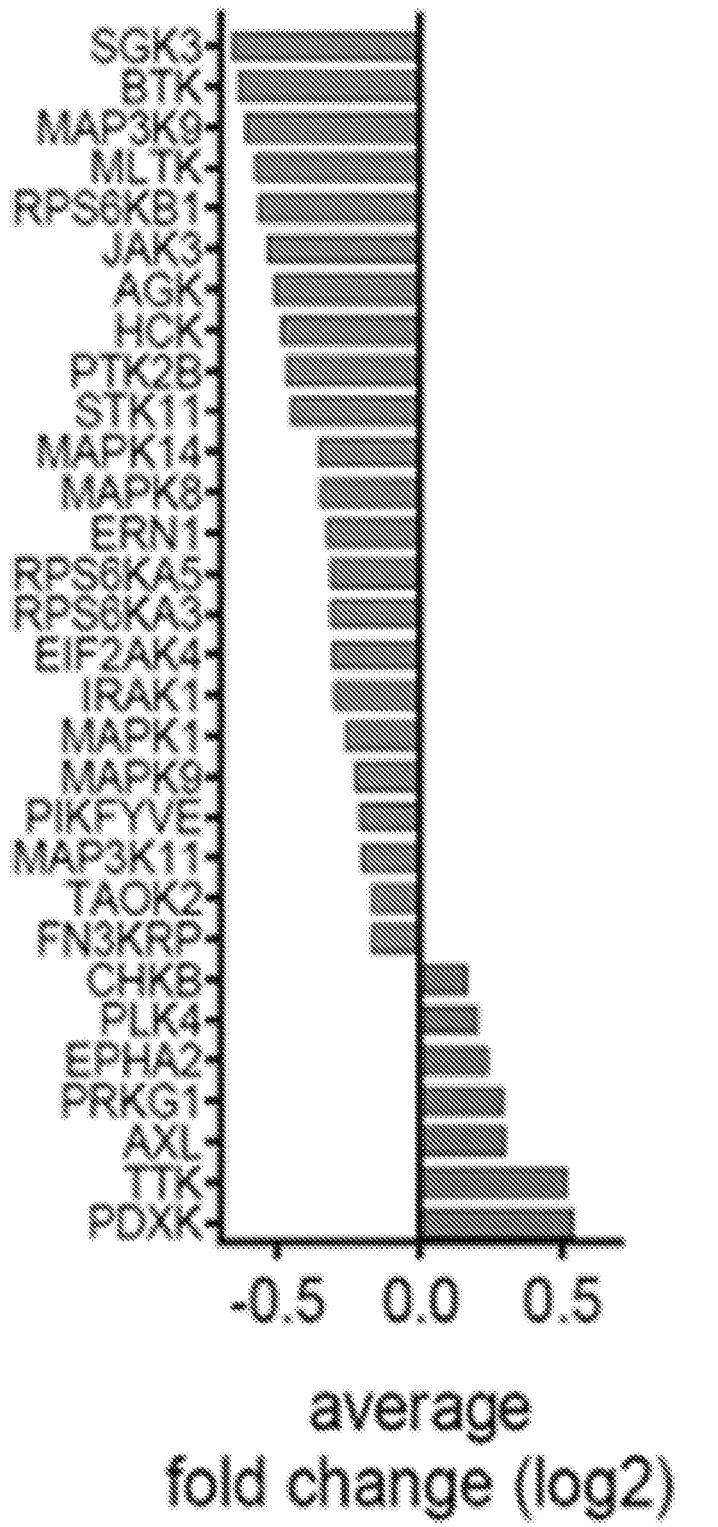

Three aspects of RKIP regulation stand out. First, the kinases targeted by RKIP were distributed across multiple branches of the kinome tree (FIG. 1B). Second, these kinases ranged from high activity to low activity kinases, indicating that the degree of kinase activation does not correlate with metastatic potential (FIG. 1C). Third, the effect size of inhibition or activation of RKIP targets in RKIP-overexpressing tumors was roughly 30% (FIG. 1D). Thus, in contrast to common cancer therapeutic practice, RKIP partially inhibited multiple kinases rather than fully inhibiting one or two kinases. These findings suggest that partially inhibiting a broad range of nodes within a kinase network, including low-abundance/low-activity kinases, might be an effective way of altering a tumor's metastatic state.

Figure 1E:
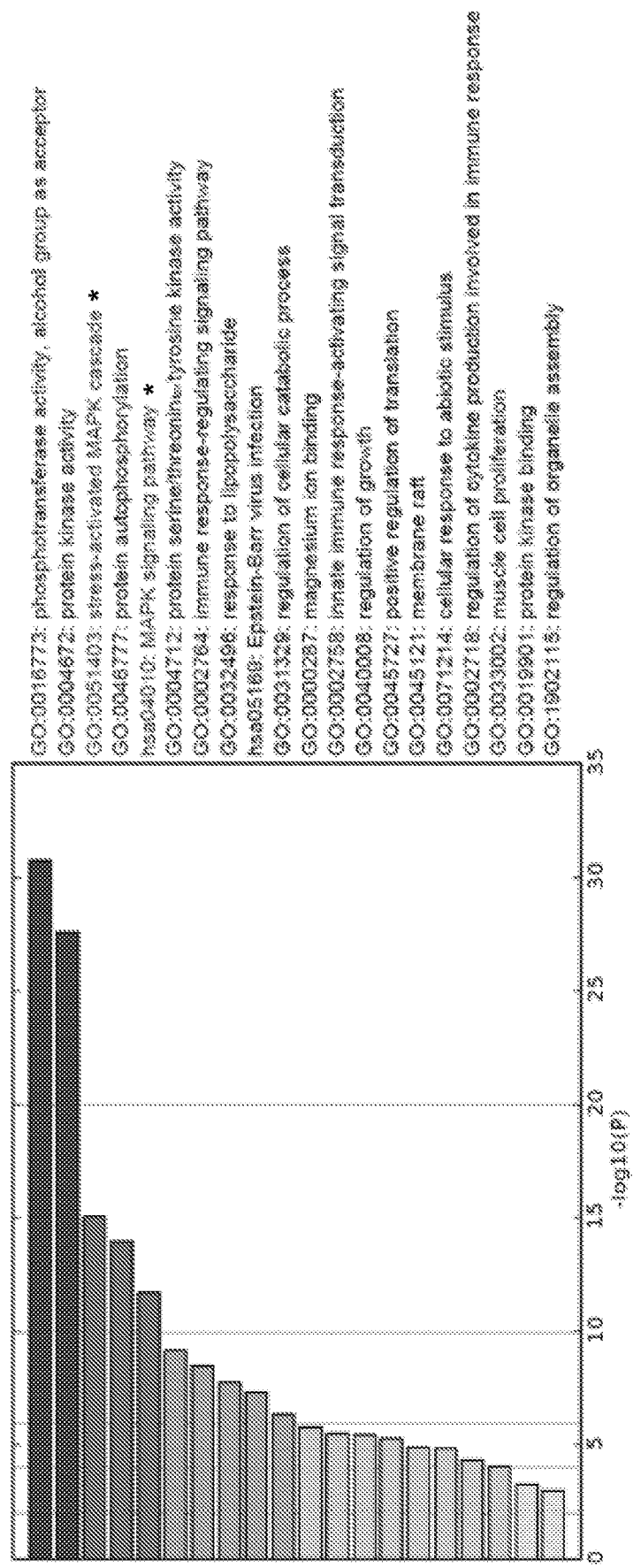

Functional analysis of the 23 downregulated kinases using Metascape (Tripathi et al., 2015) showed enrichment for stress kinase signaling (FIG. 1E). Ingenuity® pathway analysis indicated that the majority of these kinases are functionally related, and the stress MAP kinases (JNK, p38) as well as ERK are at the core of the network (FIG. 1F).

Figure 1G:
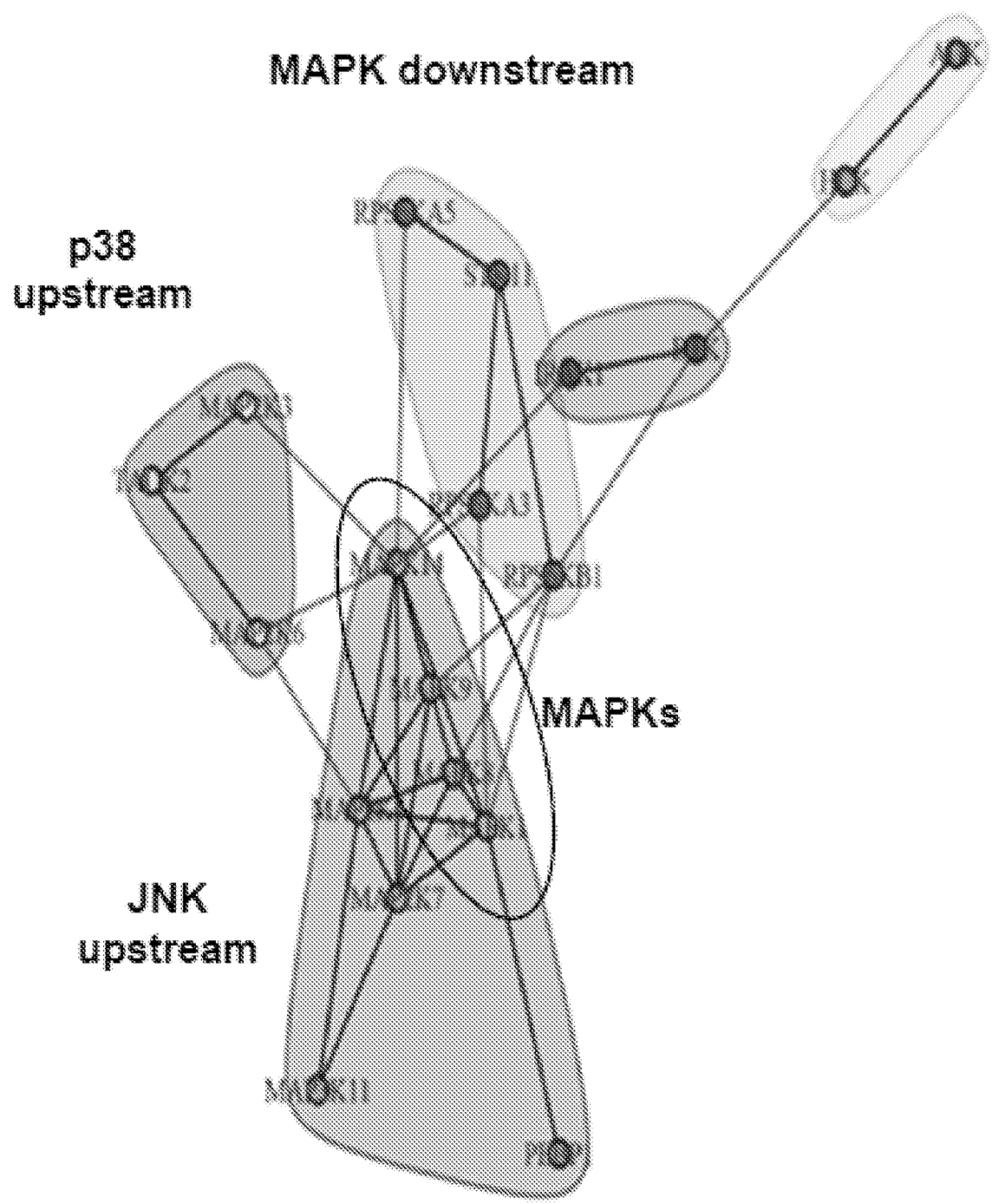

Community analysis identified three main protein-protein interaction subnetworks comprised of the extended MAPK family including kinases upstream of p38 (TAOK2, MKK3, MKK6), upstream of JNK (MLK1, MLK3, MKK4); and the p70/p90 kinases downstream of the MAPKs (MSK1, RSK2, and p70/85 S6K1) (FIG. 1G). These results indicate that the three MAPKs (JNK, p38 and ERK) as well as their upstream regulators and downstream effectors comprise the core RKIP-regulated network in TNBC cells.

Figure 1H:
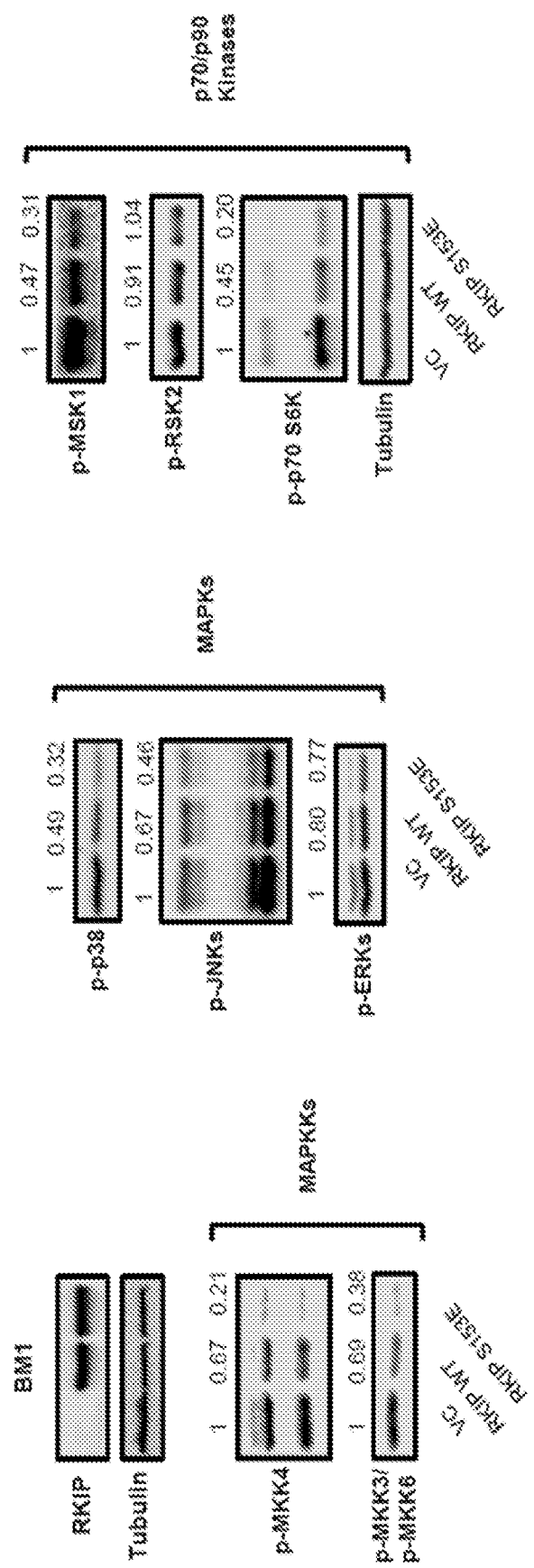

The inhibition was validated by exogenously expressed RKIP of stress-activated MAPKs in anisomycin-stimulated human (BM1, MDA-MB-436) or mouse (LMB, M6C) TNBC cell lines Similar results were obtained with S153E RKIP, a mutant that constitutively binds Raf1 (Dangi-Garimella et al., 2009; Skinner et al., 2017) (FIGS. 1H and 2A). The importance of stress MAPK signaling for migration and invasion was confirmed using small molecule inhibitors of p38 or JNK (FIG. 2B). Overall, these data show that RKIP reprograms TNBC cells from an invasive to non-invasive state by inhibiting the activity of the MAPK network and, in particular, the stress kinases.

Example 2: Inhibiting Stress MAPKs Mimics RKIP Function

Figure 3A:
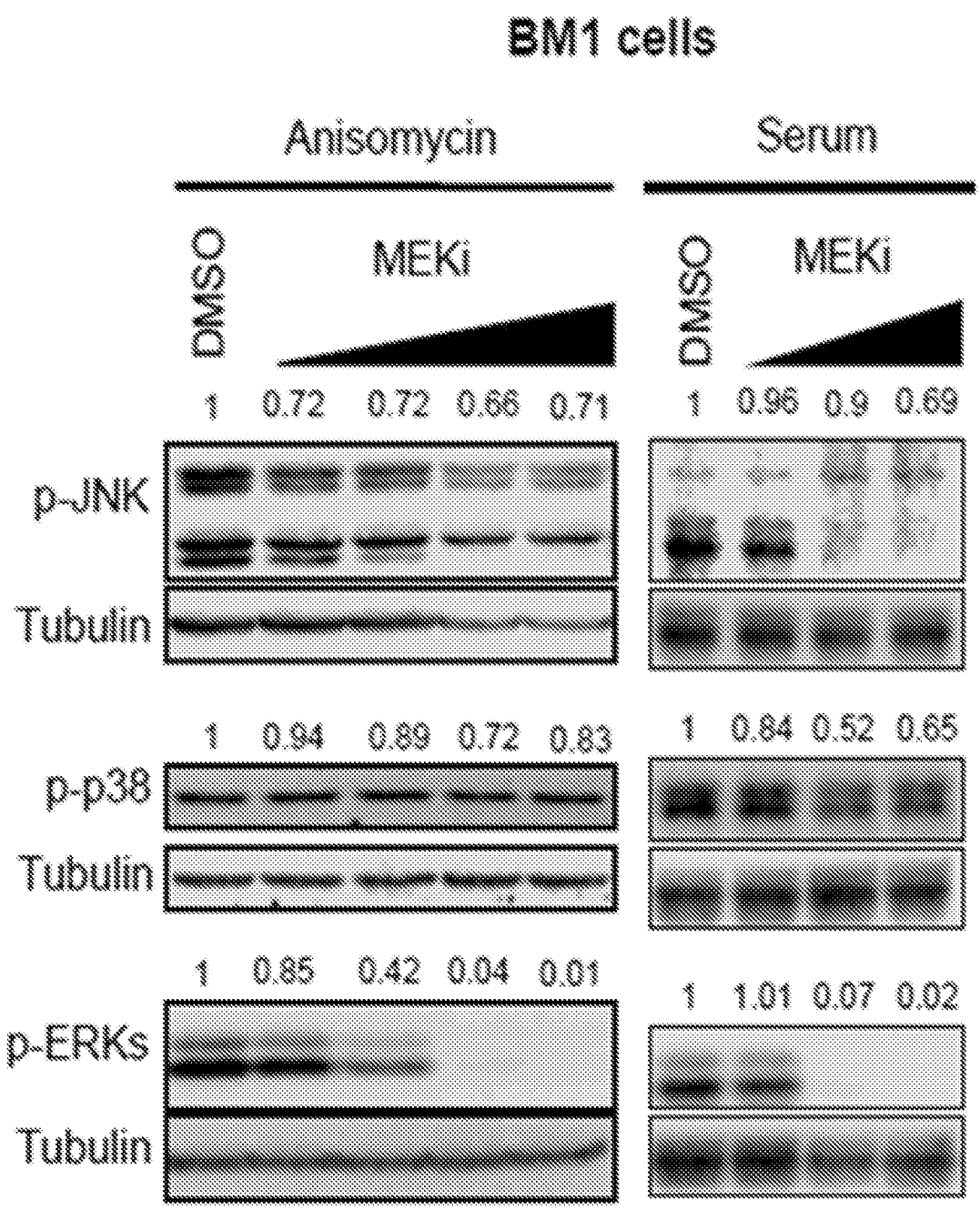
Figure 4A:
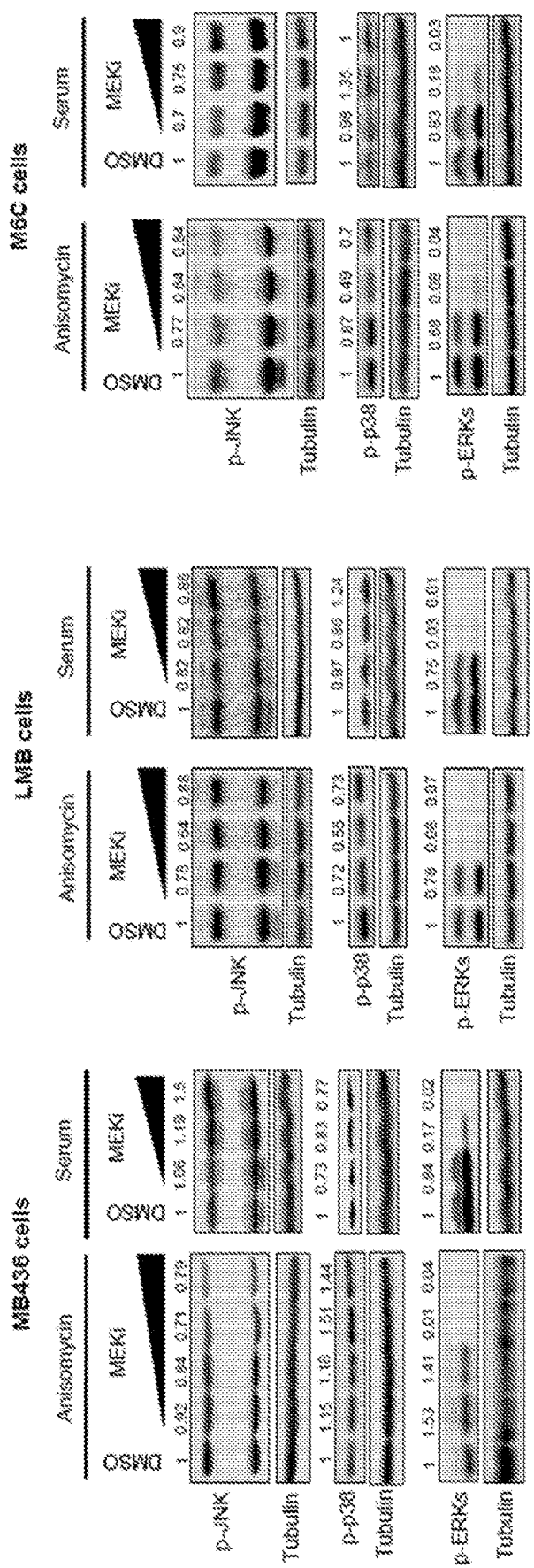
FIGS. 4A-4G: RKIP overcomes the context-dependent complexity of the extended MAPK network by targeting multiple nodes.

Targeting the Raf node in the MAPK network was investigated. In a screen across four human and mouse TNBC cell lines, MEK inhibition by Trametinib partially attenuated JNK phosphorylation under anisomycin induction, but p38 phosphorylation was not consistently inhibited (FIGS. 3A, 3B, and 4A) Similarly, in serum-induced cells, there was no significant change in p38 phosphorylation and even attenuation of JNK phosphorylation was variable (FIGS. 3A, 3B, and 4A). Given the variability in stress MAPK signaling dependent upon treatment and cell-type, these results indicate that MEK inhibition alone is not sufficient to mimic RKIP signaling.

Figure 4B:
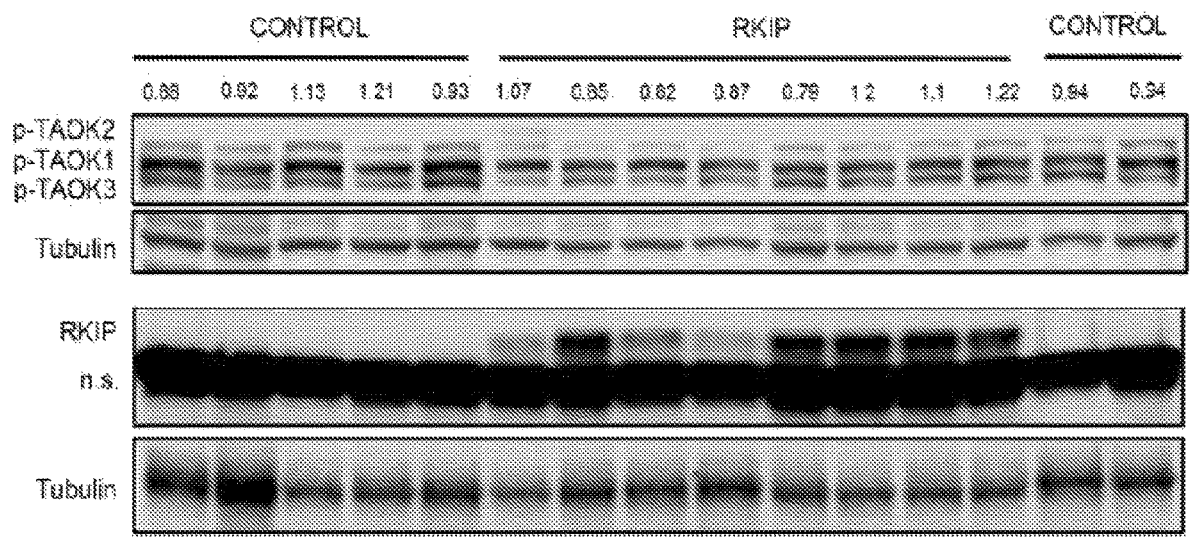
Figure 4B:
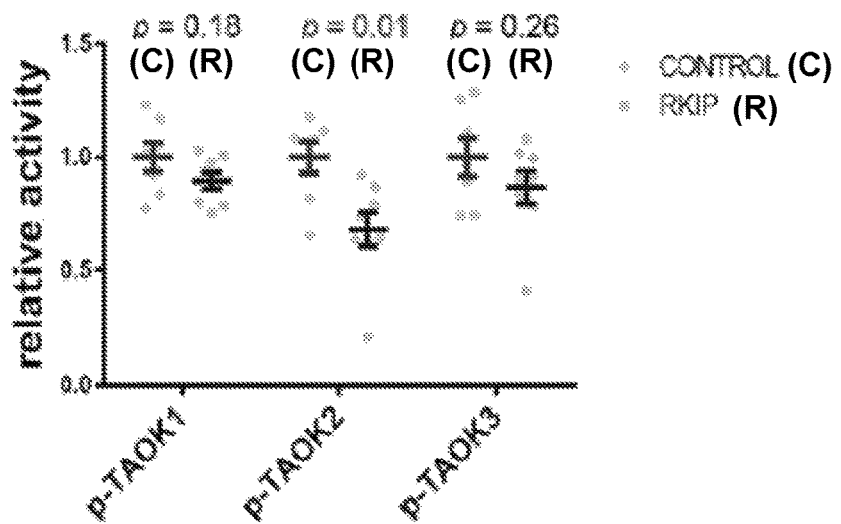
Figure 4C:
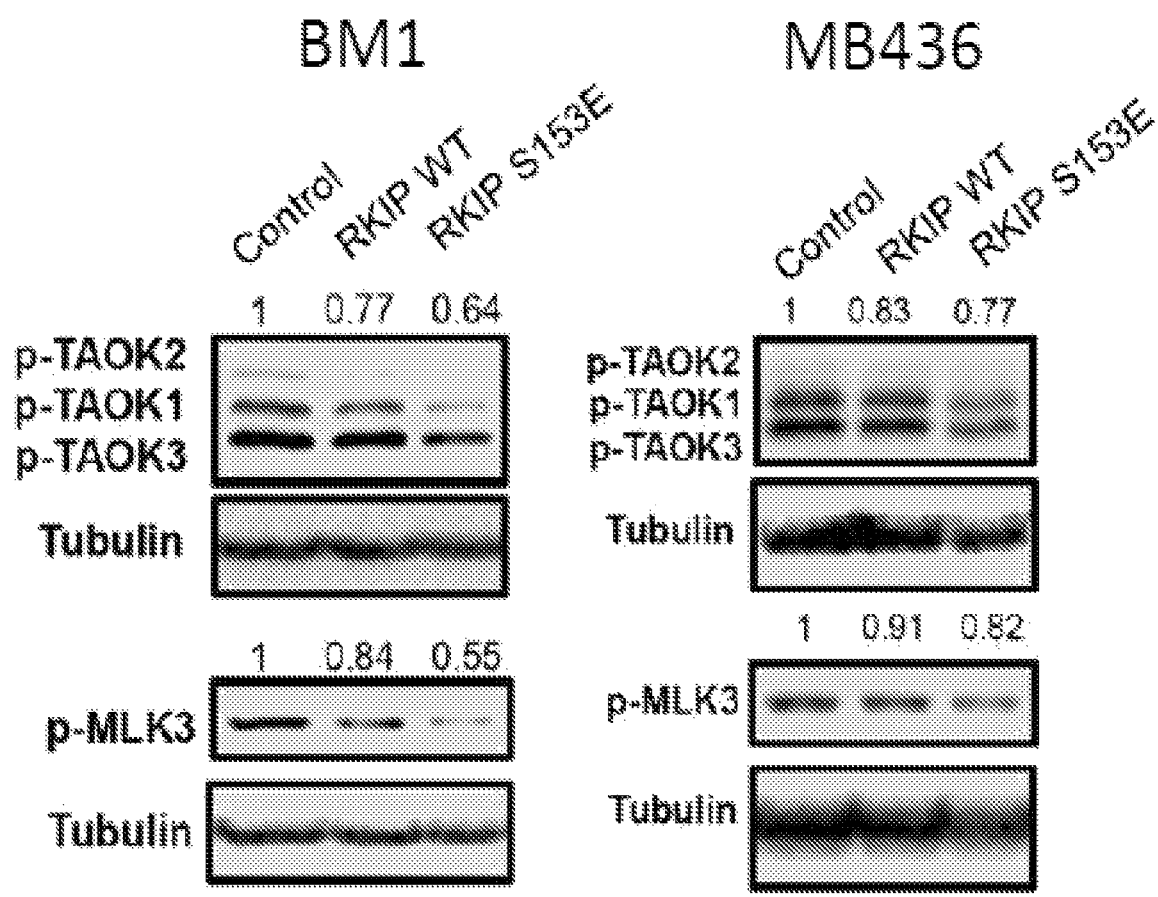
Figure 4D:
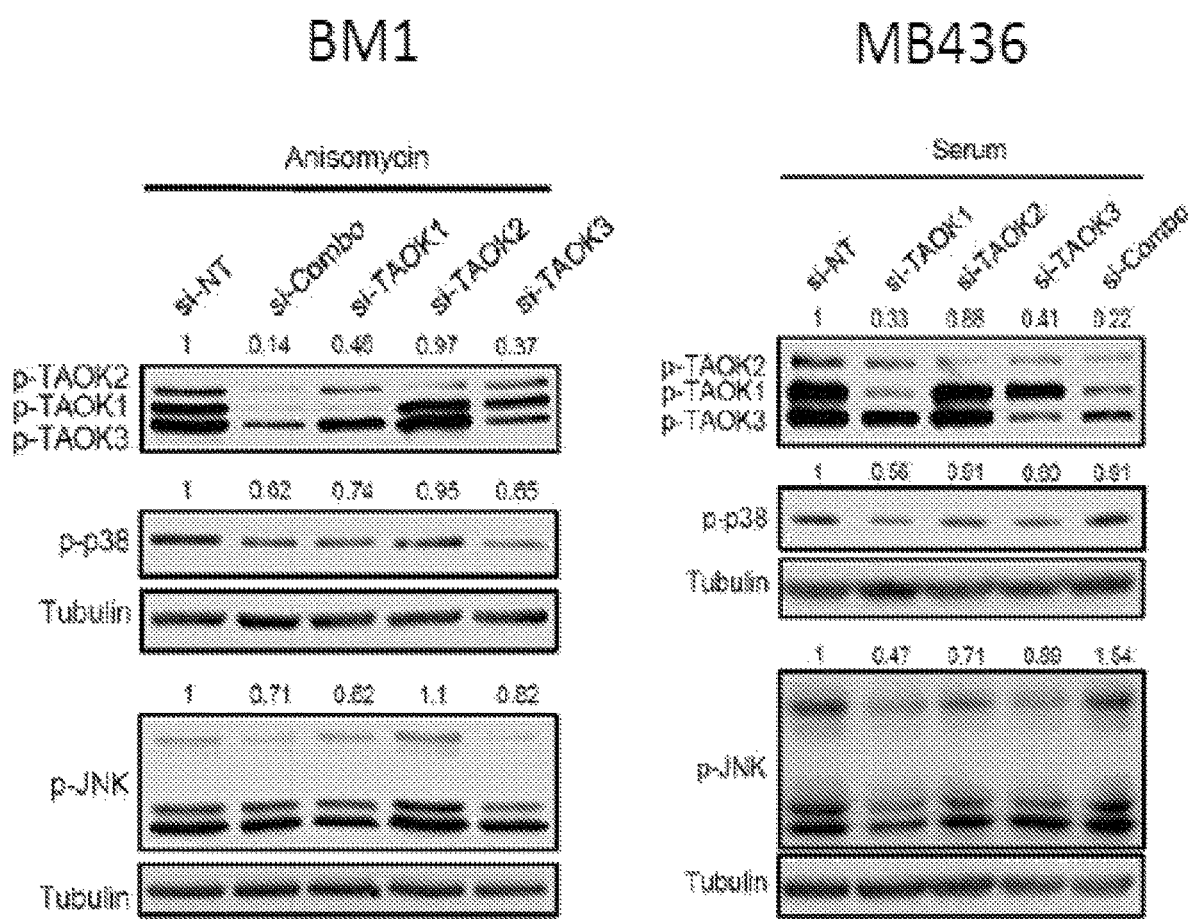
Figure 4E:
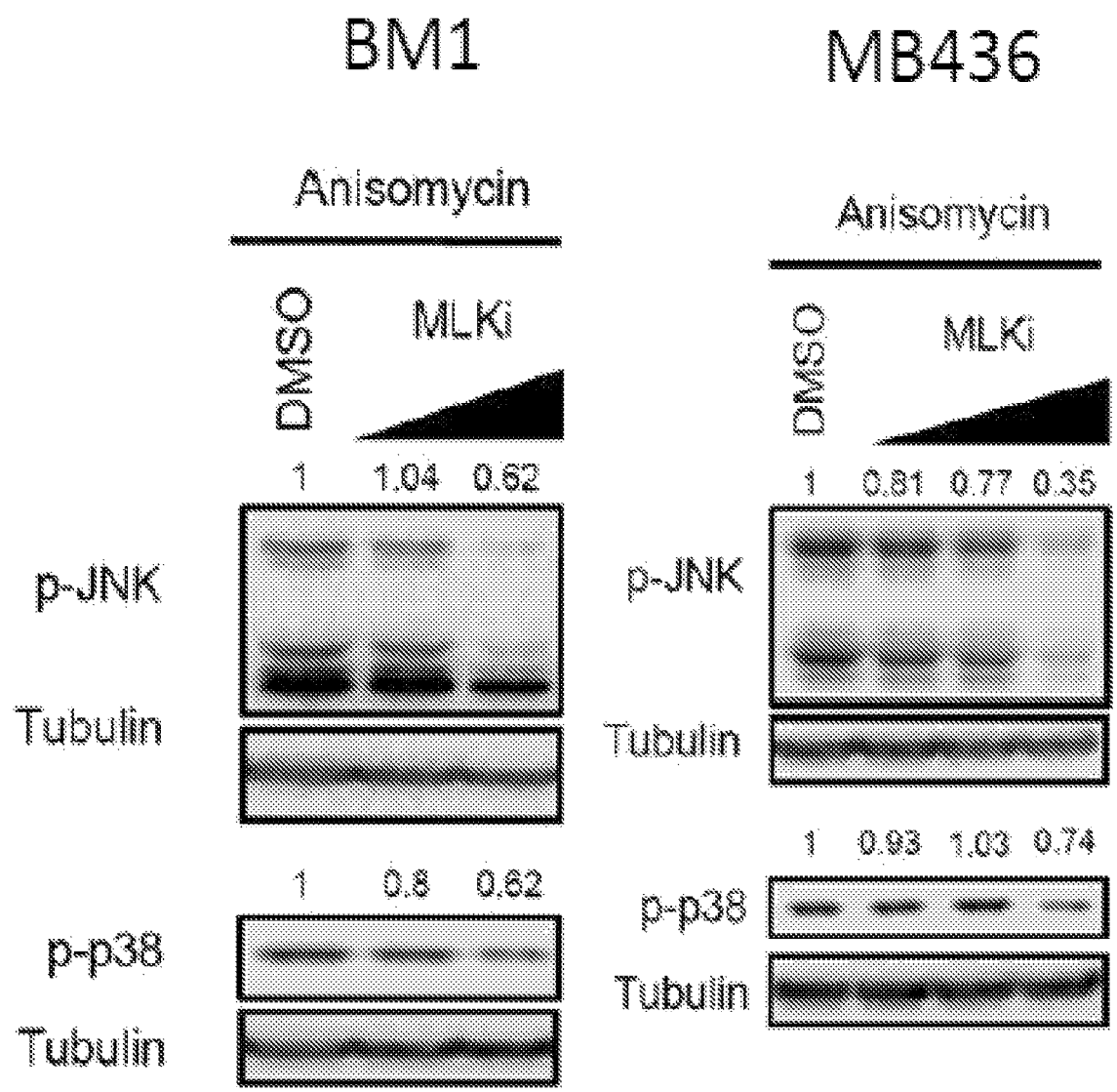

The MIB data from BM1 xenografts was re-analyzed in order to identify upstream regulators of the stress kinases targeted by RKIP in tumors (see FIG. 1A). Three members of the MAP3K family reported to activate both p38 and JNK signaling were discovered: TAOK2, MLK1 and MLK3. (Chen et al., 1999; Dhillon et al., 2007). RKIP-expressing tumors had lower TAOK2 autophosphorylation, an indicator of kinase activity (Zhou et al., 2004), in M6C syngeneic tumor model, mirroring the findings from the BM1 xenograft studies (FIG. 4B). In contrast to tumors, RKIP reduced the activity of all three TAO kinases (TAOK1, TAOK2, TAOK3) in anisomycin-induced human cell lines (FIG. 4C). In both tumors and cell lines, autophosphorylated TAOK1 and TAOK3 were more abundant than TAOK2, and caused more dramatic reduction in p38 levels than TAOK2, when silenced by siRNA in vitro. (FIGS. 4B and 4D). Interestingly, depletion of TAOKs also partially downregulated JNK activity (FIG. 4D), indicating that TAOKs primarily regulate p38 but may also activate JNK in TNBC cells.

Figure 4F:
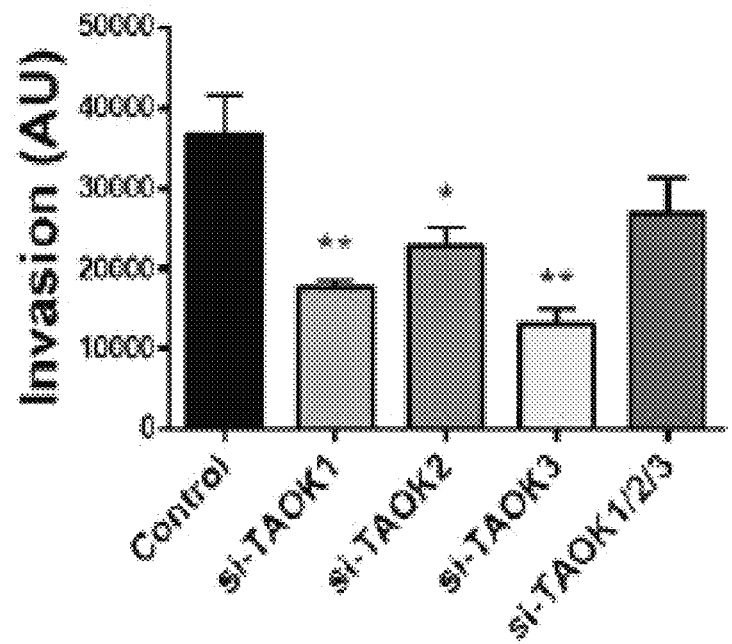

In contrast to TAO kinases, MLK kinases have been primarily characterized as MKK4 and JNK activators, but have also been reported to activate p38 signaling (Gallo and Johnson, 2002; Rattanasinchai and Gallo, 2016). Exogenous RKIP expression diminished MLK3 activation in anisomycin-induced human cell lines in vitro (FIG. 4C), consistent with the data from the BM1 xenograft tumors. In the same cell lines, a decrease in both JNK and p38 activation was observed when treated with URMC-099, an MLK3 inhibitor that also targets MLK1 (FIG. 4F). These results confirm that MLK1,3 primarily activate JNK in TNBC cells, but can also activate p38 dependent on the stimulus and cell type.

Figure 5A:
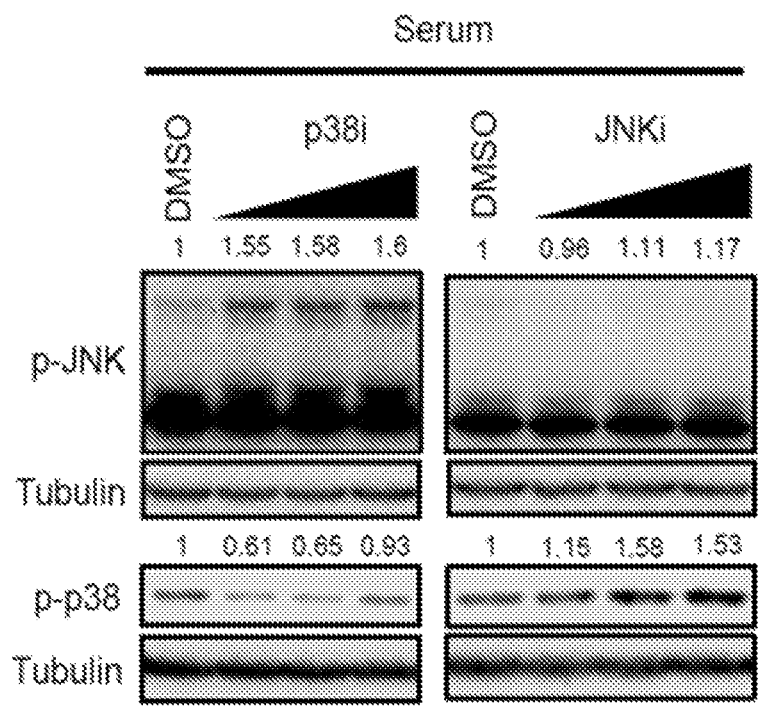
FIGS. 5A-5D: Negative crosstalk between p38 and JNK in TNBC cell lines is context-dependent. Related to FIGS. 3A-3E.
Figure 5B:
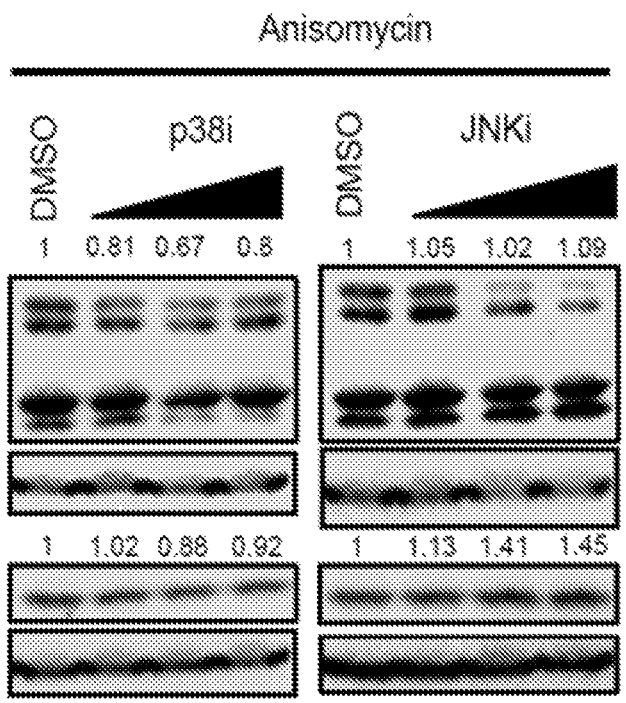
Figure 5C:
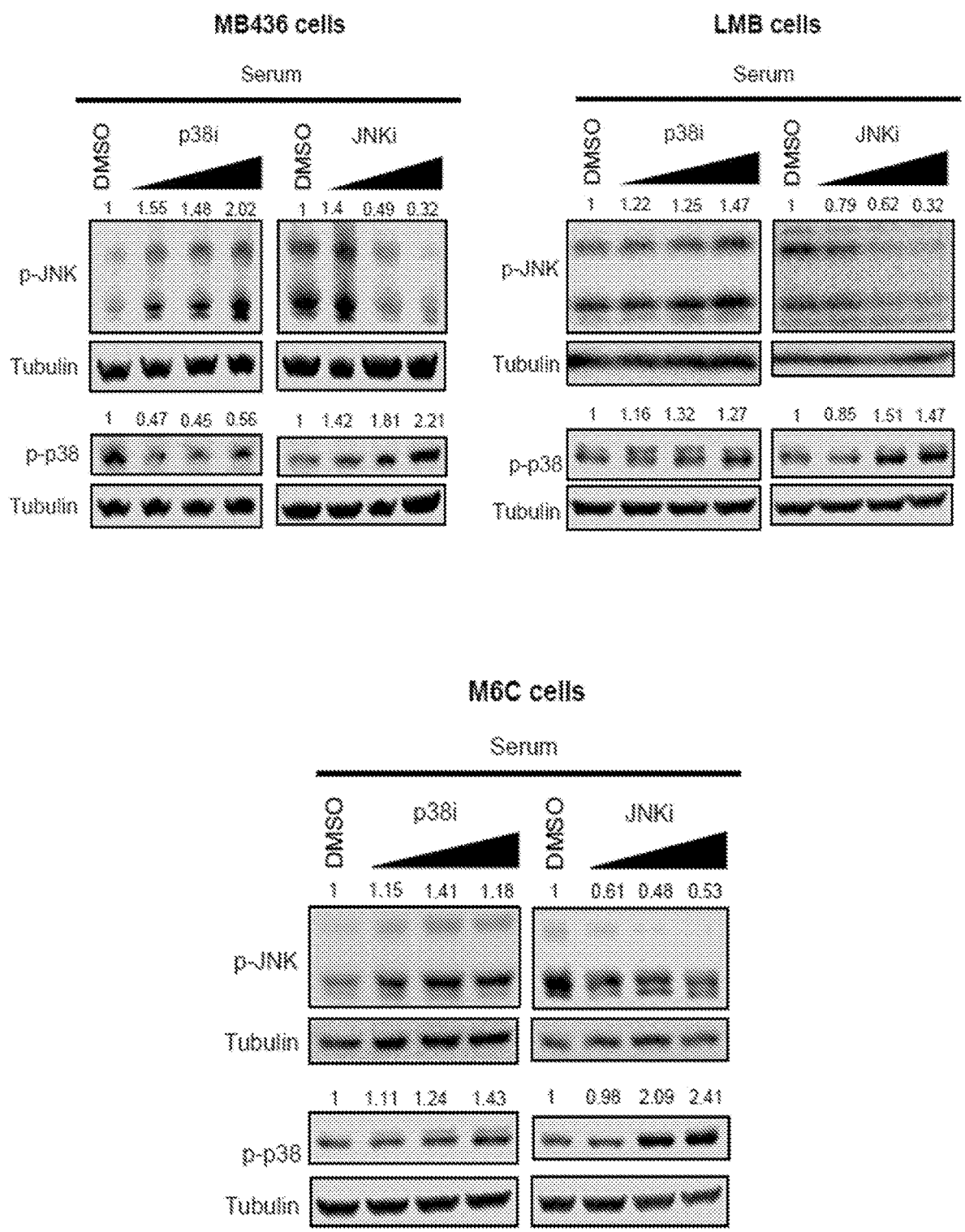
Figure 5D:
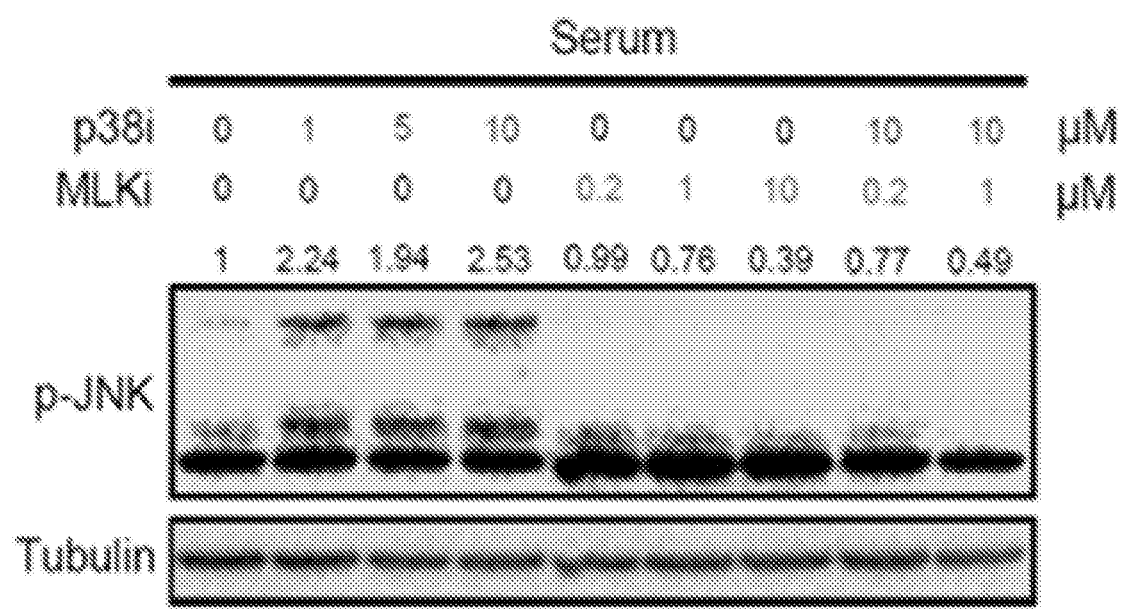
Figure 5D:
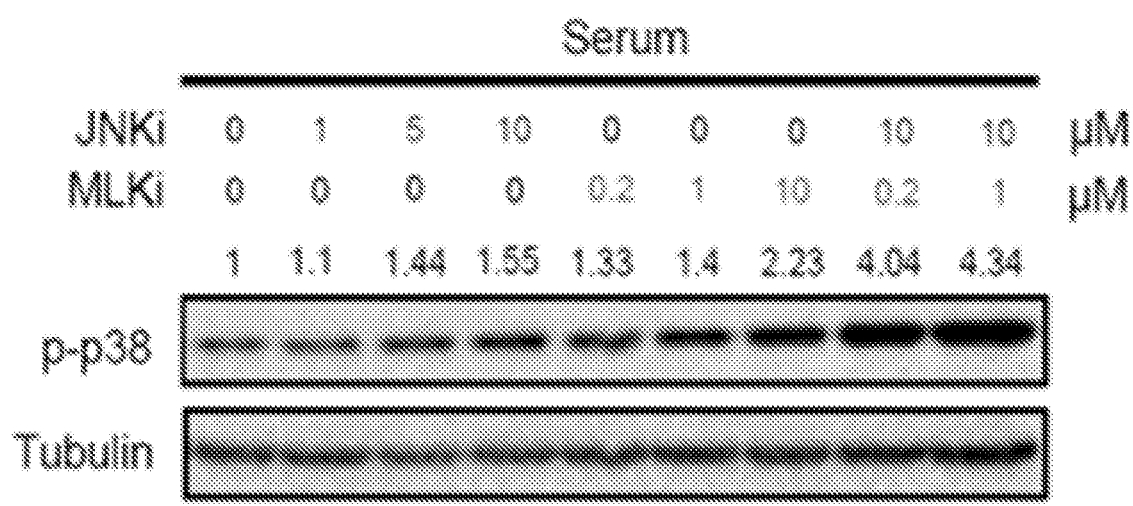

To investigate the crosstalk between p38 and JNK, small molecule inhibitors of p38 and JNK, SB203580 and SP600125, respectively, were used. A negative crosstalk between p38 and JNK was consistently observed in serum-induced human and mouse TNBC cell lines. In all four cell lines, inhibition of JNK by SP600125 induced p38 activation, while p38 inhibition by SB302580 resulted in JNK activation (FIGS. 5A and 5C). Under anisomycin-induced BM1 cells, however, p38 inhibition did not result in activated JNK signaling (FIG. 5B), highlighting the stimulus-dependent nature of the MAPK crosstalk. In the case of serum-induced BM1 cells, JNK activation via p38 inhibitor was mediated through MLK, whereas JNK inhibition of p38 was MLK-independent (FIG. 5D). Taken together, this analysis suggests that the crosstalk between MAPKs is cell- and stimulus-dependent, and that RKIP inhibits a combination of upstream and downstream kinases in the network to most effectively and consistently downregulate signaling by the stress MAPKs.

Figure 3C:
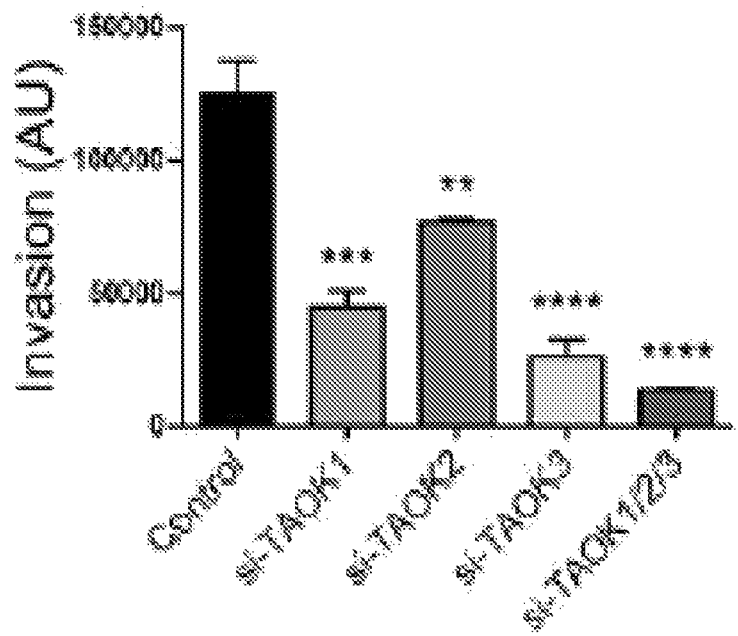
Figure 3D:
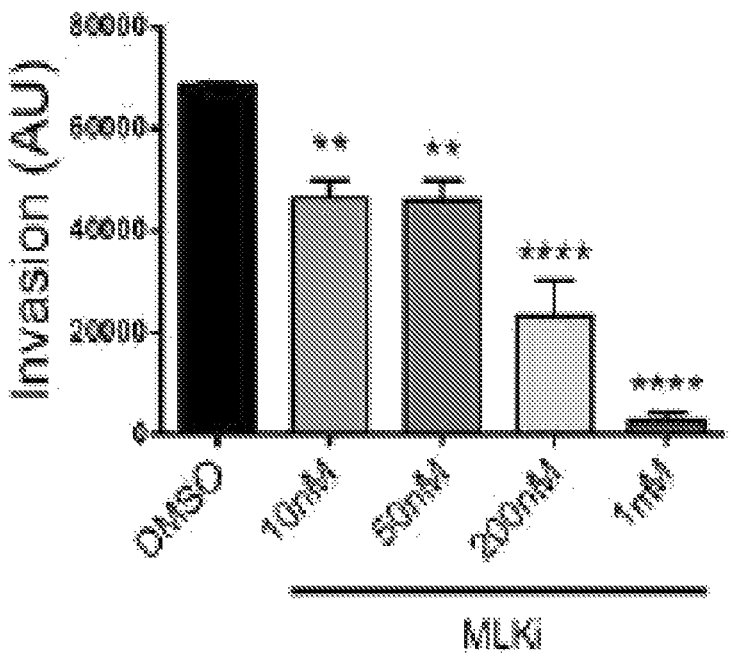
Figure 3E:
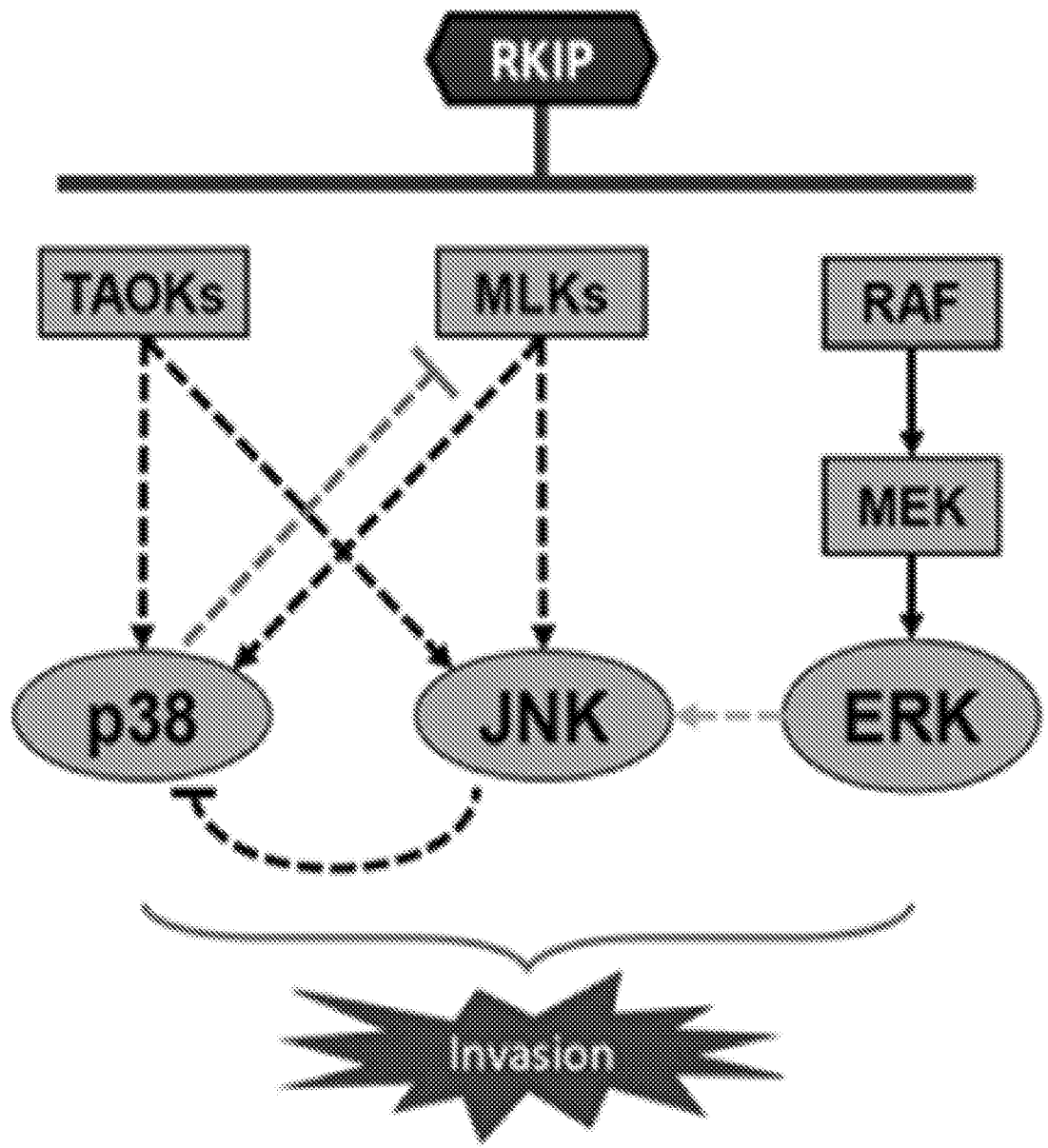
Figure 4G:
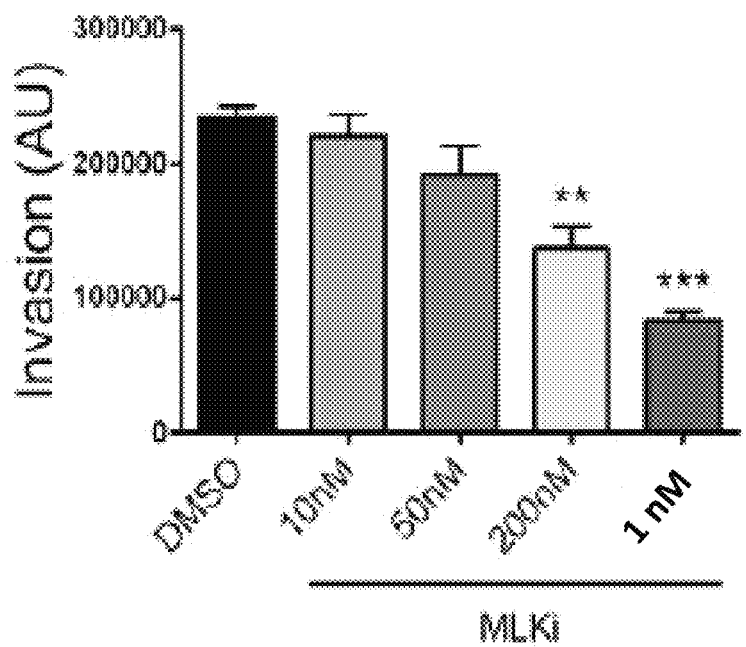

Like the stress MAPKs, both TAOs and MLKs regulate invasion of TNBC cells. siRNAs for TAOs 1-3 impaired the invasive capability of human BM1 and MB436 cells (FIGS. 3C and 4G). Similarly, MLK inhibition by URMC-099 decreased invasion by these two cell lines. (FIGS. 3D and 4H). Together, these data suggest that RKIP targets the upstream TAOKs and MLKs, thereby inhibiting invasion by preventing activation of the stress MAPKs p38 and JNK in TNBC cells (see summary scheme in FIG. 3E).

Figure 6A:
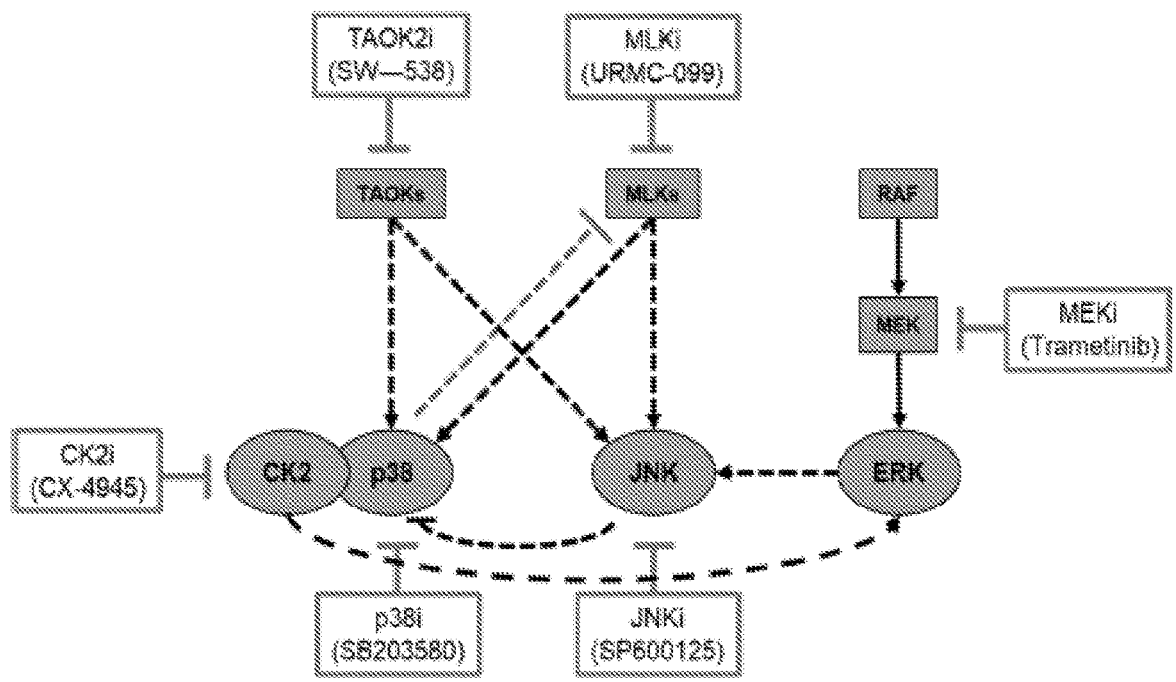
FIGS. 6A-6E: A four-drug combination targeting the MAPK network mimics RKIP's anti-invasive function in vitro.

Example 3: A Four-Drug Combination Targeting the MAPK Network Mimics RKIP's Anti-Invasive Function in Vitro In order to mimic the therapeutic action of RKIP, combinations of 6 kinase inhibitors that target different nodes in the MAPK signaling network were tested using both growth and invasion assays. The goal was to mimic RKIP action by finding a sub-therapeutic dose that suppressed invasion, but not cell growth. In addition to the MEK, JNK, p38 and MLK inhibitors used above (FIG. 3), CX-4945 (Silmitasertib) was also tested. Silmitasertib is an inhibitor of Casein Kinase 2 (CK2) which is involved in p38 and ERK signaling (Isaeva and Mitev, 2011; Sayed et al., 2000; Zhou et al., 2016), as well as SW-538, a more broad-based inhibitor that blocks some kinases that act on the MAPK network such as TAOK2, Raf1, JNK1, HGK, and GSK3b (Piala et al., 2016) (FIG. 6A).

Figure 7A:
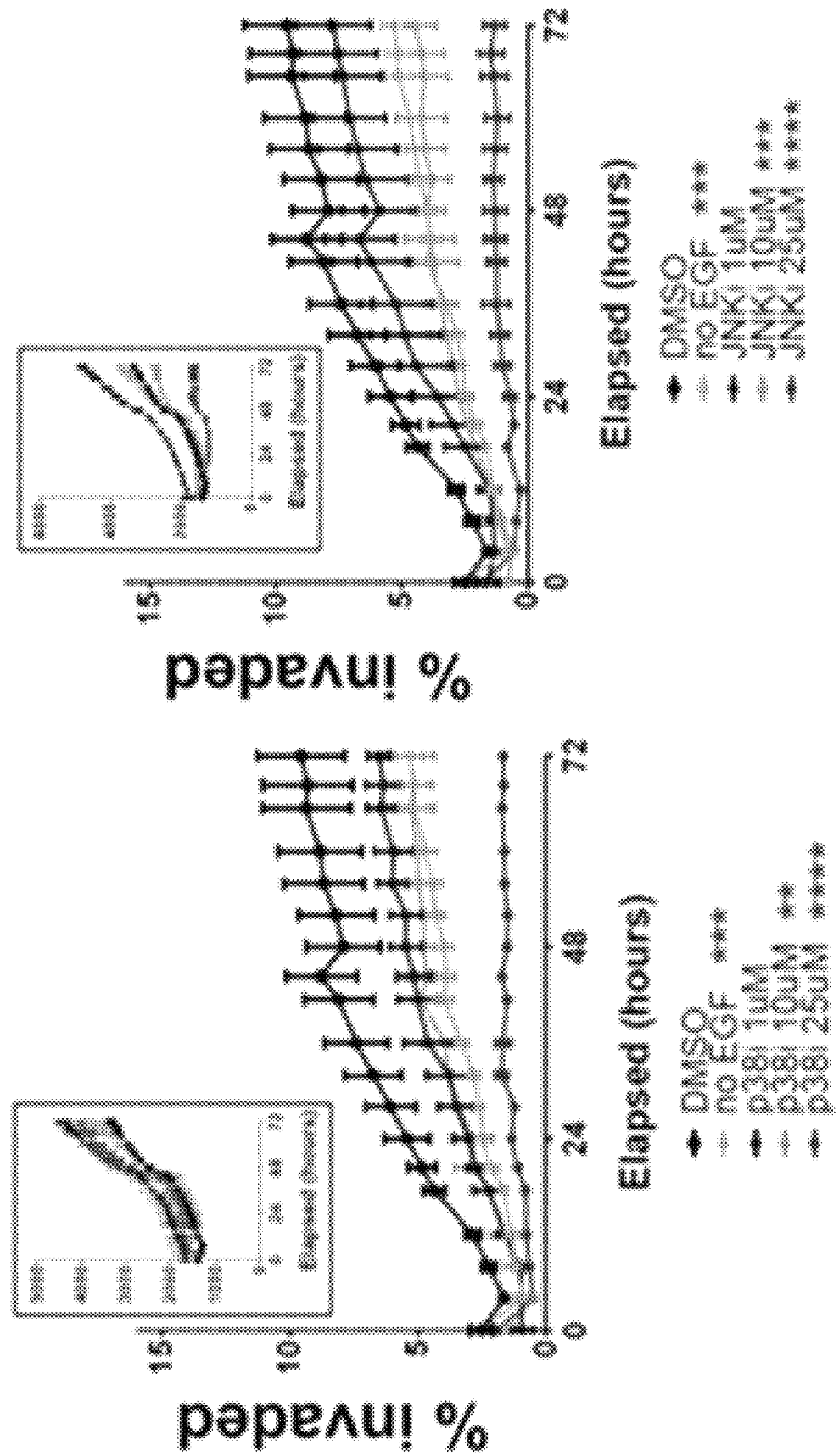
FIGS. 7A-7E: High-throughput invasion assays reveal a four-drug MAPK inhibitor combination that phenocopy RKIP in vitro. Related to FIGS. 6A-6E.
Figure 7A:
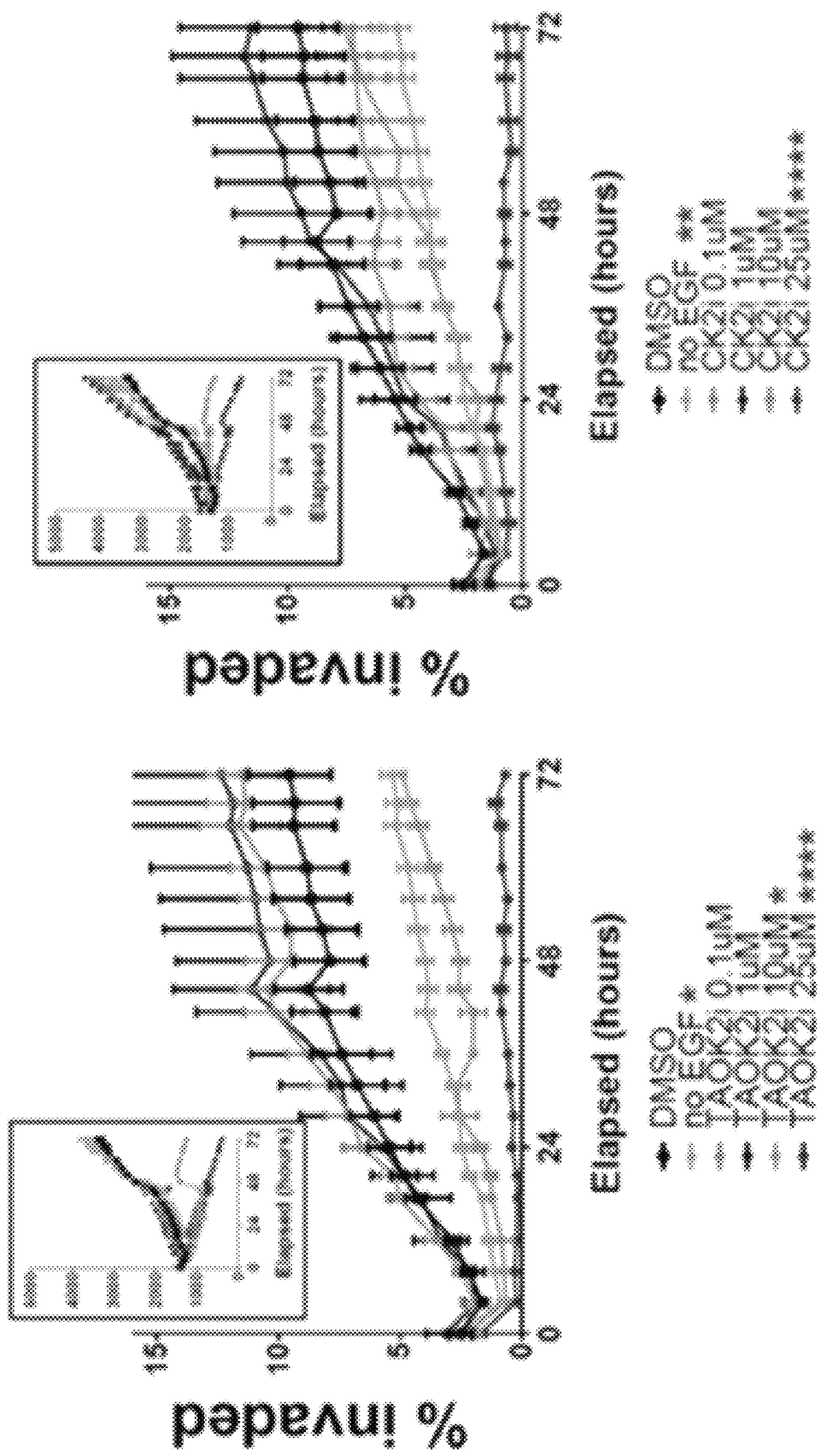
Figure 7A:
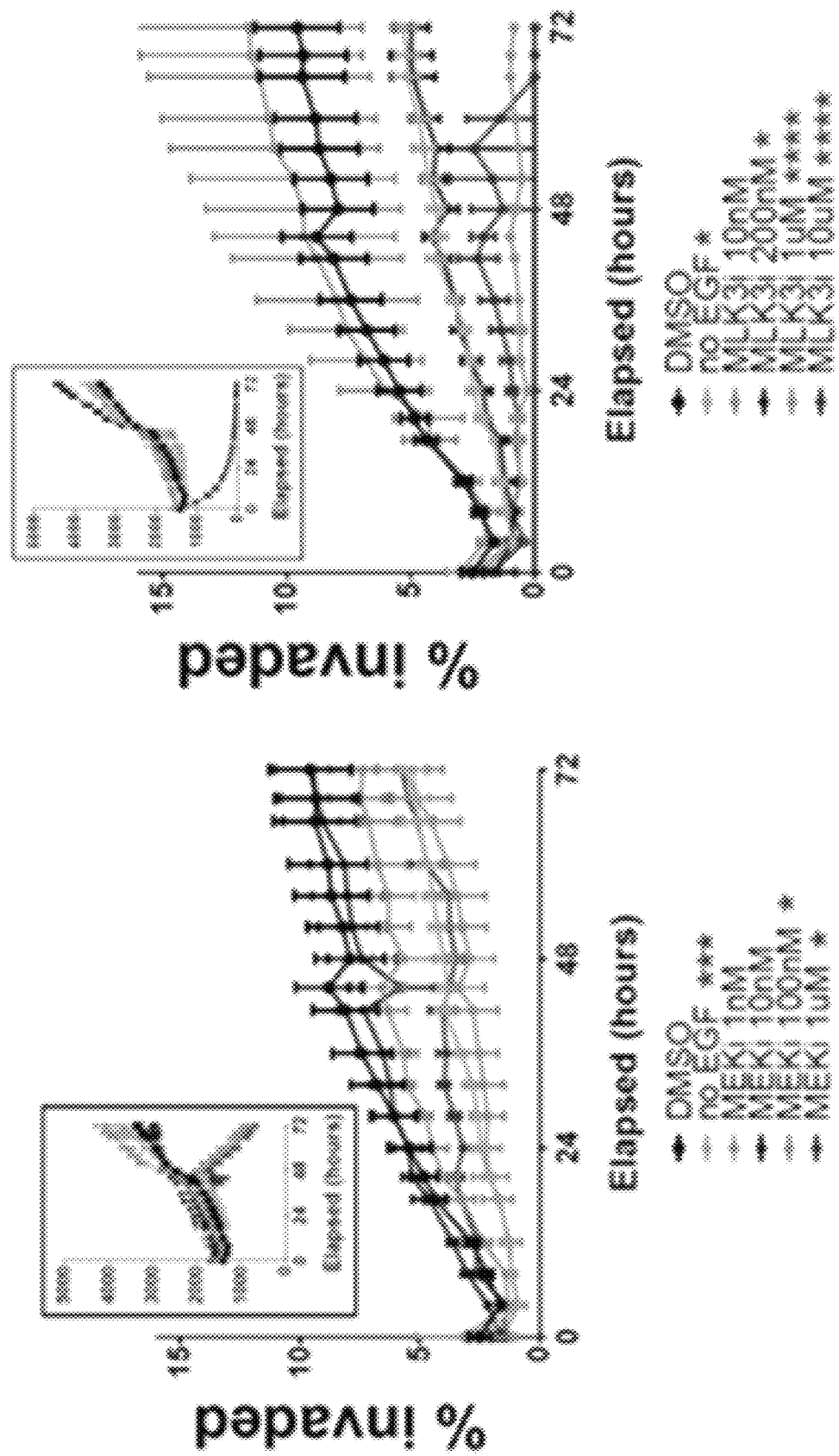

A high-throughput chemotactic invasion assay of nuclear-labeled BM1 cells (BM1-NucLight Red) was used to monitor invasion of cancer cells as well as their growth in 3D through a basement membrane extract. For each drug, except for CX-4945 and SW-538, there was a minimal dose at which the proliferation rates were unaffected while the invasive capabilities of the cells were at least partially blocked (FIG. 7A, 1 µM for SB203580 and SP600125, 1-10 nM for Trametinib, and 10-50 nM for URMC-099). Doses of CX-4945 and SW-538 (10 µM and above for each) that blocked invasion were also growth-inhibitory, suggesting that these drugs are unable to phenocopy selective RKIP suppression of invasion and metastasis. The drugs were then tested at these minimal dosages for their combinatorial effect on invasion.

Figure 6B:
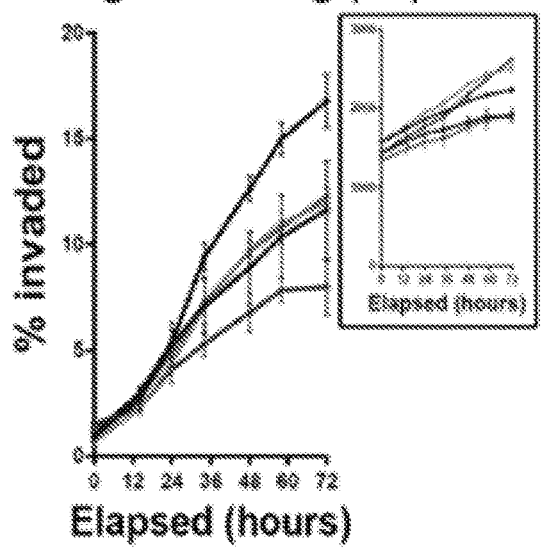
Figure 6B:
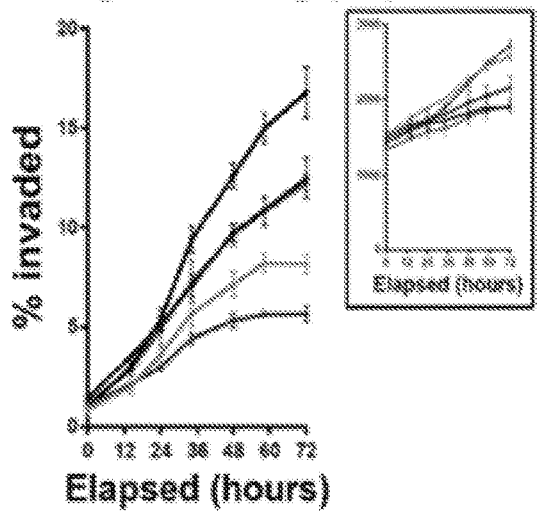
Figure 7B:
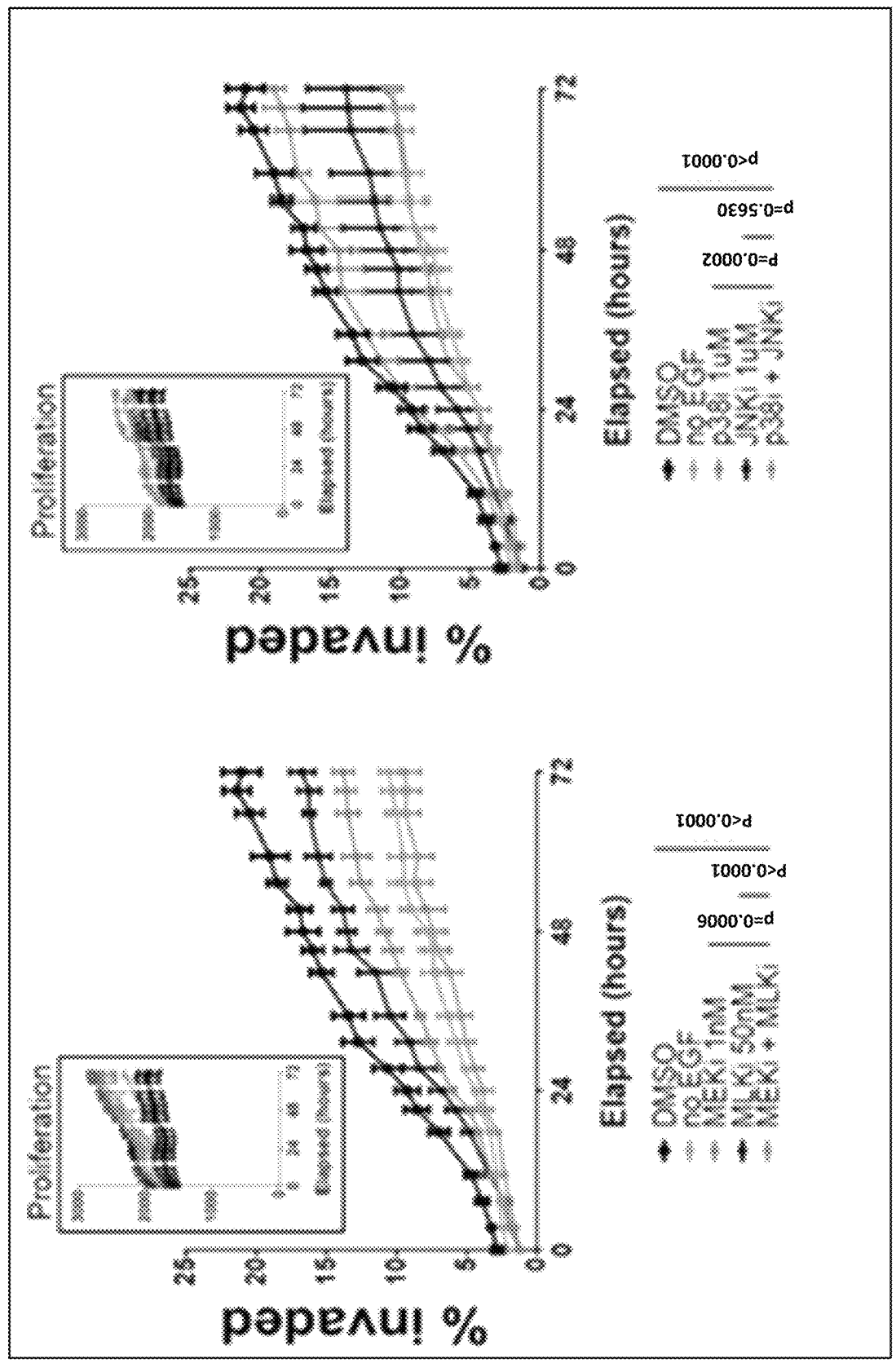
Figure 7B:
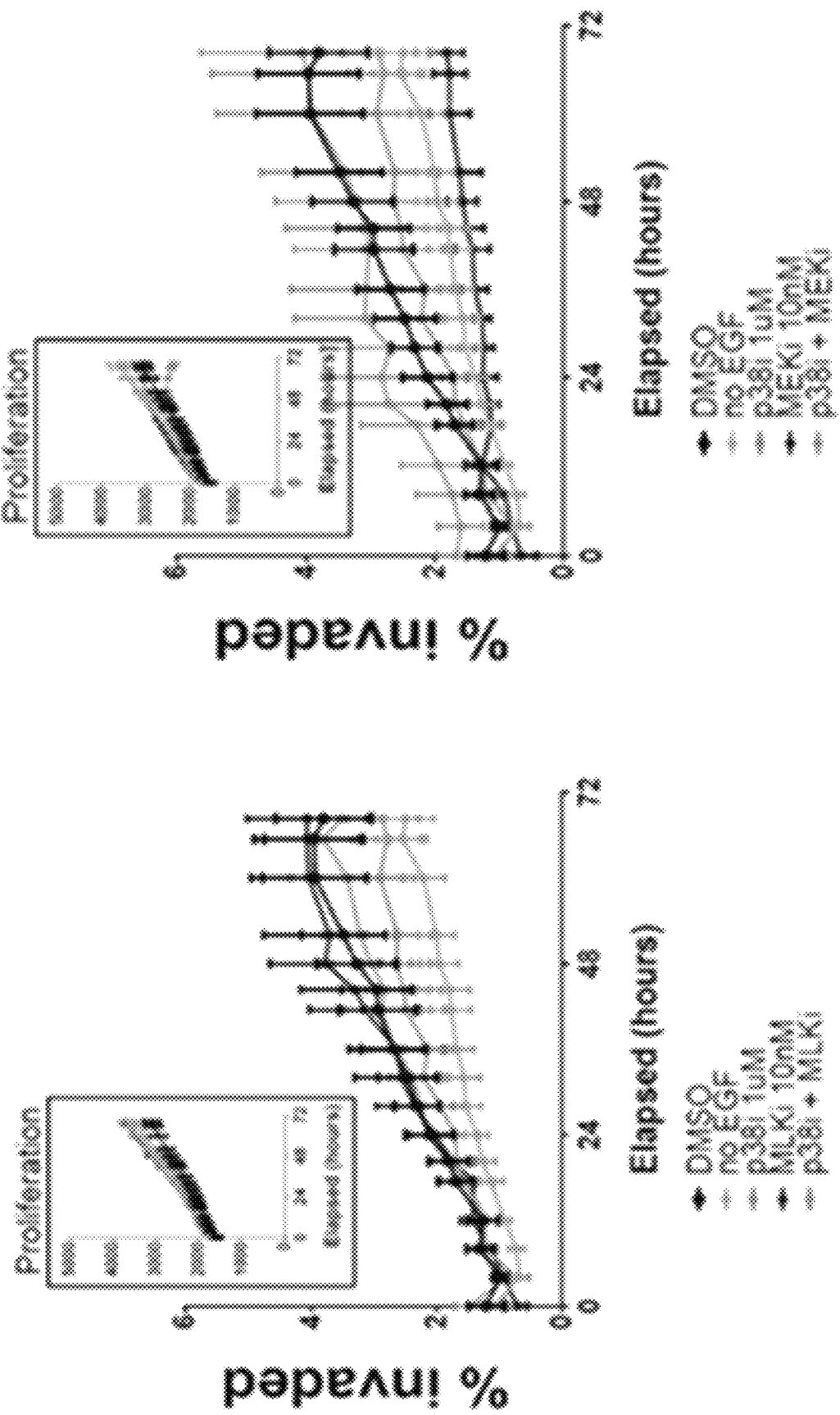
Figure 7C:
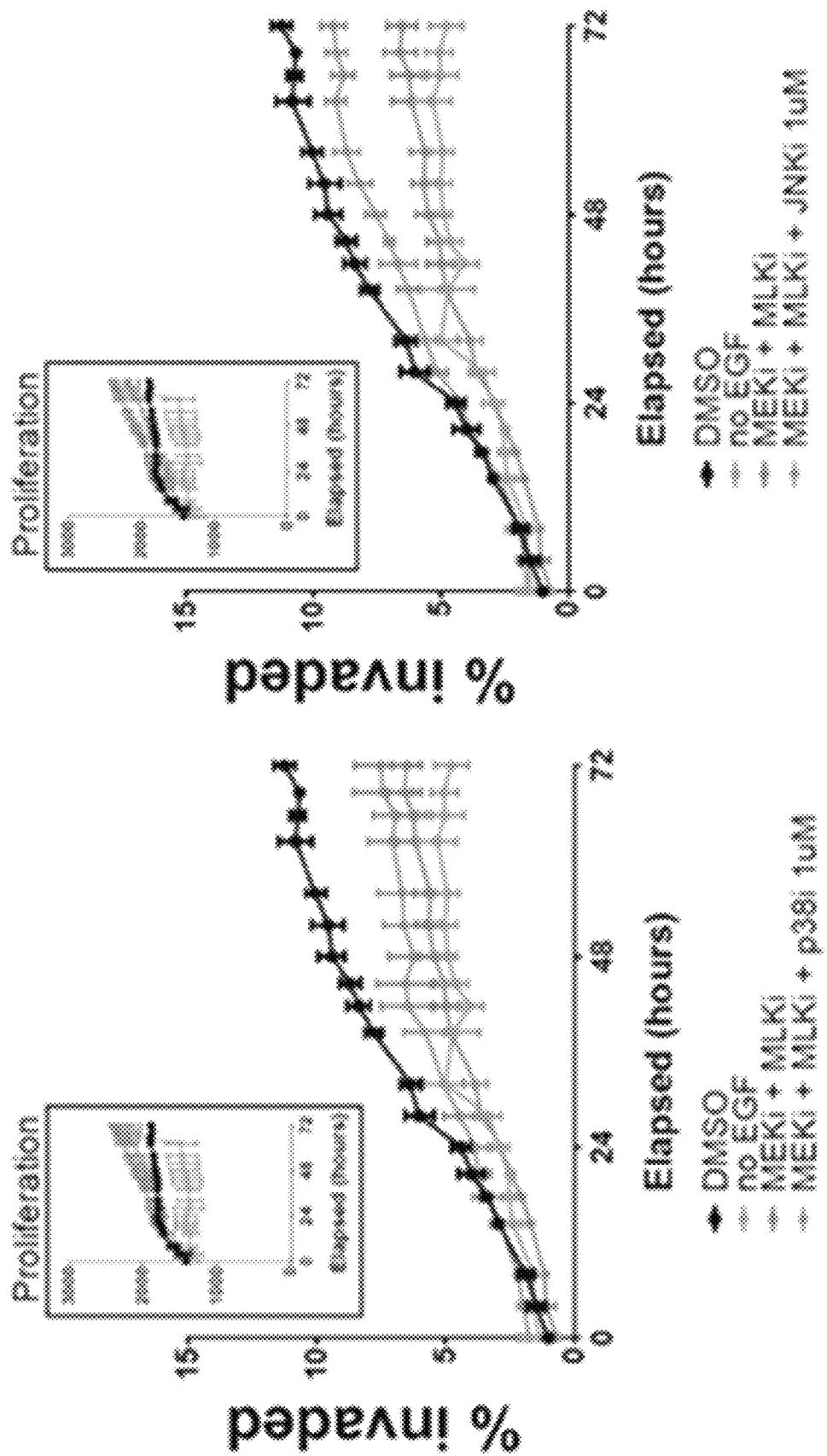
Figure 7C:
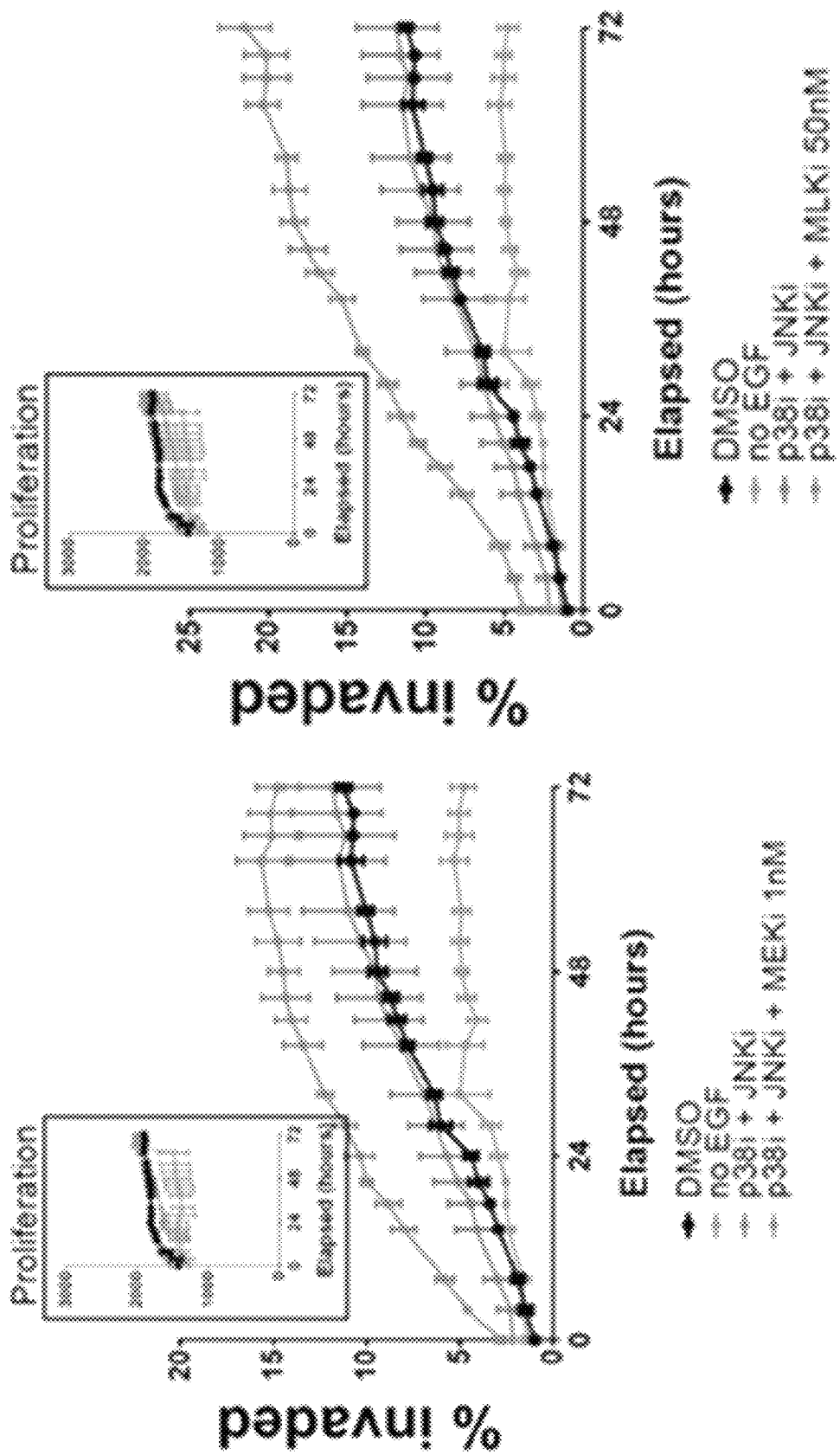

Out of all the dual combinations tested (FIG. 7B), only two demonstrated a putative combinatorial effect on invasion without a significant effect on proliferation: p38i (1

µM)+JNKi (1 µM) and MEKi (1 nM)+MLKi (50 nM) (FIG. 7B). Addition of a third inhibitor to these dual combinations did not improve the anti-invasive efficacy, demonstrating that combined effect of multiple MAPK inhibitors is not always additive (FIG. 7C). A four-drug combination consisting of p38i, JNKi, MEKi, and MLKi was more effective than either of the dual combinations and was not toxic to BM1 cells even when all the doses were doubled (FIG. 6B).

Figure 6C:
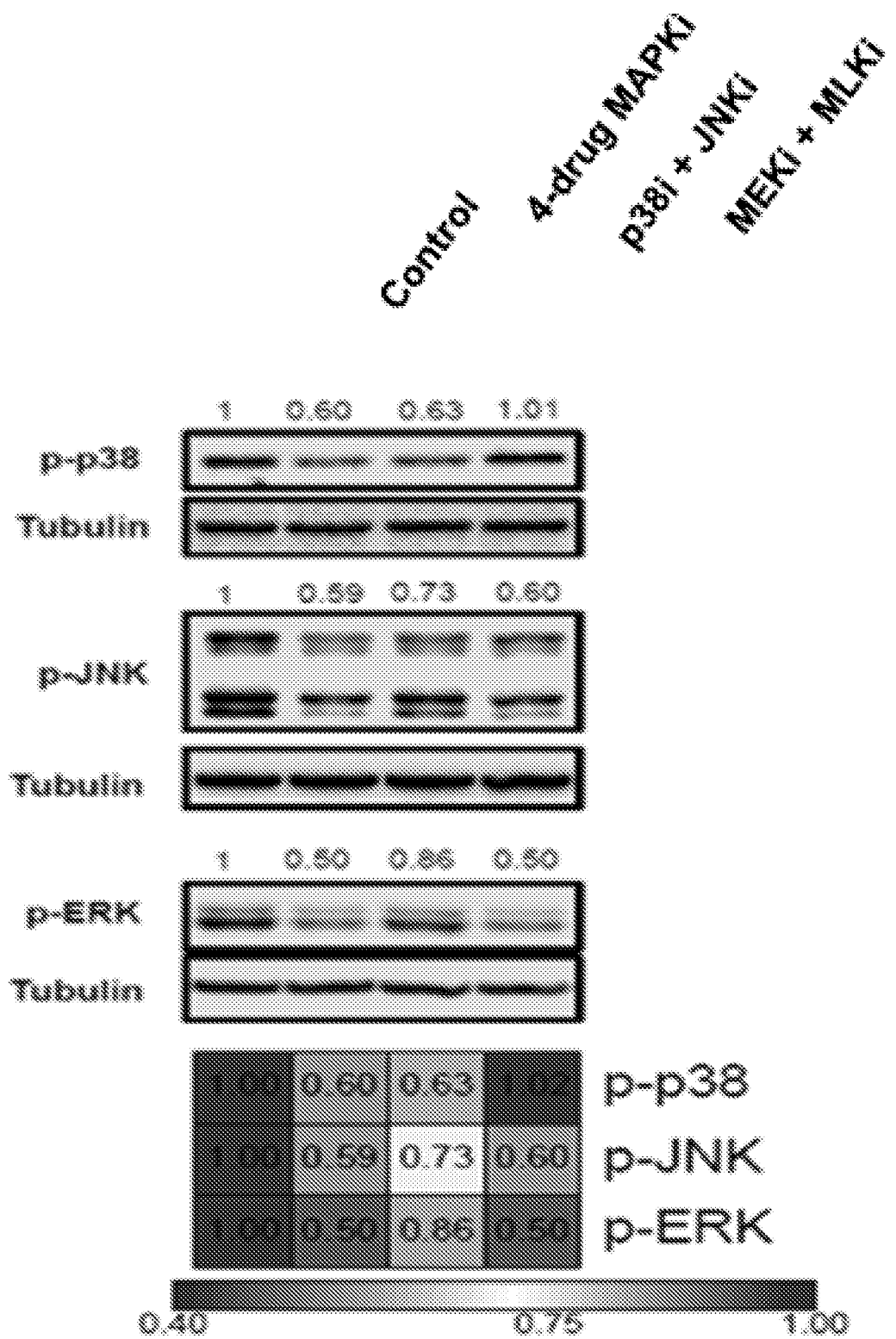
Figure 6D:
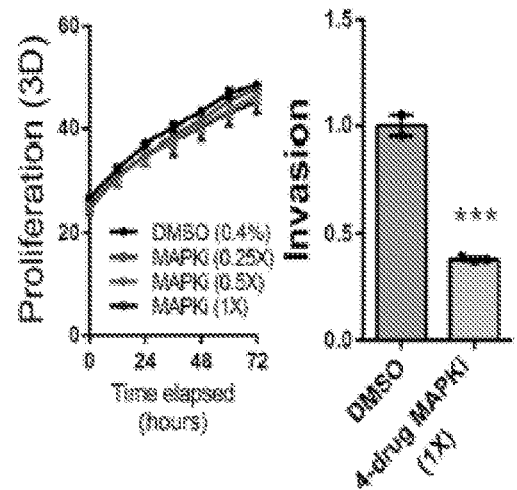
Figure 6D:
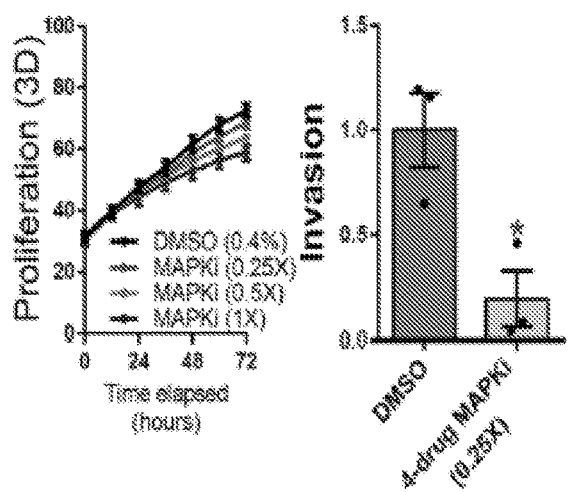
Figure 6D:
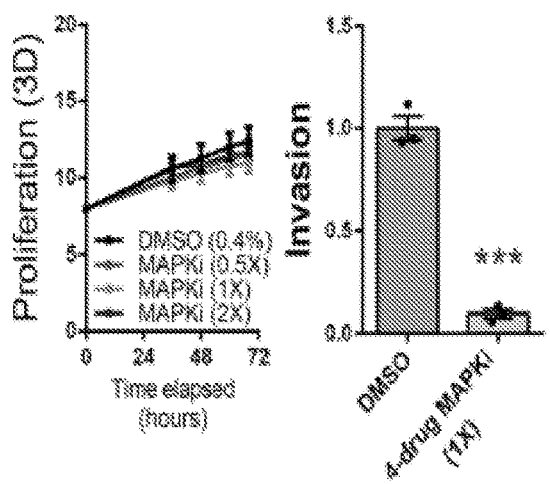
Figure 6E:
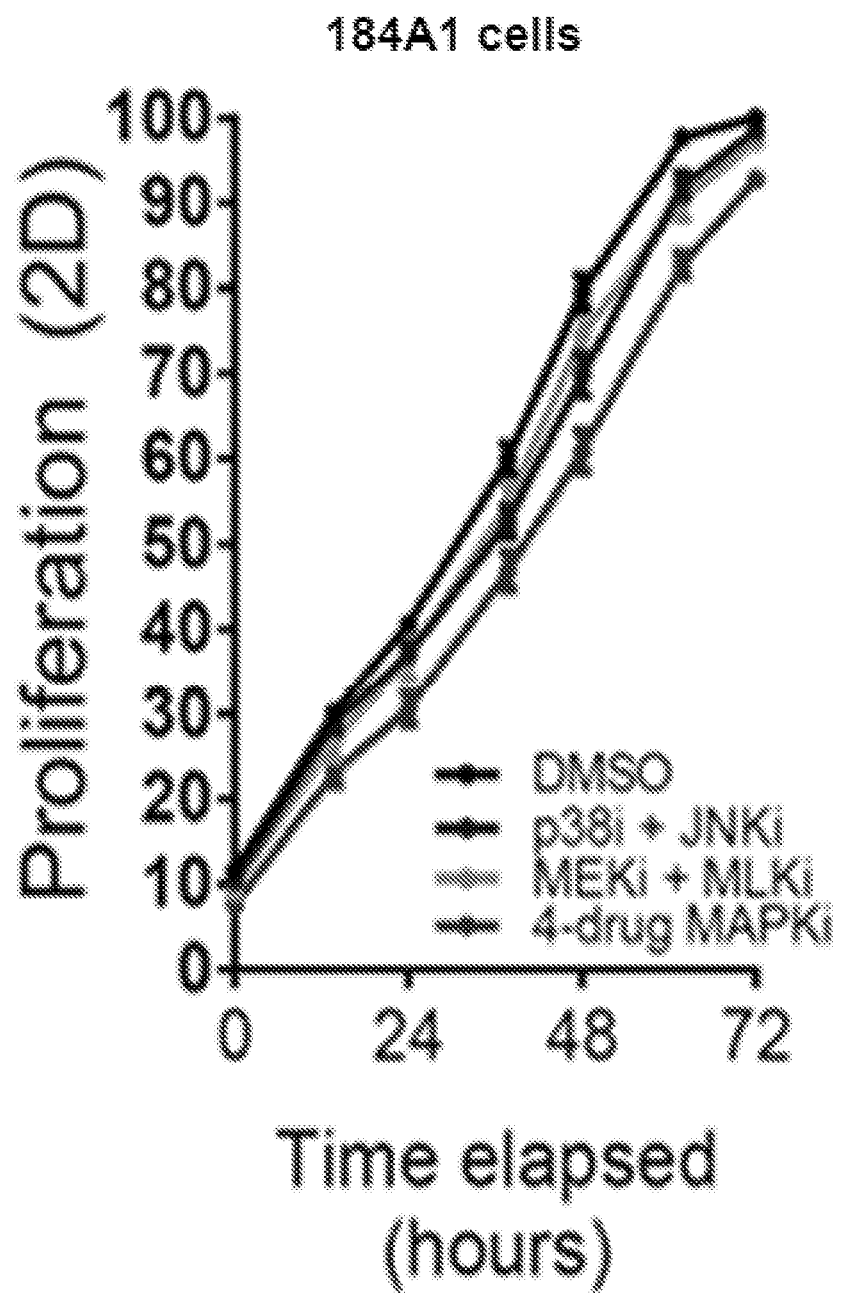
Figure 7D:
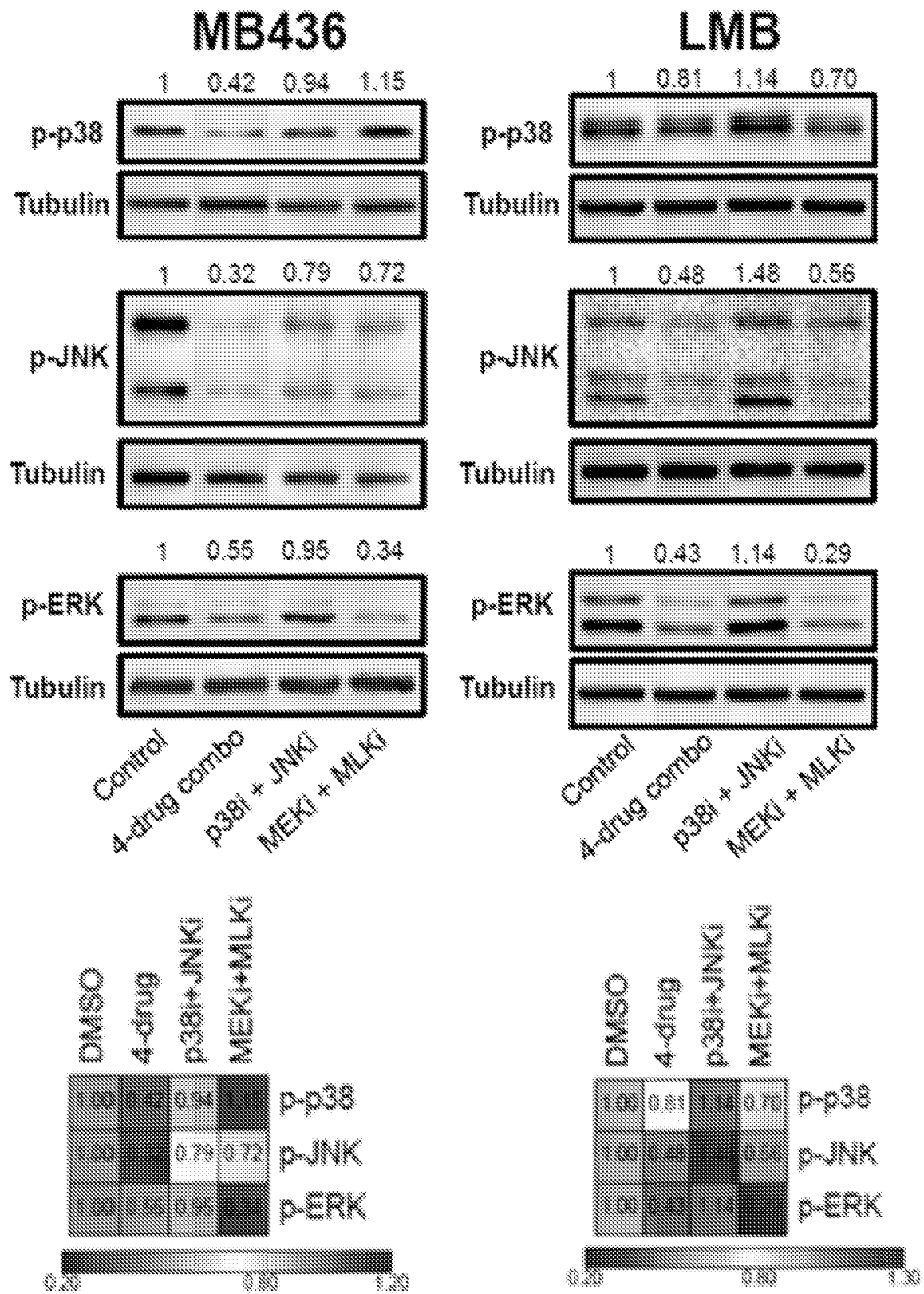
Figure 7E:
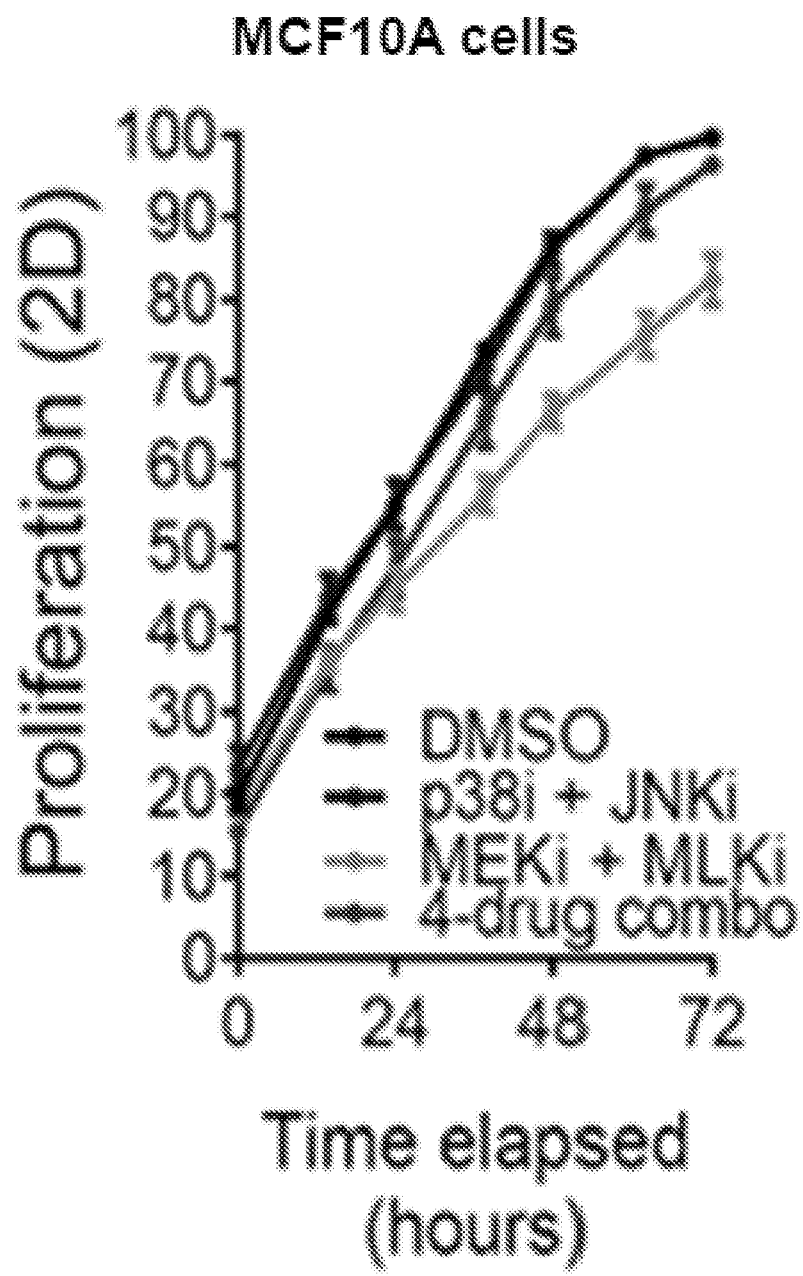

Signaling studies with the dual and 4-drug MAPK combinations showed that the 4-drug MAPKi combination (4D-MAPKi) was also more effective in blocking all three axes of MAPK signaling across multiple cell lines (FIGS. 6C and 7D). In addition to BM1 cells, the 4D-MAPKi inhibited invasion of human MB436 cells as well as mouse LMB and M6C cell at concentrations that do not affect 3D growth (FIG. 6D). Some cell lines were more sensitive to the treatment than others. Notably, 4D-MAPKi was not toxic to normal mammary epithelial cell lines and did not affect proliferation of non-transformed human 184A1 and MCF10A cells (FIGS. 6E and 7E). These findings suggest that 4D-MAPKi combination is an effective anti-invasive therapy that mimics RKIP inhibition of the MAPK family network without toxicity towards healthy cells.

Figure 9A:
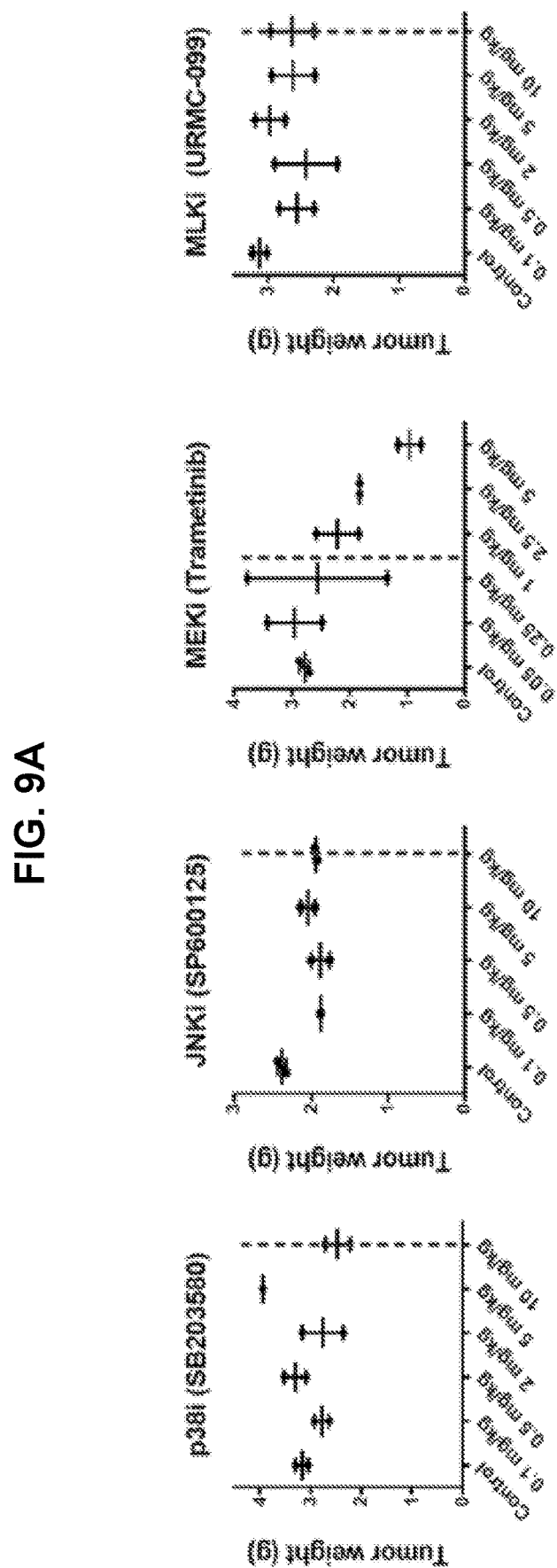
FIGS. 9A-9B: Effect of the individual MAPK inhibitors on tumor growth and their toxicity in combination. Related to FIGS. 8A-8F.

Example 4: The Four-Drug MAPKi Combination Blocks Metastatic Progression and Primary Tumor Growth in Vivo It was determined whether 4D-MAPKi blocks growth or metastasis of TNBC tumors in vivo. Using LMB cells in a syngeneic model, dose-response studies were performed with individual drugs to determine the highest dose at which growth of the primary tumor is unaffected. Inhibition of p38, JNK, or MLK up to 10 mg/kg did not affect growth of the orthotopic LMB tumors (FIG. 9A). MEK inhibitor decreased tumor growth in a dose-dependent manner, but had no significant effect at doses below 1 mg/kg. Based on this analysis, a 4D-MAPKi combination of 10 mg/kg for p38i, JNKi, MLKi, and 5 mg/kg for MEKi (1×) was chosen for in vivo studies.

Figure 8A:
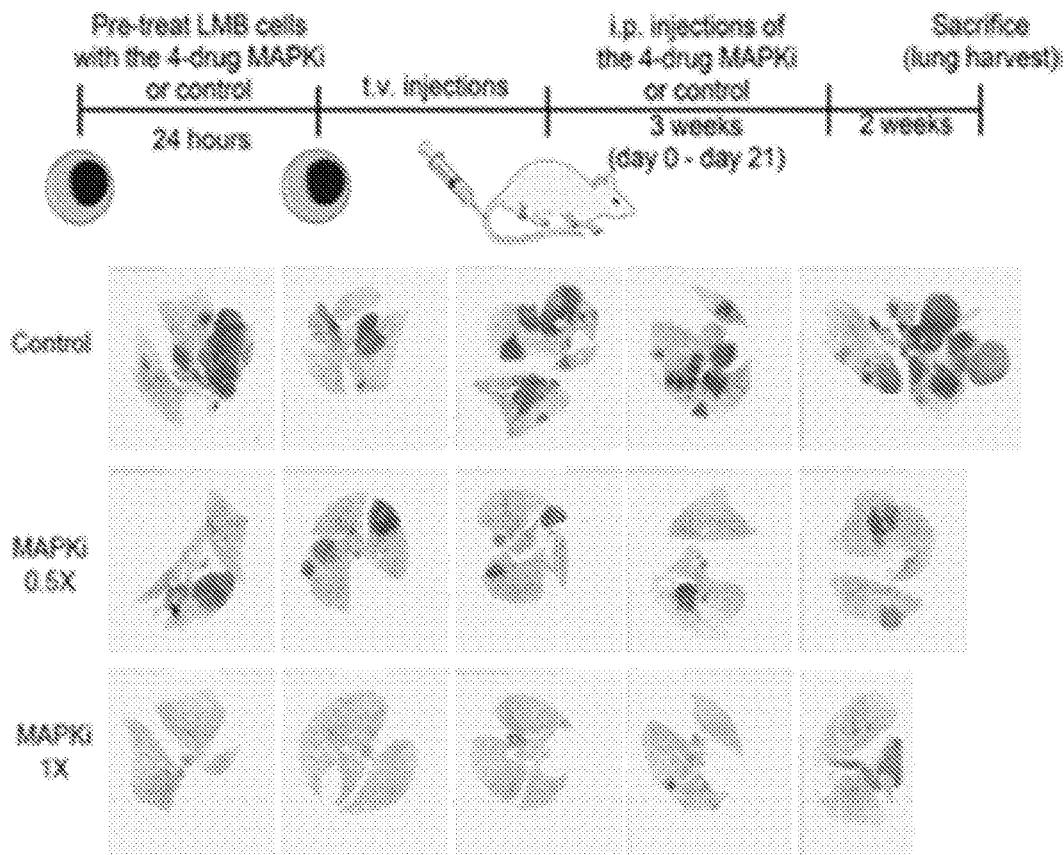
FIGS. 8A-8F: MAPKi combination blocks metastatic progression and primary tumor growth in vivo.
Figure 8A:
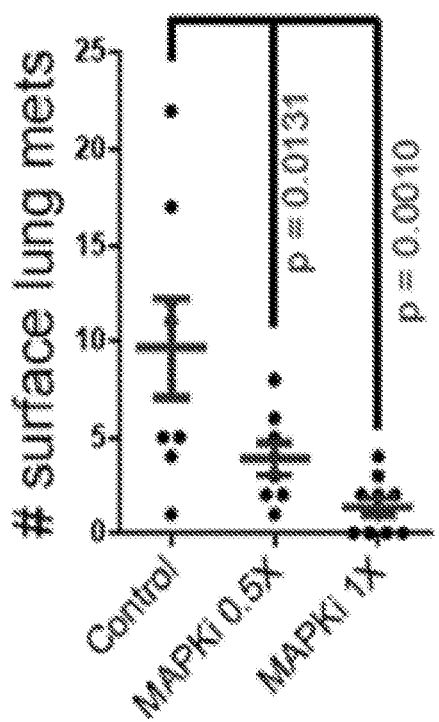
Figure 8C:
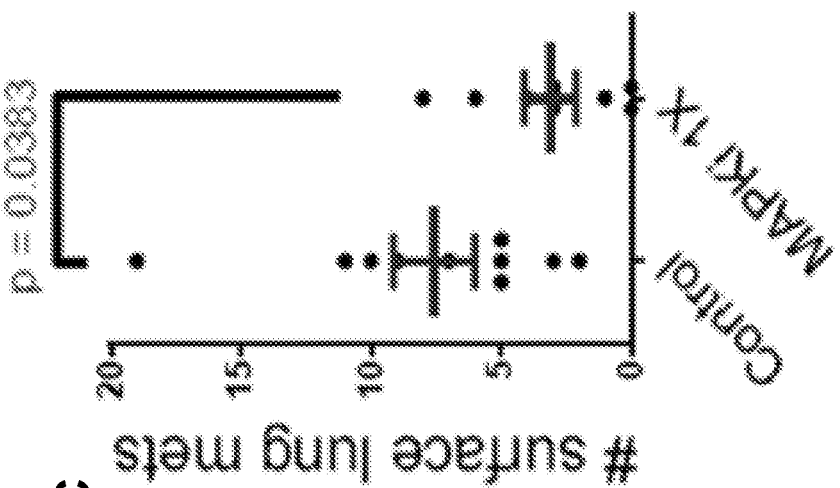
Figure 8B:
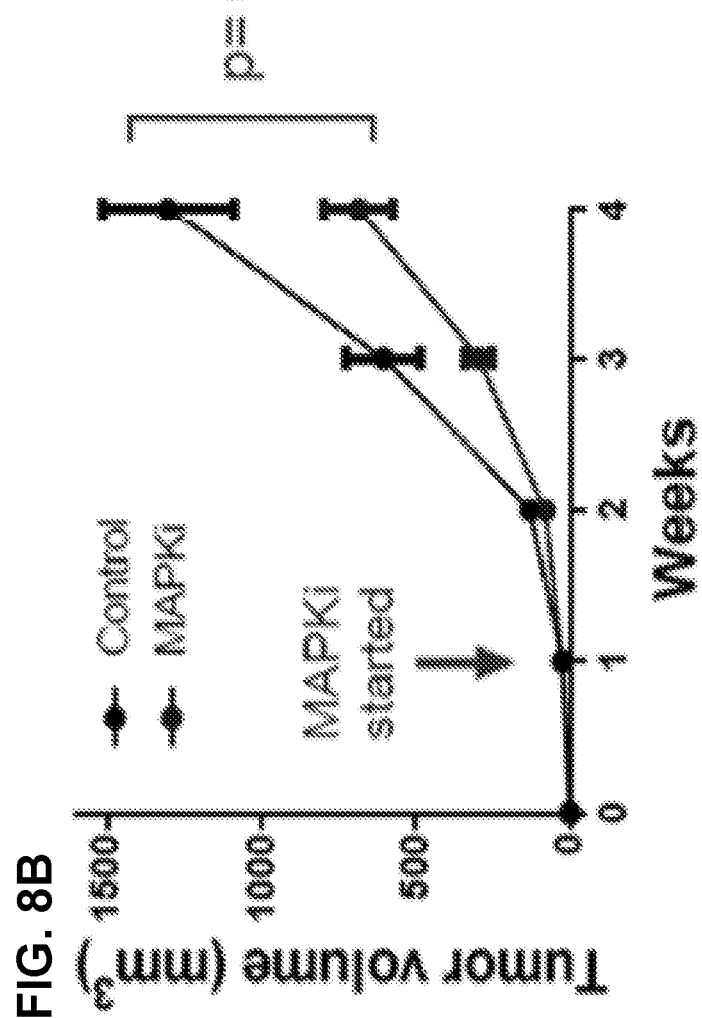
Figure 8D:
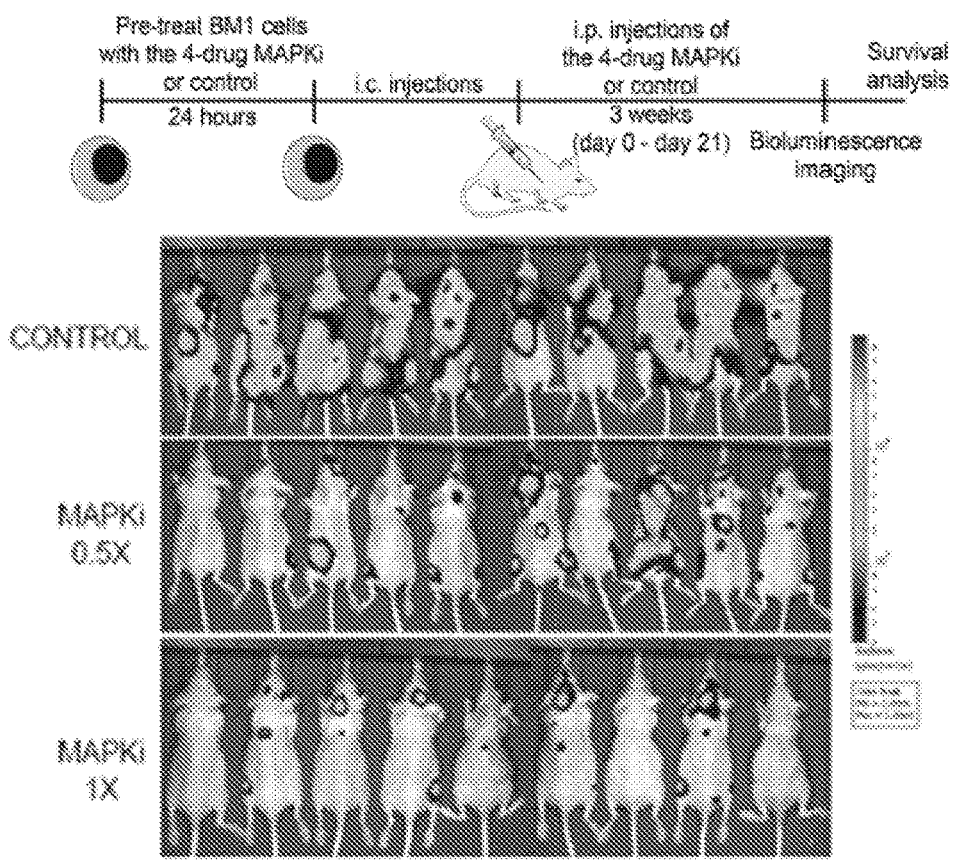
Figure 8D:
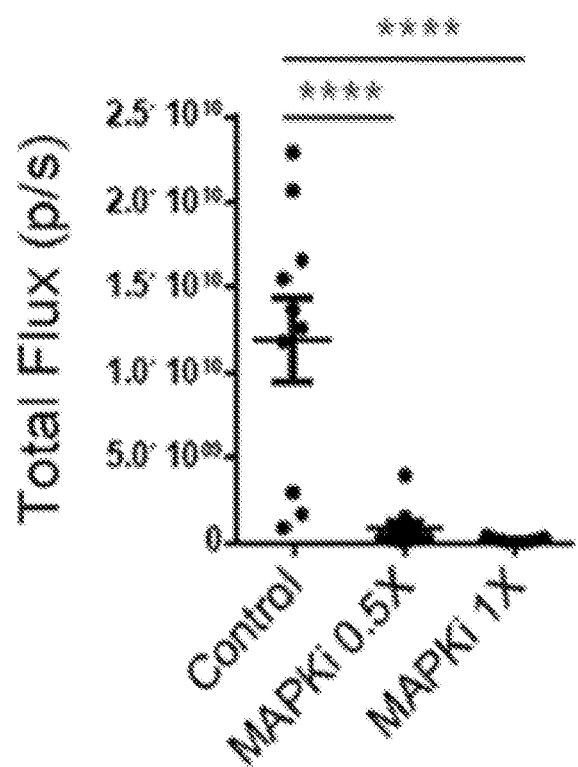
Figure 8E:
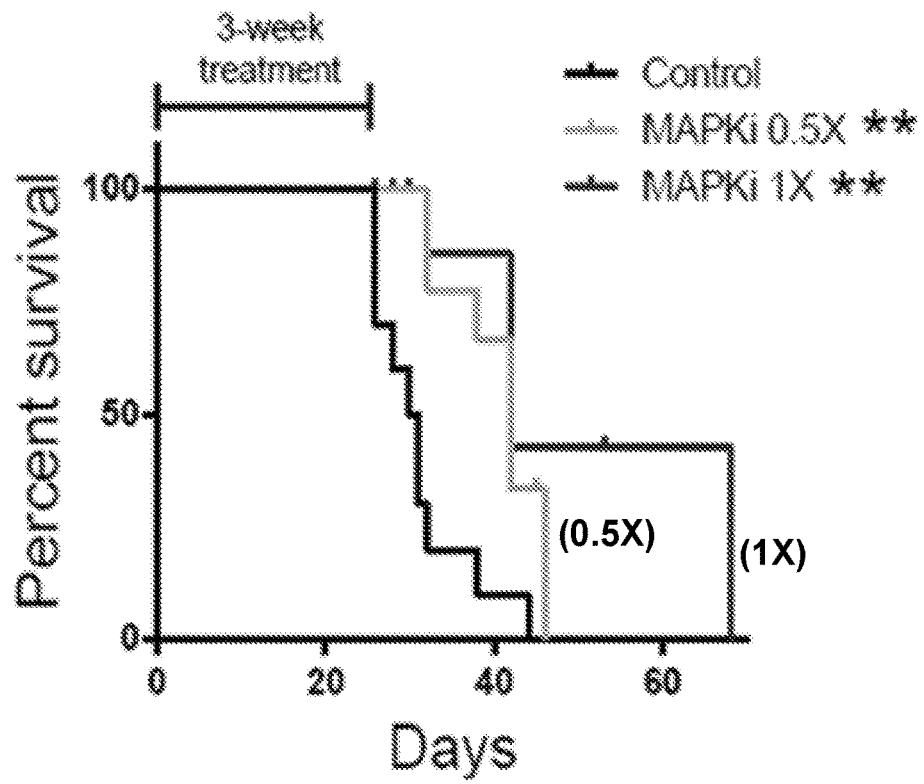
Figure 8F:
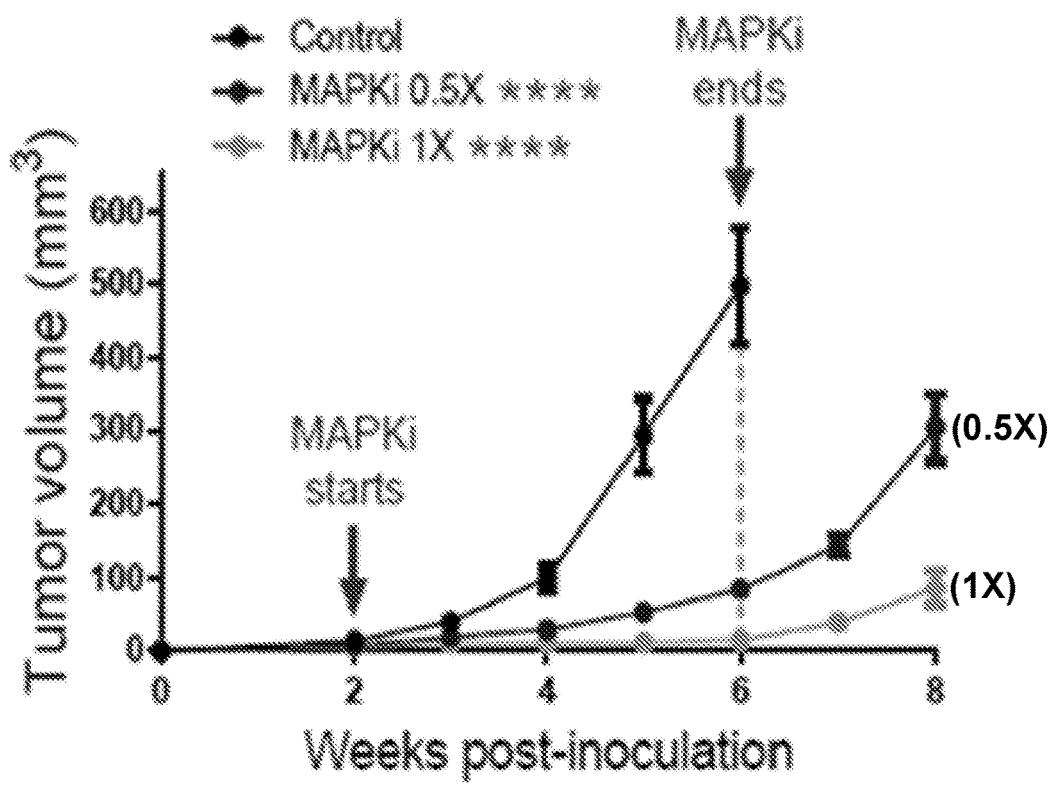
Figure 9B:
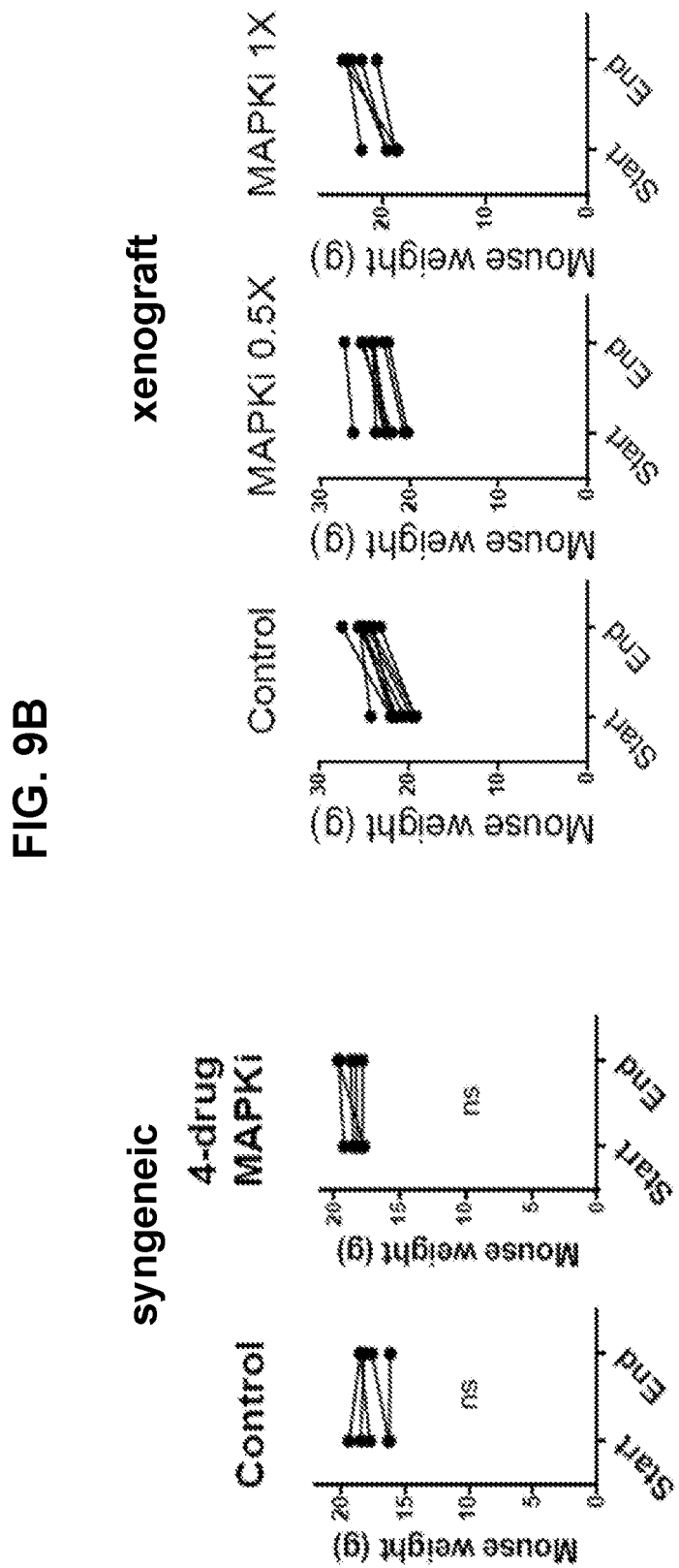

The undiluted (1×) and diluted (0.5×) 4D-MAPKi suppressed metastatic lung colonization in the syngeneic LMB tumors in a dose-dependent manner (FIG. 8A). At the 1×dose, the MAPKi combination also partially inhibited primary LMB tumor growth (FIG. 8B). To determine the stage of inhibitor action, mice were treated for only 2 days upon inoculation. This treatment still caused significant reduction in the overall metastatic burden, suggesting that the inhibitor combination acts to block early extravasation and tissue invasion steps of metastasis rather than colonization (FIG. 8C). Xenograft BM1 tumors were more sensitive to the MAPKi treatment than LMB tumors, as even the half dose (0.5×) potently inhibited bone metastasis of luciferase-expressing BM1 cells. (FIG. 8D). Metastasis-bearing mice treated with the MAPKi combination for 3-weeks showed improved survival even after the cessation of the treatment (FIG. 8E) Similarly, the MAPKi combination potently inhibited primary BM1 tumor growth in a dose-dependent manner, but the tumor growth resumed upon treatment cessation (FIG. 8F). This suggests that the MAPKi combination might be more effective as a continuous treatment. No toxicity due to the 4-drug combination in either the syngeneic or the xenograft models was observed, since the mice retained the same body weight throughout the treatment (FIG. 9B). These findings indicate that the MAPKi combination can act as both tumor and metastasis suppressor in TNBCs and has the potential to prevent recurrence with continued treatment. These data indicate that targeting the complete MAPK network at subthreshold doses for inhibiting tumor growth is an effective anti-metastatic and pro-survival strategy.

Figure 10A:
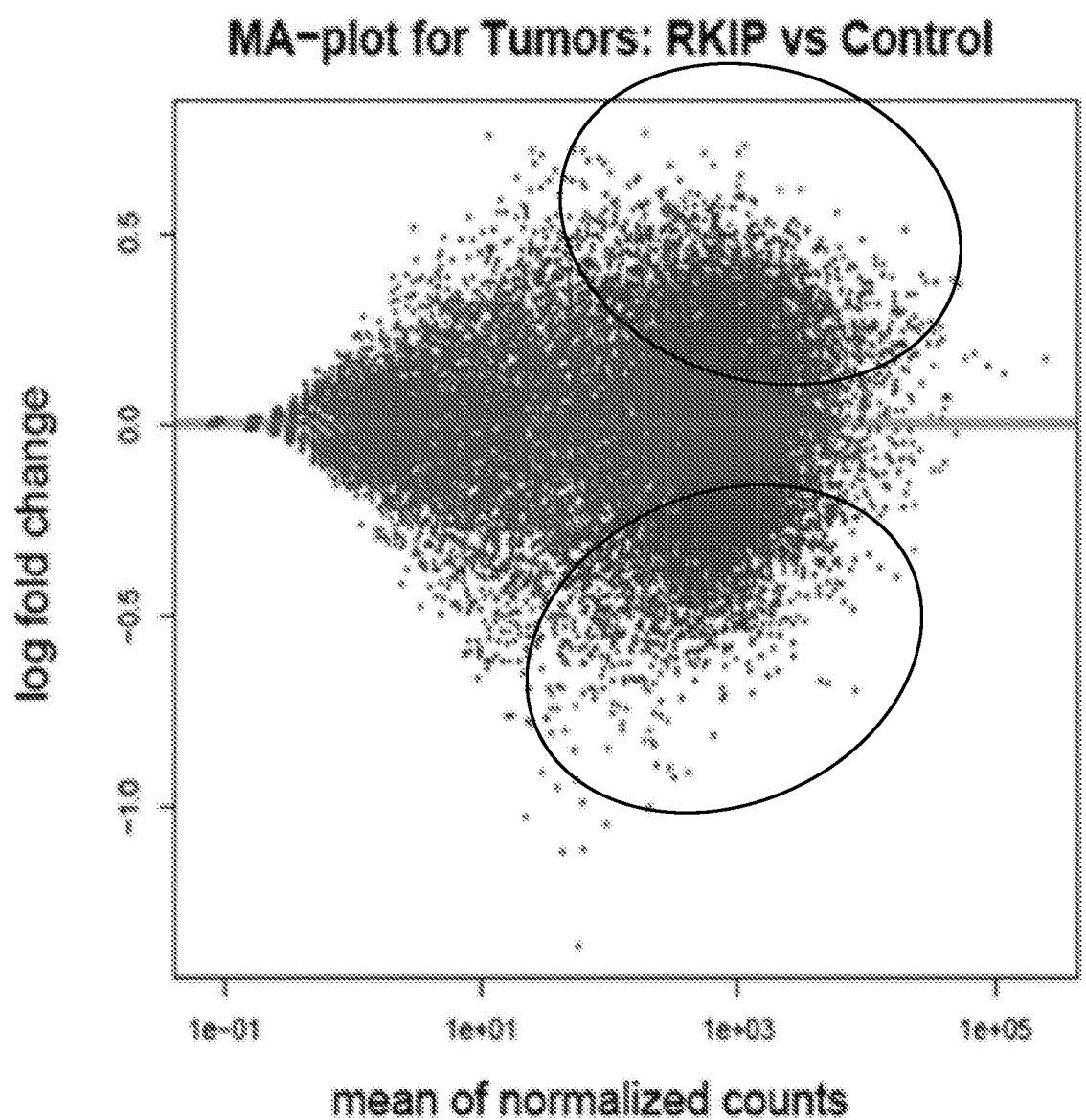
FIGS. 10A-10E: Both RKIP and the MAPKi combination downregulate clinically-relevant motility and invasion genes.
Figure 11A:
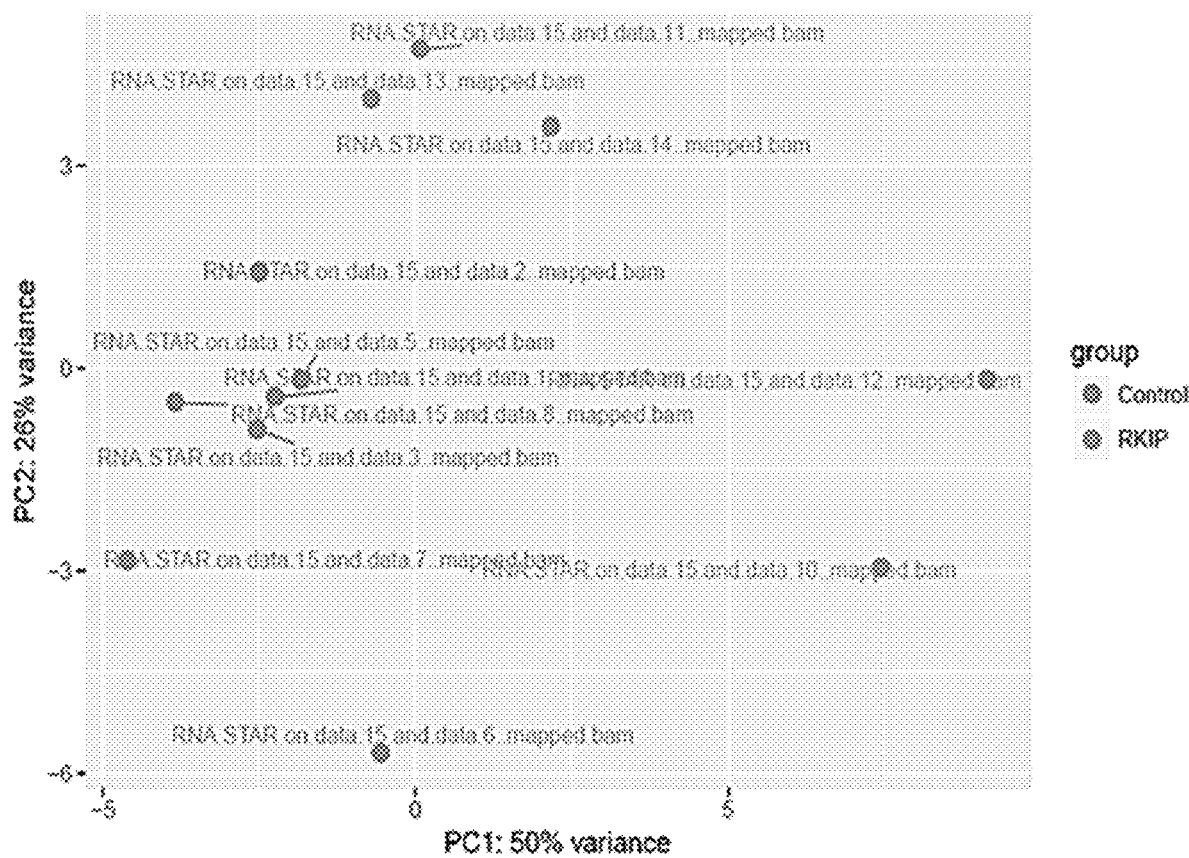
Figure 11B:
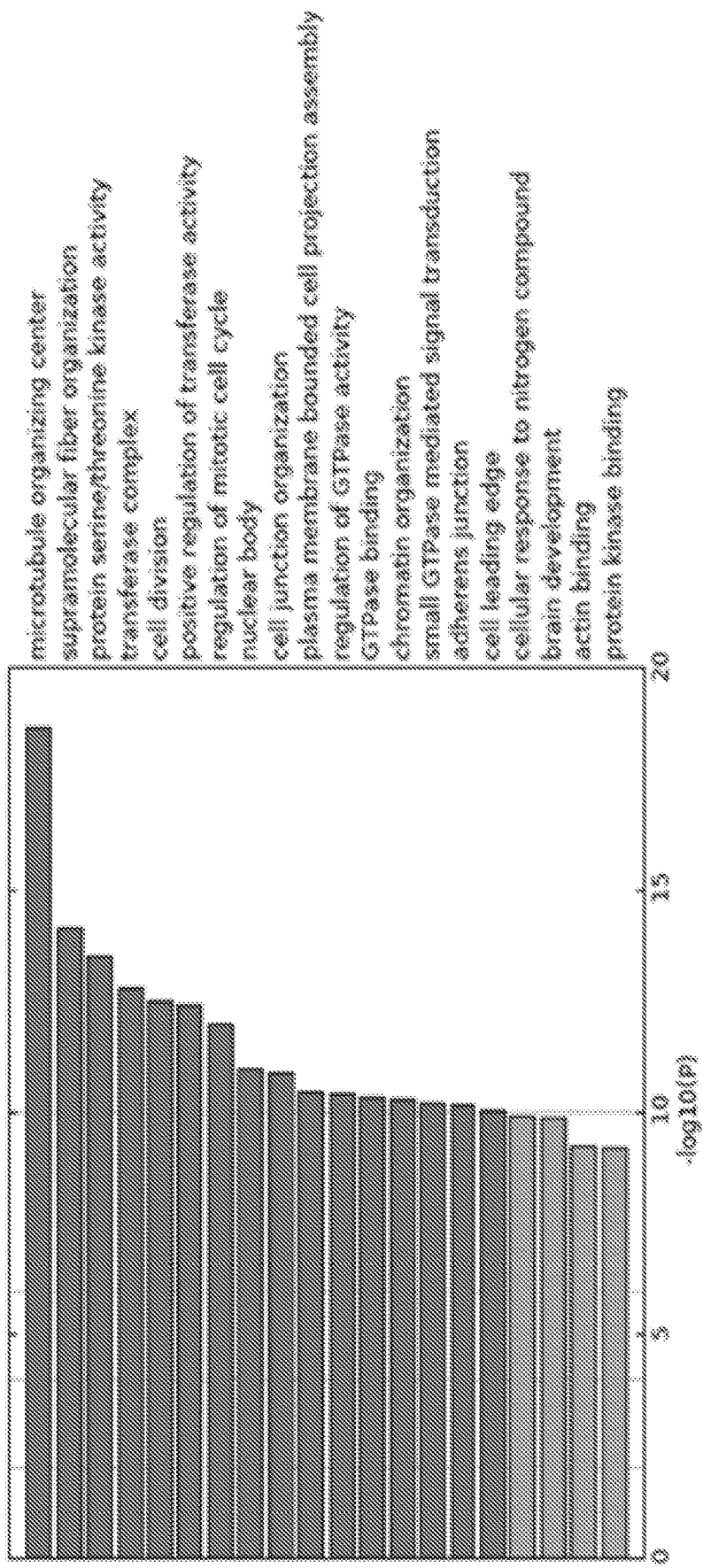

Example 5: Both RKIP and the MAPKi Combination Downregulate Clinically-Relevant Motility and Adhesion Genes Since both RKIP and 4D-MAPKi block tumor cell extravasation and metastatic colonization, it's possible that their common targets are required for metastatic progression. To identify downstream targets of RKIP, control or RKIP-expressing human xenograft tumors were analyzed by RNA sequencing. Principal component analysis revealed two discrete tumor clusters dependent upon RKIP expression (FIG. 11A). RKIP downregulated roughly 2800 genes some of which fall into functional categories related to cell movement (cytoskeletal organization, cell-substrate adhesion, cell leading edge) and kinase-mediated signal transduction (FIGS. 10A and 11B), consistent with a role for RKIP as a kinase inhibitor that suppresses invasion and metastasis.

Figure 10B:
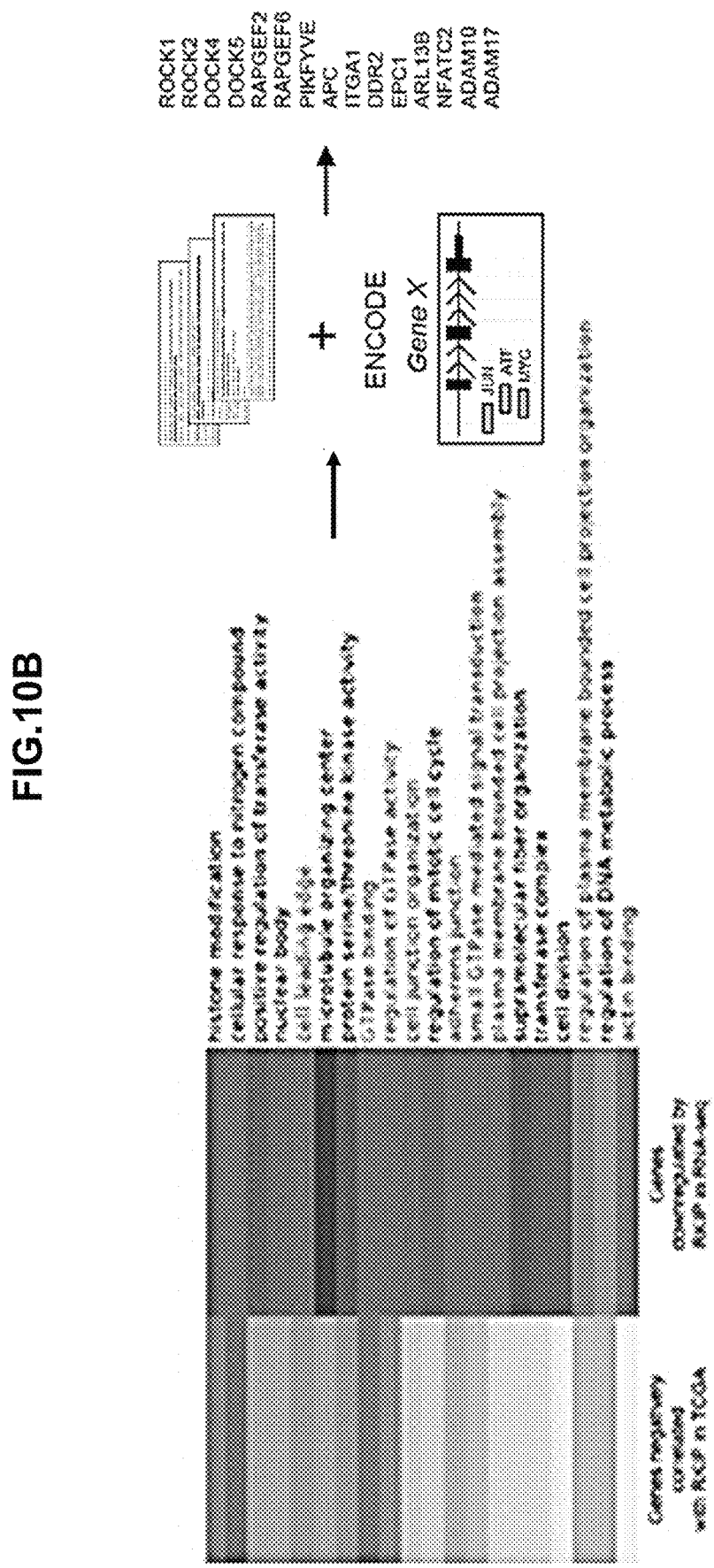
Figure 10C:
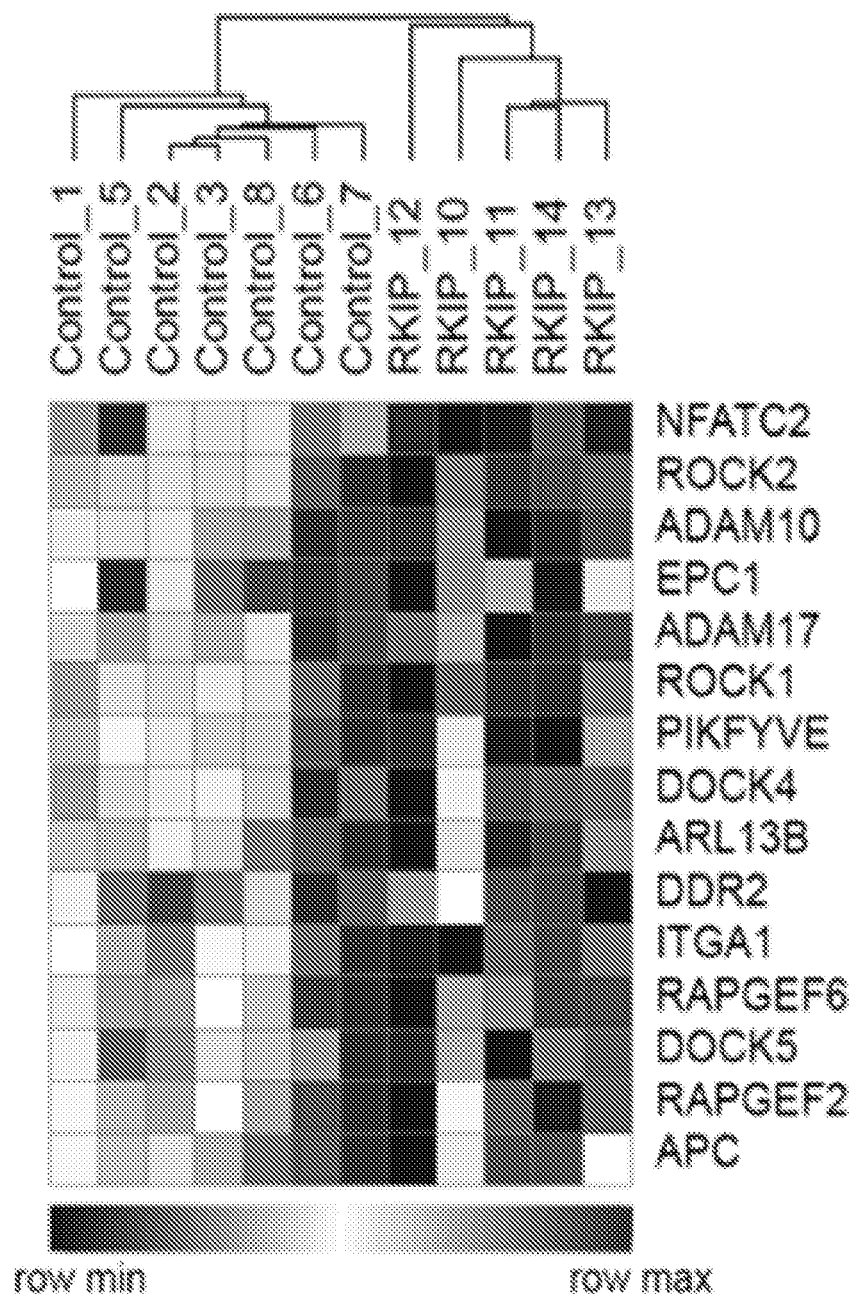
Figure 10D:
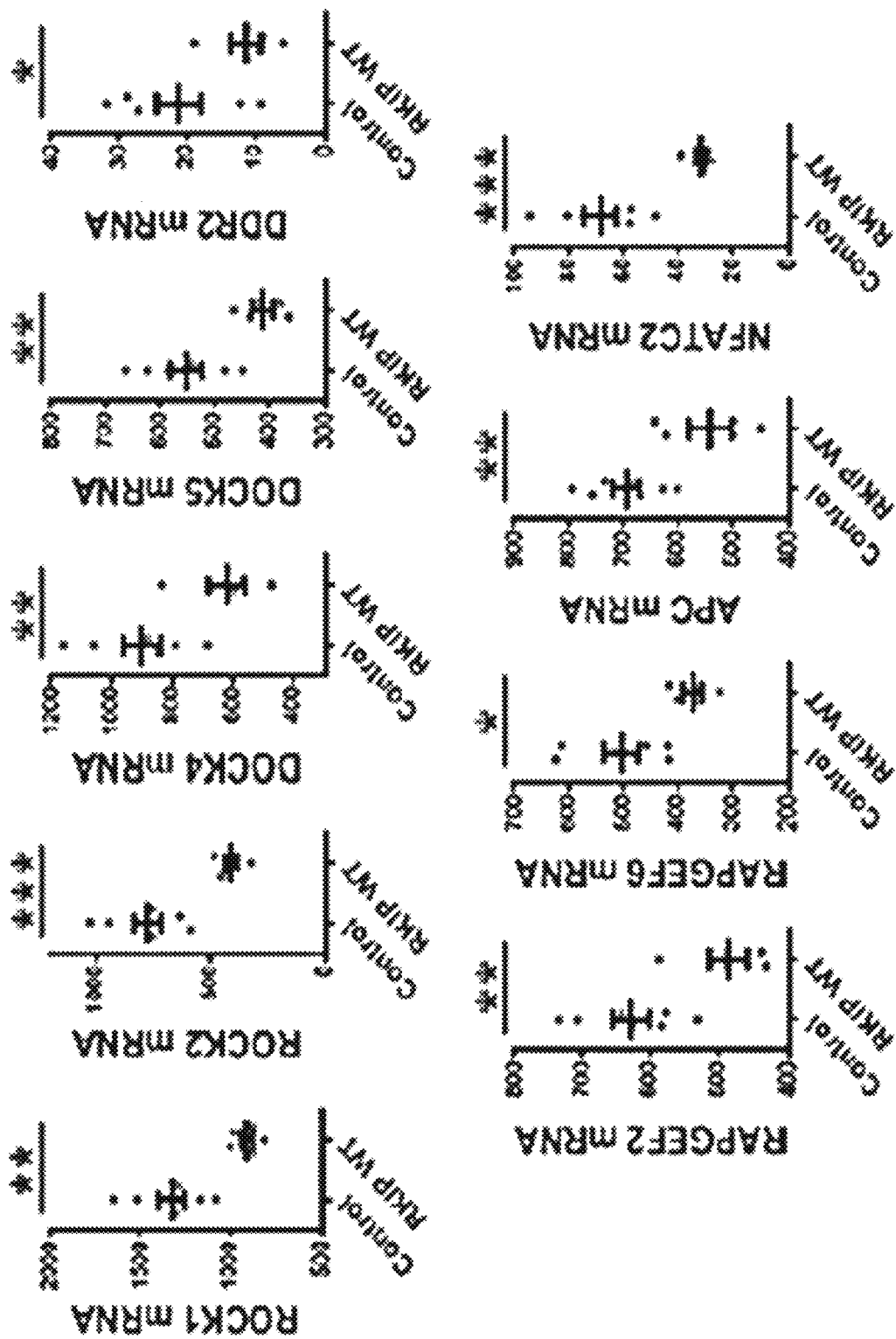
Figure 11D:
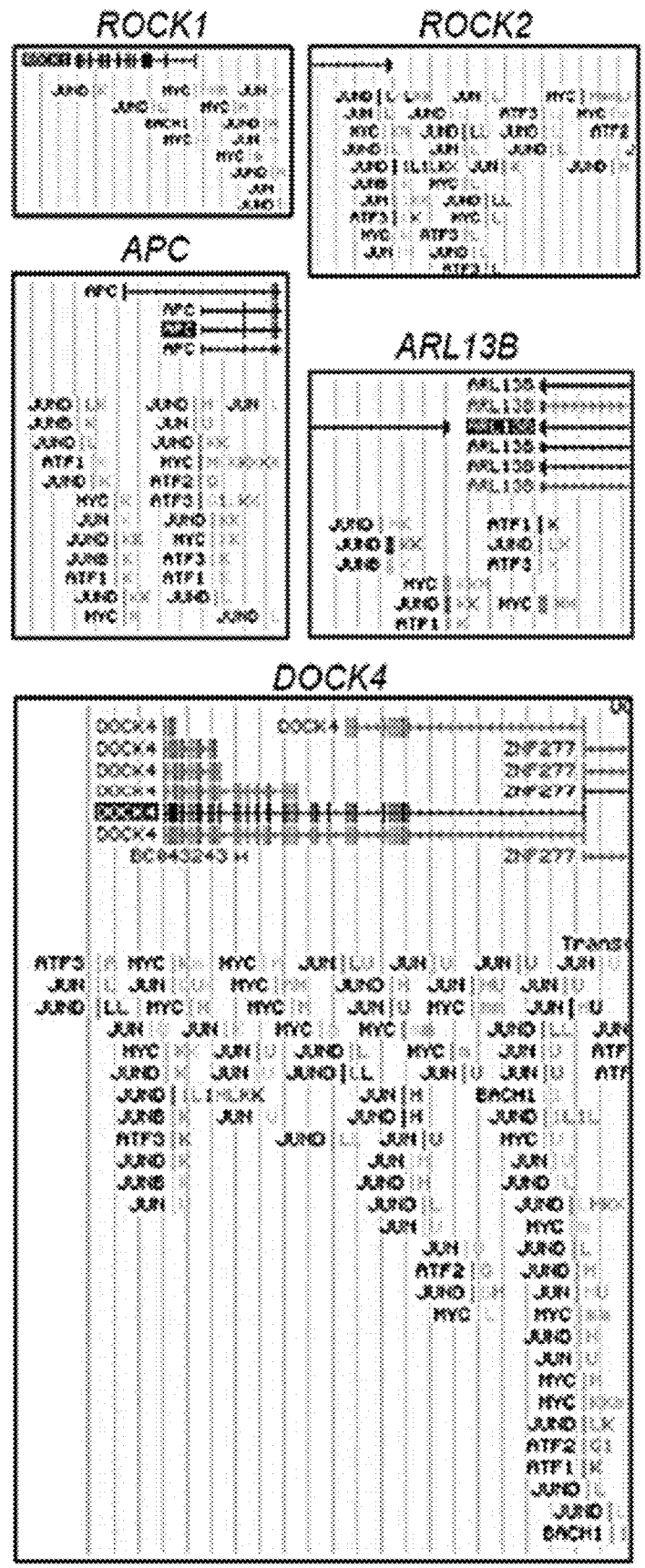

To assess the clinical relevance of these genes, they were compared to the set of genes whose expression is inversely correlated to RKIP in the TCGA breast cancer database (Pearson/Spearman cutoff=0.3). In both gene sets, similar functional categories were identified (FIG. 10B). At least 78 genes related to cell movement and kinase signaling overlapped between the TCGA and RNAseq datasets. Interest was in metastatic genes that are induced by the stress MAPK network, and the focus was on genes that (1) have been previously shown to promote metastatic pathways and (2) have potential binding sites for MAPK-regulated transcription factors as demonstrated by ENCODE (ENCODE Project Consortium, 2012). Fifteen putative RKIP target genes were identified (ROCK1, ROCK2, DOCK4, DOCK5, RAPGEF2, RAPGEF6, NFATC2, DDR2, PIKFYVE, APC, ITGA1, ARL13B, ADAM10, ADAM17, and EPC1) that met these criteria (FIG. 10B-D). These genes have been implicated in metastasis and have binding sites for ATFs and JUNs, two families of transcription factors activated by p38 and JNK, respectively, as well as MYC, a downstream mediator of ERK signaling (FIGS. 11C and 11D).

Figure 10E:
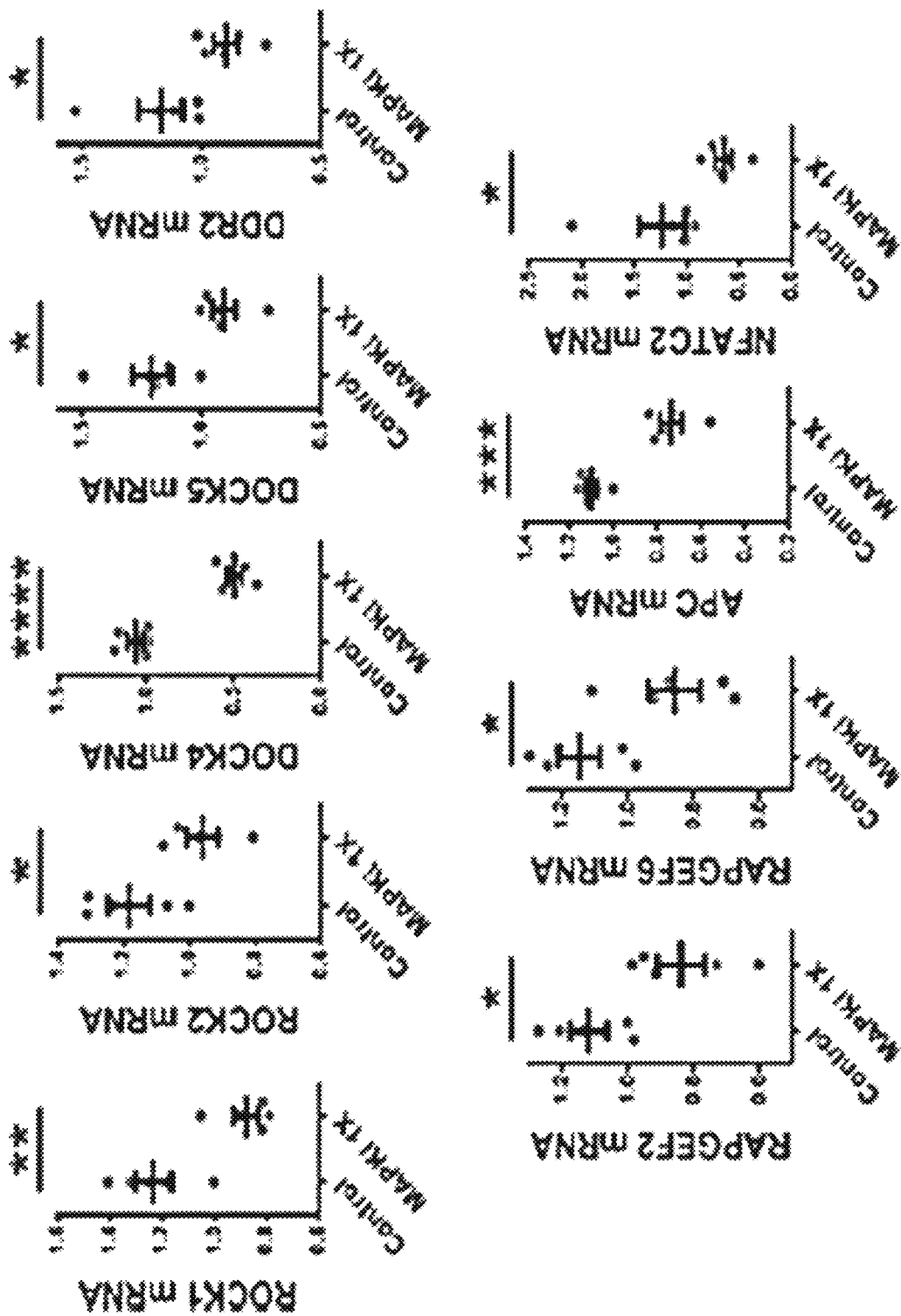
Figure 11E:
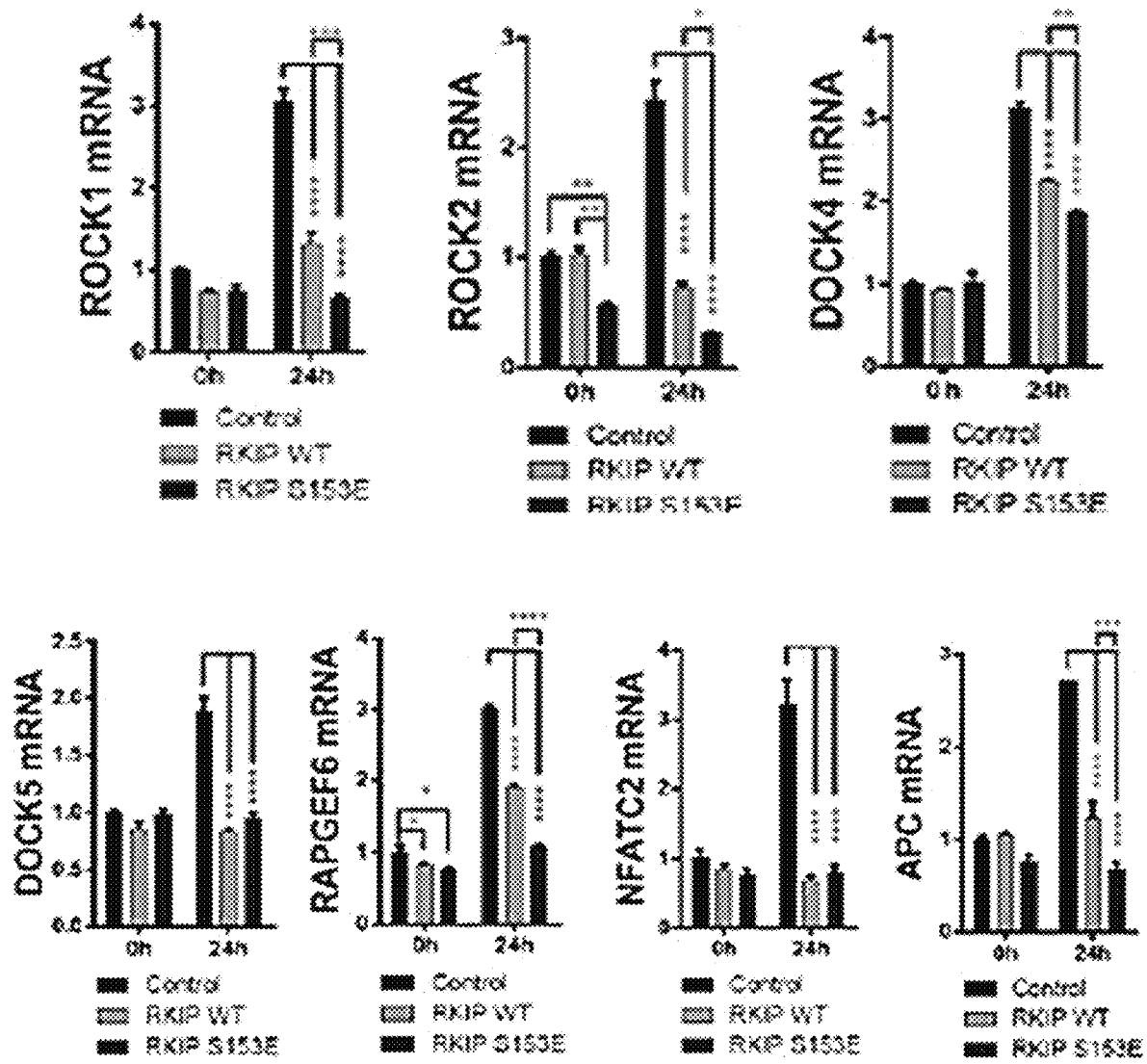
Figure 11F:
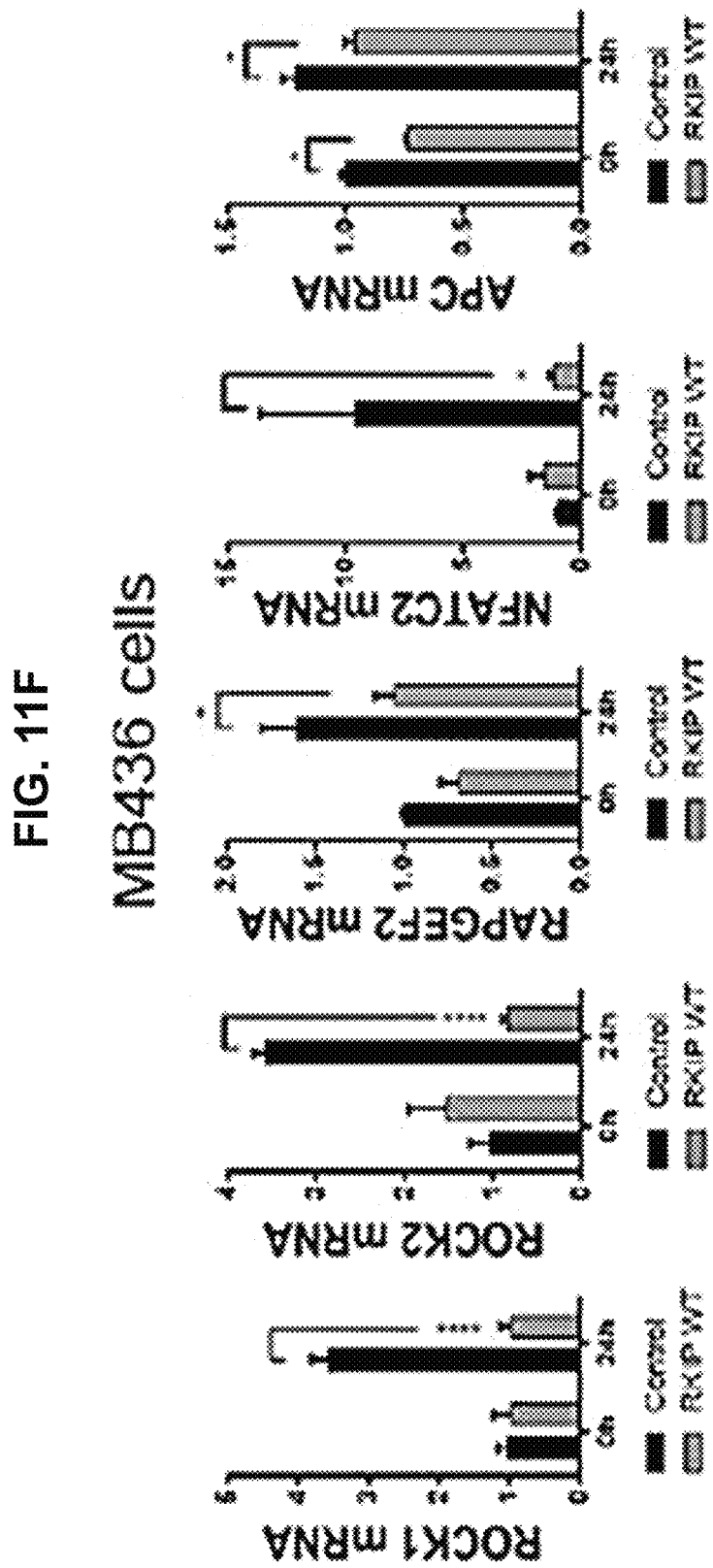

A significant fraction of these motility/adhesion genes were induced by anisomycin stress in human TNBC cells in vitro, and RKIP or RKIP S153E expression blocked their induction (FIGS. 11E and 11F). 4D-MAPKi similarly inhibited expression of these genes under stress conditions in both cells and syngeneic tumors (FIGS. 10E and 11G), highlighting its ability to phenocopy RKIP. By contrast, the 2-drug combinations were ineffective (FIG. 11G). These results reveal a mechanism whereby RKIP suppresses breast cancer metastasis by inhibiting a MAPK signaling network that transcriptionally activates metastatic genes.

Example 6: Regulation of Motility/Adhesion Genes by RKIP Involves BACH1

Figure 12D:
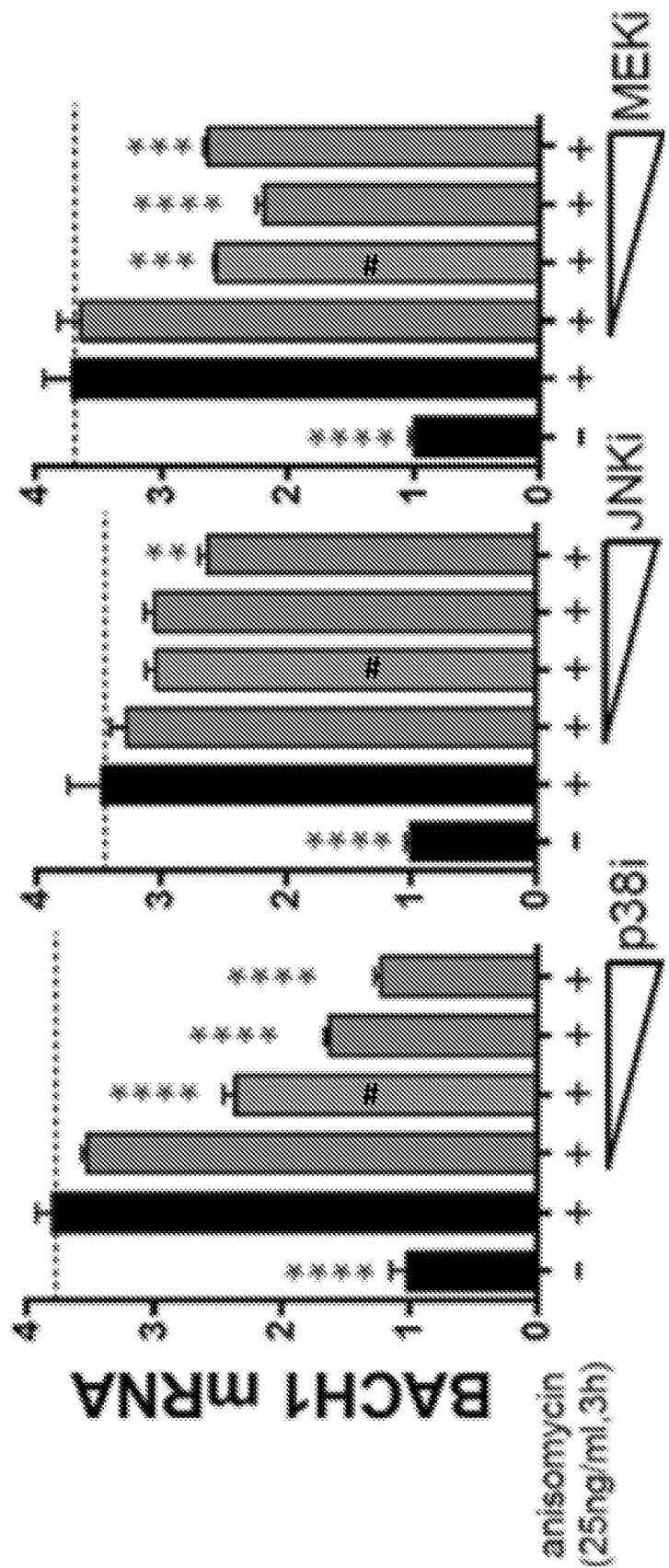
Figure 12E:
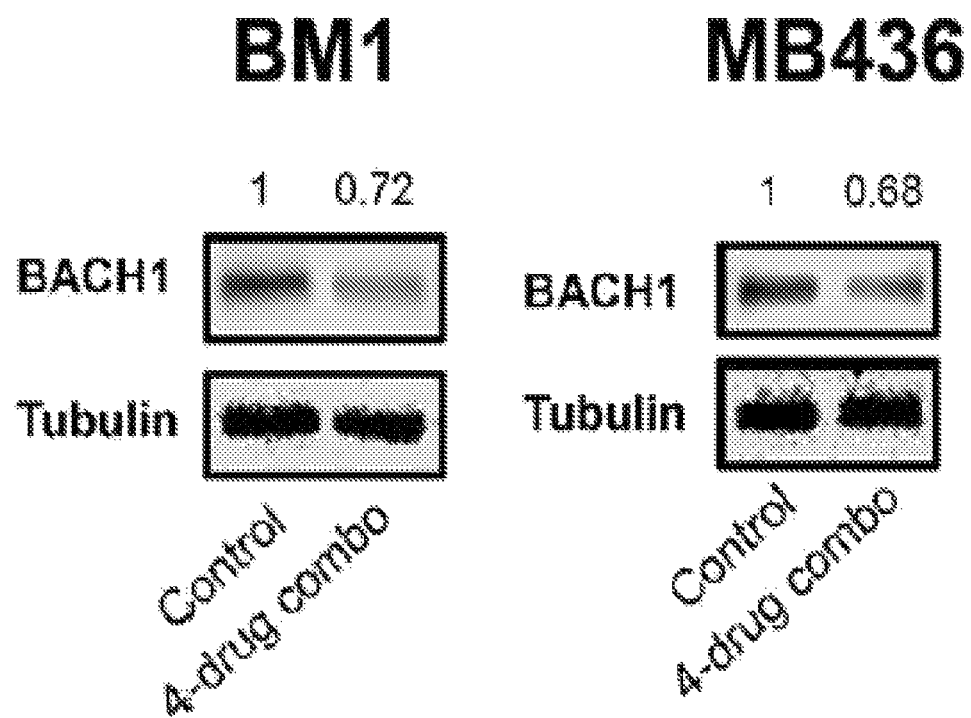
Figure 12F:
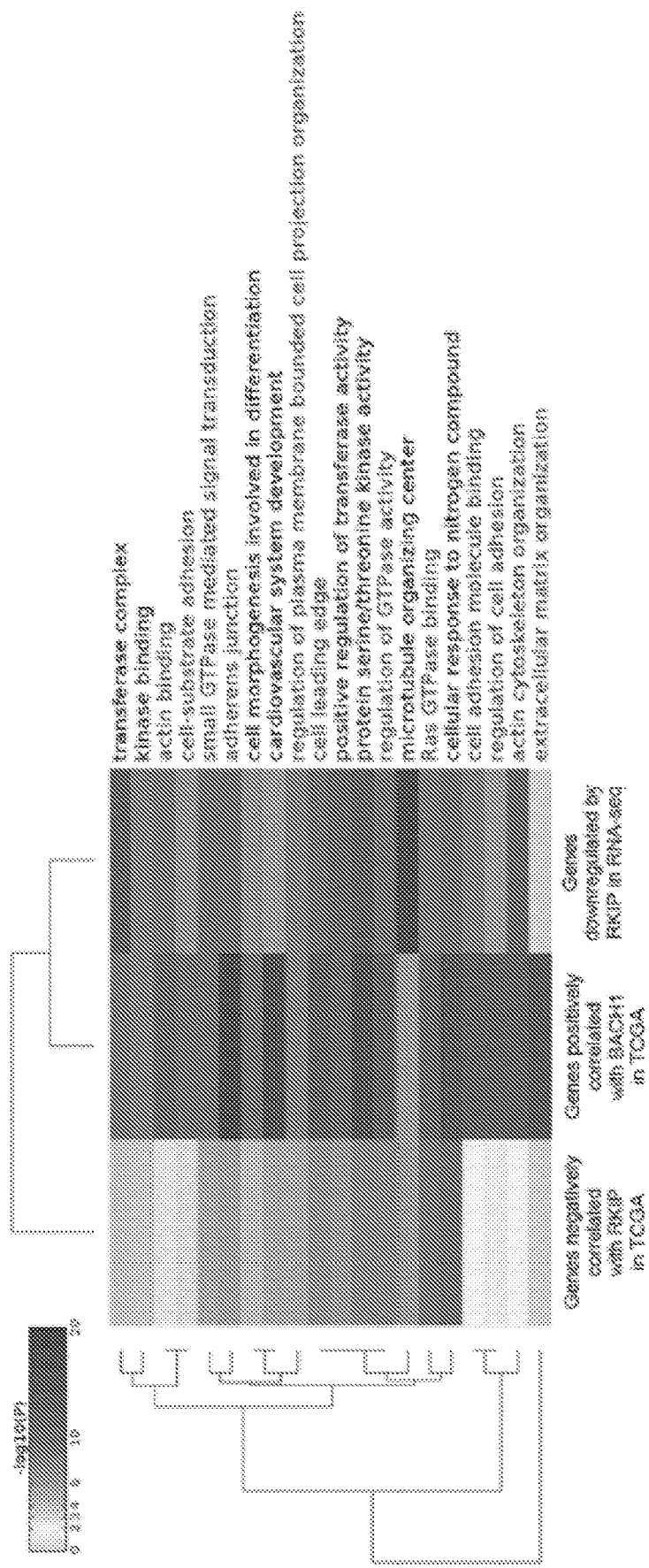
Figure 12G:
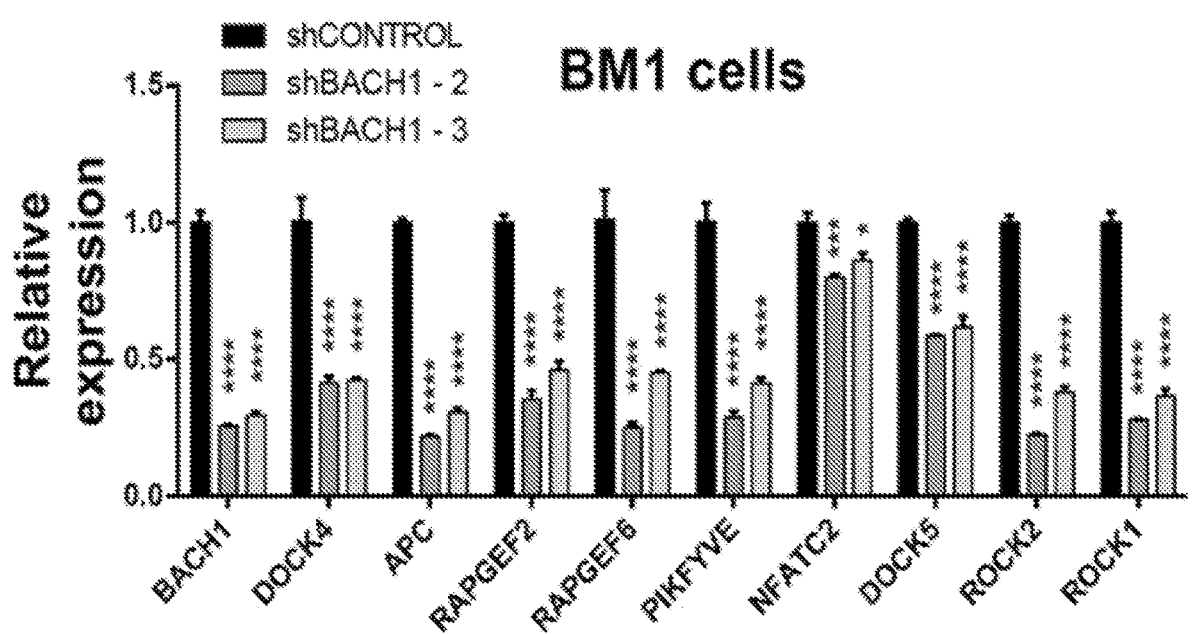
Figure 12H:
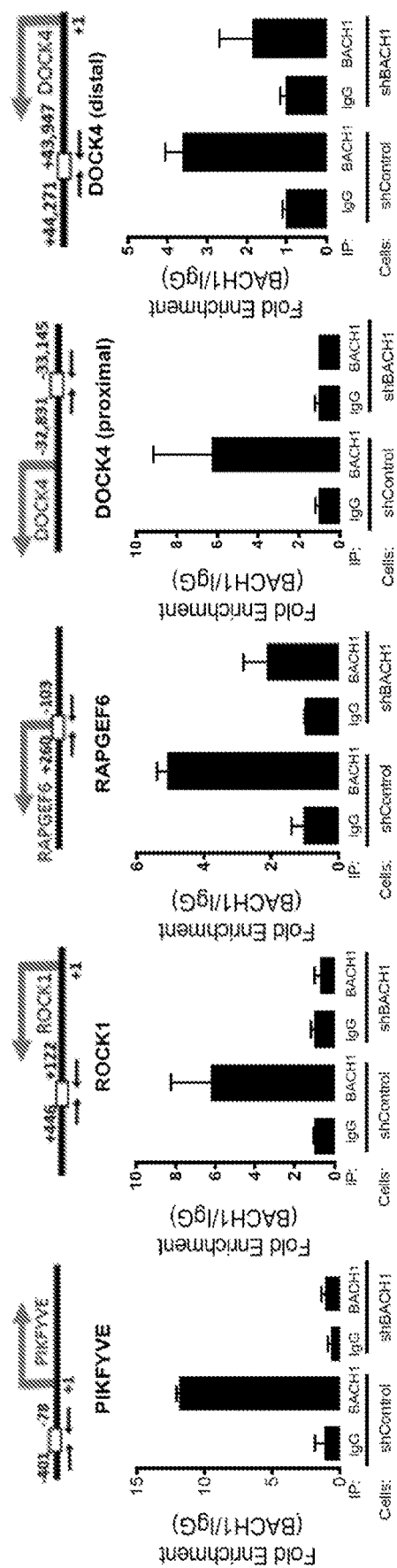
Figure 13A:
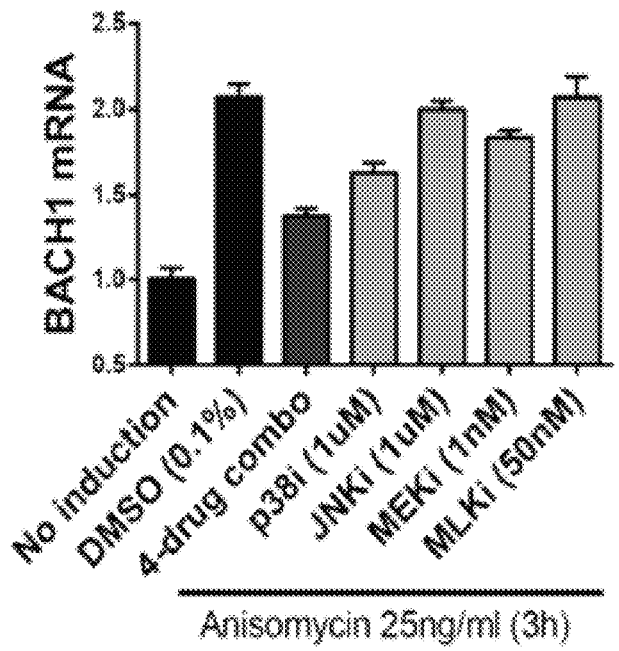
Figure 13B:
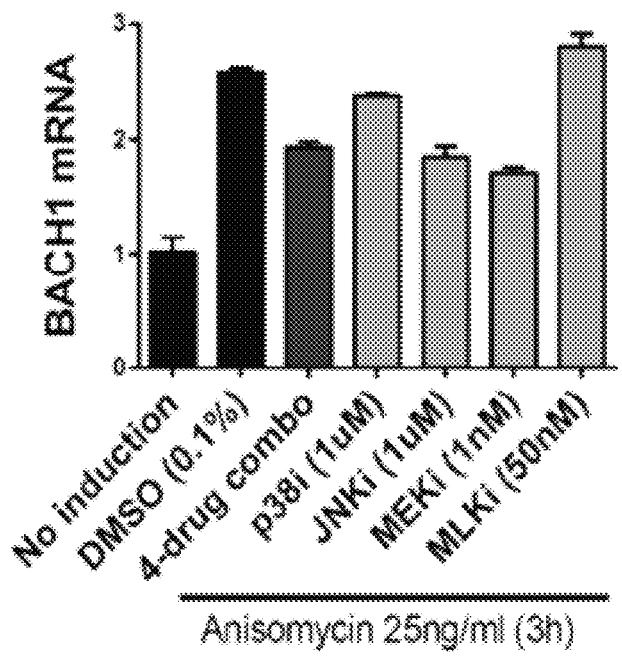
Figure 13C:
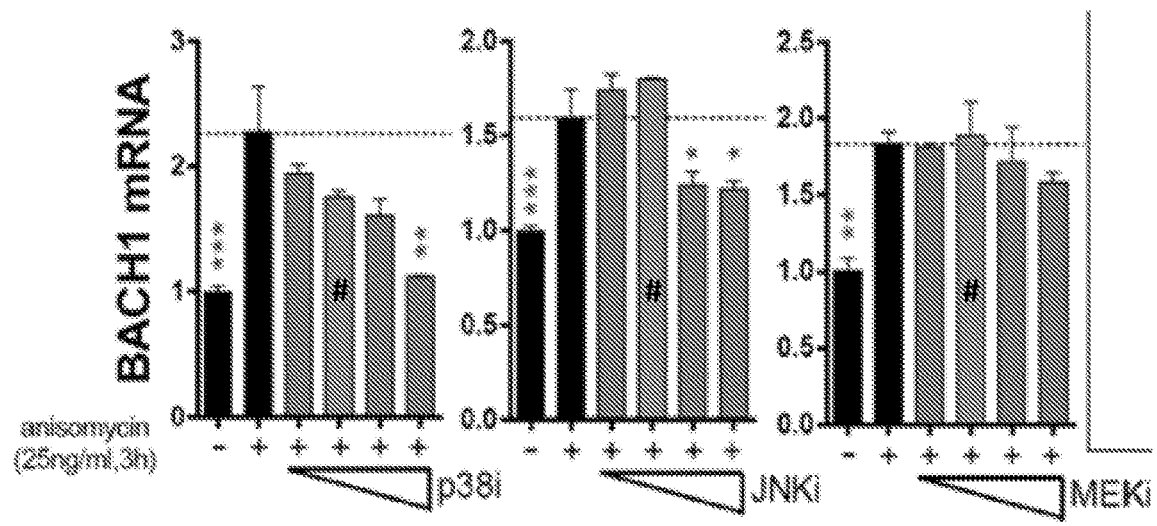
Figure 13D:
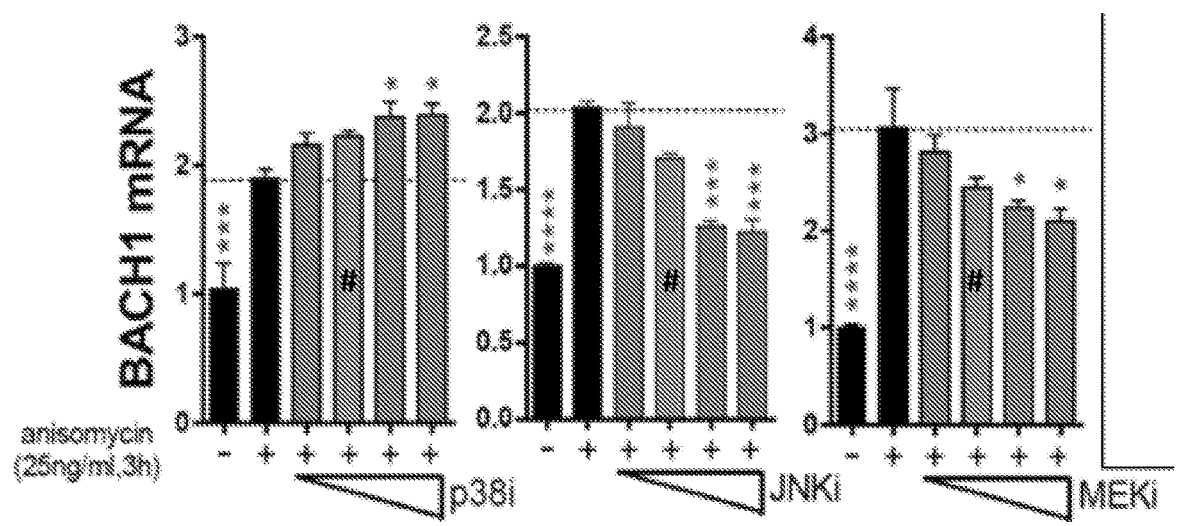
Figure 13F:
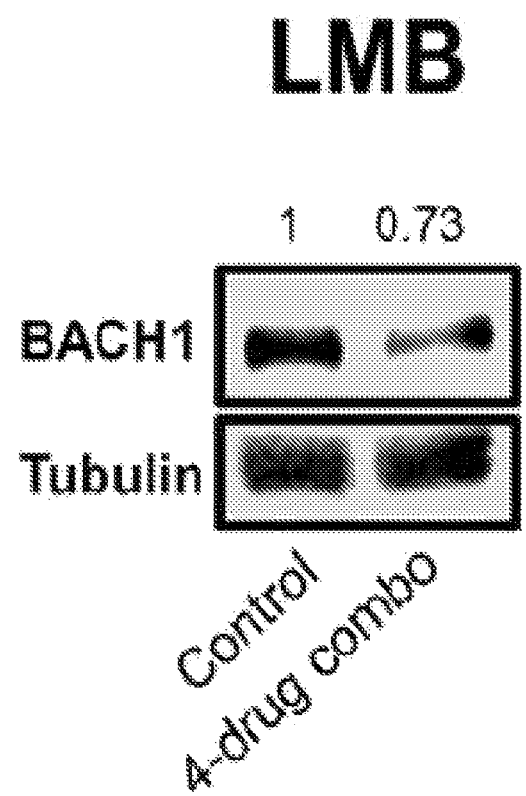
Figure 13G:
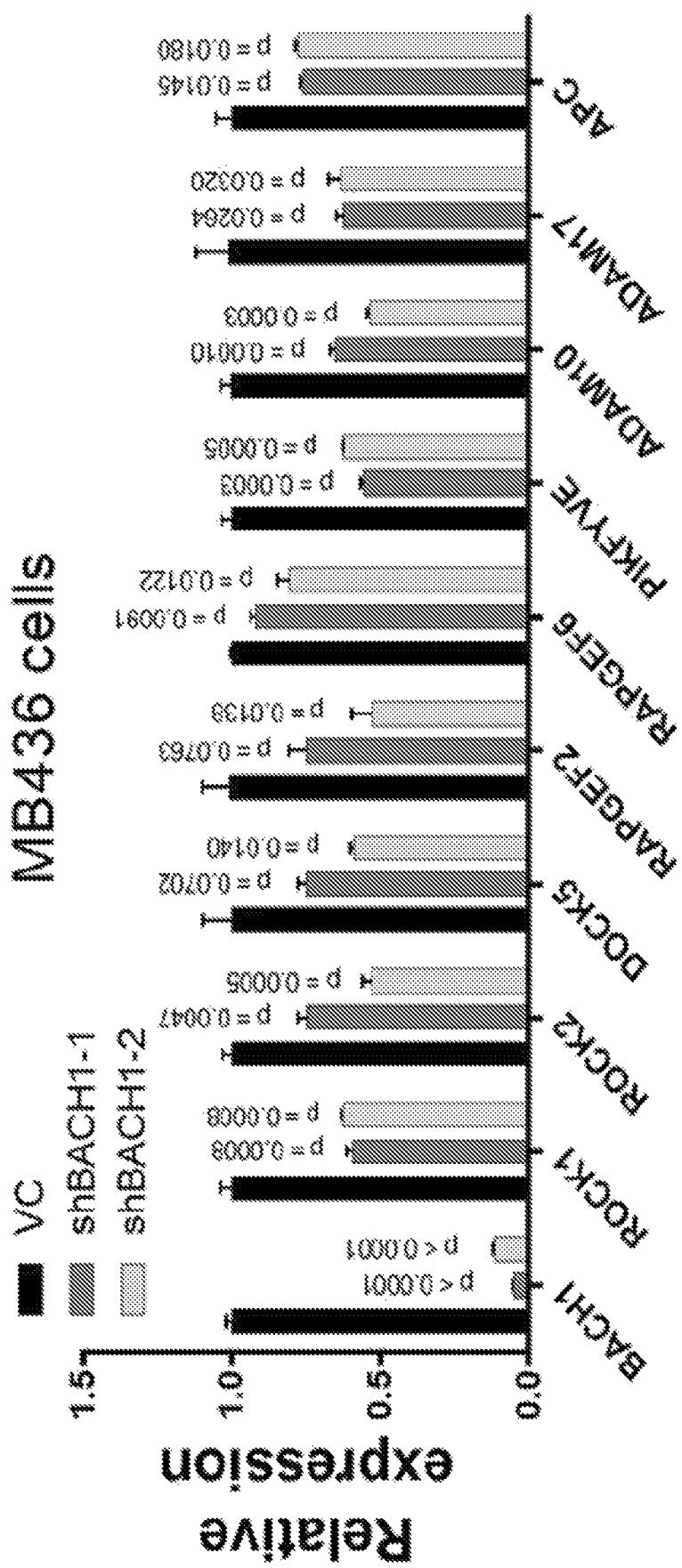

The strong correlation between expression of these metastatic genes raised the possibility that a common transcription factor might be responsible. BACH1 was previously identified as a transcription factor whose protein levels are induced by the Raf-Mek-Erk cascade and negatively regulated by RKIP (Lee et al., 2014; Yun et al., 2011). RNA-seq analysis of xenograft BM1 tumors now shows that RKIP also downregulates BACH1 transcription (FIG. 12A) Similarly, in syngeneic LMB tumors, the RKIP-mimicking 4D-MAPKi significantly reduced BACH1 expression. The regulation of BACH1 transcript by 4D-MAPKi was confirmed in anisomycin-induced human and mouse TNBC cell lines (FIGS. 12C, 13A, and 13B). Dose-response studies with individual MAPK inhibitors showed that BACH1 expression can be regulated by different MAPKs in each cell line (FIGS. 12D, 13C, and 13D, summarized in FIG. 13E). 4D-MAPKi also attenuated BACH1 protein expression in human and mouse cell lines (FIGS. 12E and 13F). These data suggest that both RKIP and 4D-MAPKi regulate transcription of BACH1 as a common downstream mediator of MAPK signaling To identify RKIP target genes that might be transcriptionally regulated by BACH1, genes that are inversely correlated with RKIP (see FIG. 10B) and positively correlated with BACH1 were sought out in the TCGA patient data base. Notably, motility/adhesion genes identified above as RKIP targets were also co-expressed with BACH1 (FIG. 12F). Knocking down BACH1 expression with shRNAs in human TNBC cells resulted in a decrease in the expression levels of the RKIP target genes (FIGS. 12G and 13G), confirming transcriptional regulation of these genes by BACH1. ENCODE data suggested the presence of BACH1 binding sites in the promoter regions of many of these genes (FIG. 11C). CHIP analysis in BM1 cells confirmed that BACH1 specifically binds to the promoters of several genes including ROCK1, DOCK4, PIKFYVE, and RAPGEF6 (FIG. 12H). Together, these findings establish BACH1, a downstream mediator of the MAPK network, as a novel transcriptional regulator of RKIP target genes.

Figure 14A:
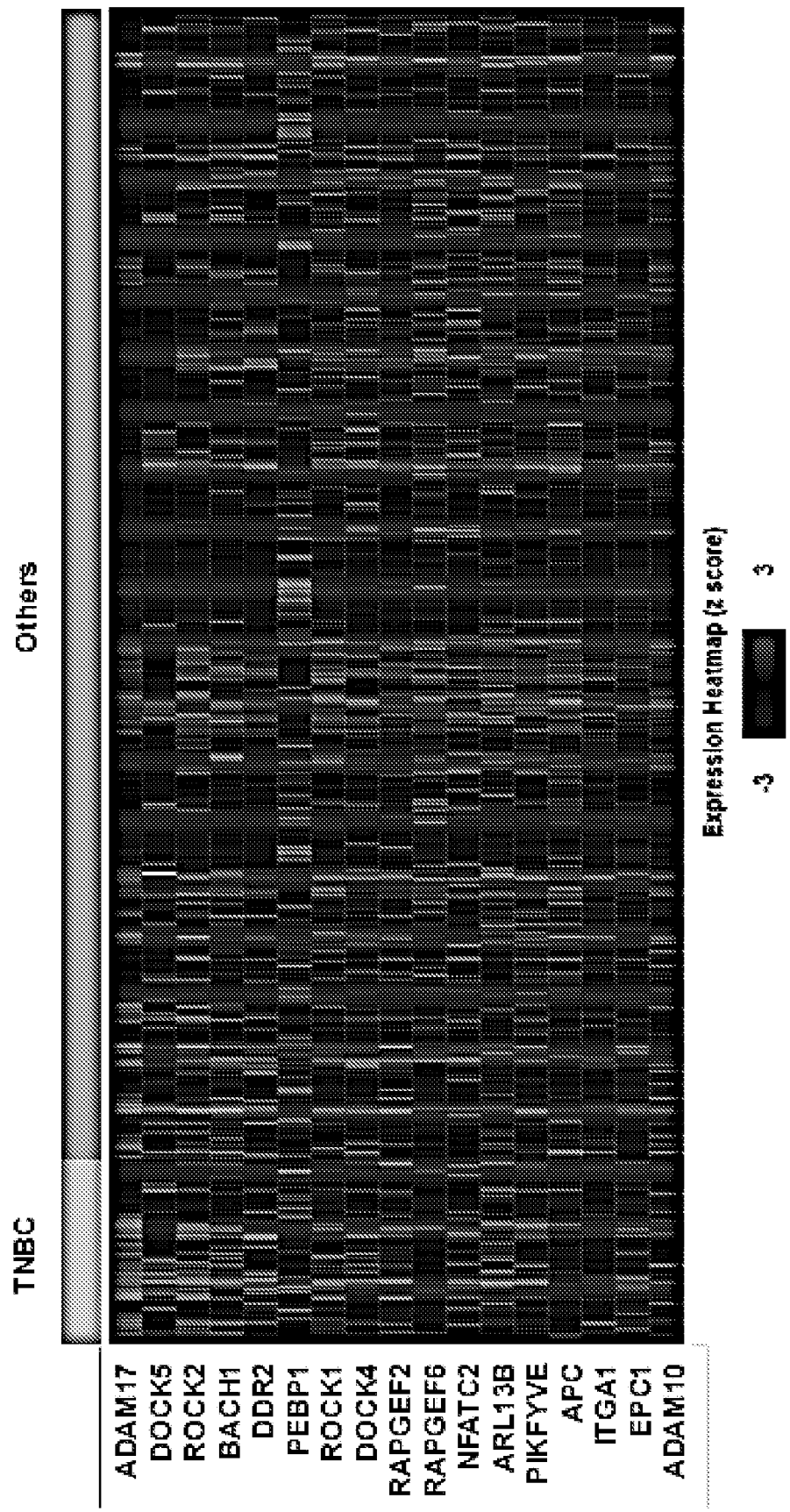
FIGS. 14A-14H: Regulation of the RKIP target genes is a hallmark of metastatic suppression in multiple cancers.
Figure 14B:
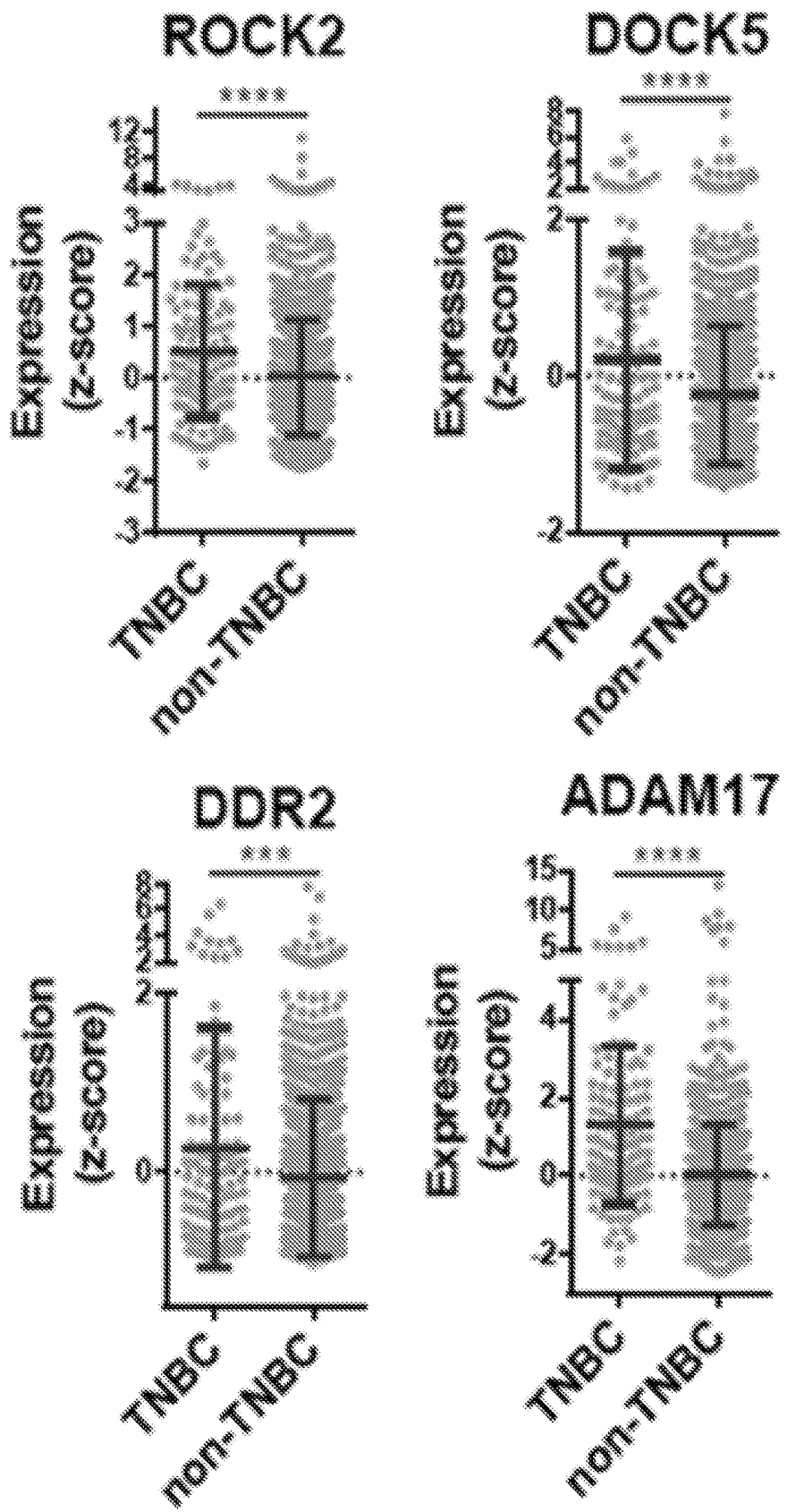
Figure 14C:
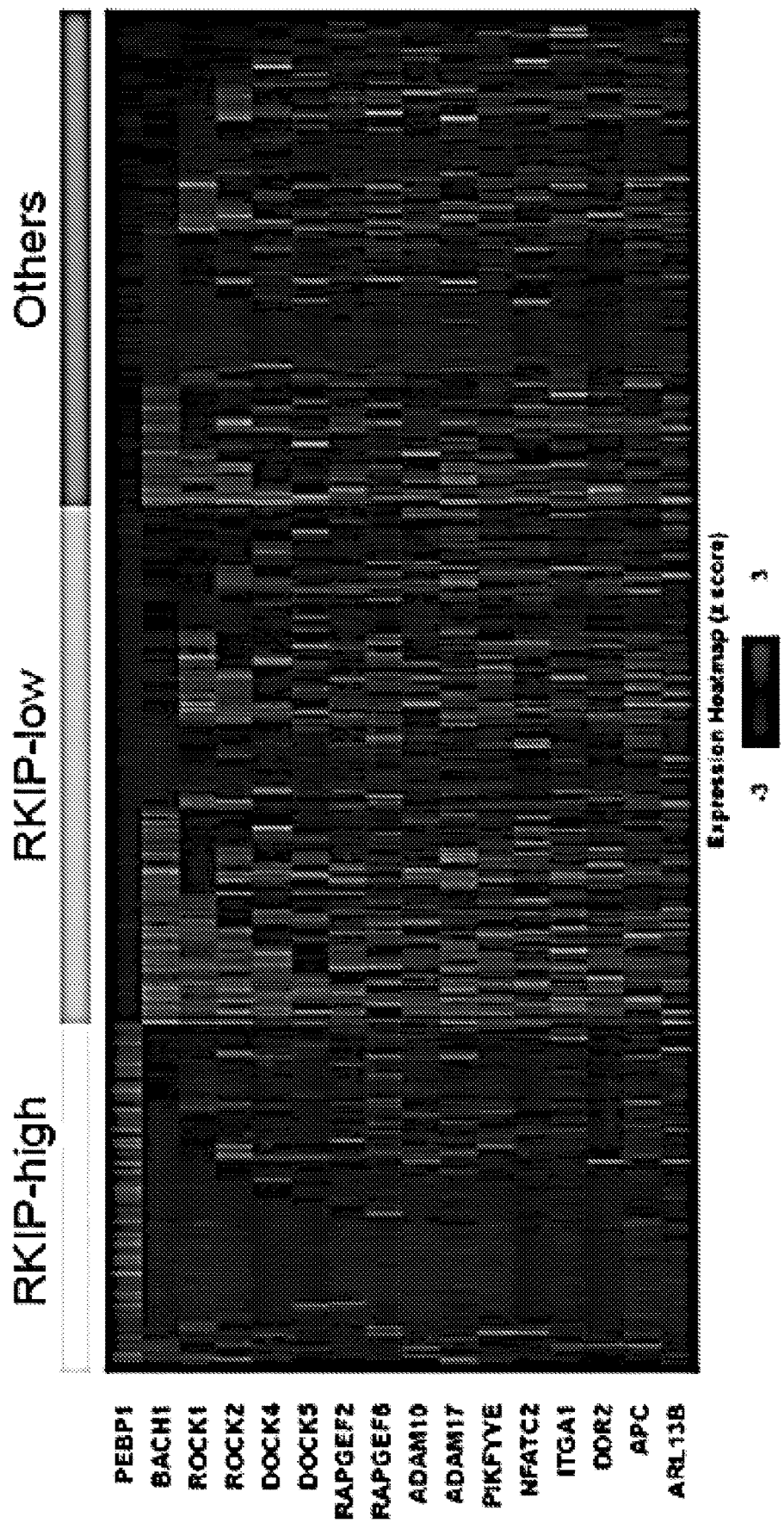

Example 7: Regulation of the RKIP Target Genes is a Hallmark of Metastatic Suppression in Multiple Cancers Previous studies have shown that BACH1 is enriched in TNBC patients (Lee et al., 2019), and the RKIP/BACH1 pathway gene signatures effectively stratify patients for metastatic risk within the TNBC subgroup (Lee et al., 2013). However, unlike BACH1, most of the RKIP target genes identified in this disclosure were not specifically enriched in the TNBC/basal subtype of breast cancer (FIG. 14A), except for ROCK2, DDR2, ADAM17, and DOCK5 (FIG. 14B). Remarkably, stratifying breast cancer patients on the basis of high RKIP and low BACH1 expression reveals a striking inverse association of RKIP with motility/adhesion genes in ~30% of individuals (FIG. 14C). These data suggest that RKIP suppresses this metastatic gene set in breast cancer patients in order to inhibit cell migration and invasion.

Figure 14D:
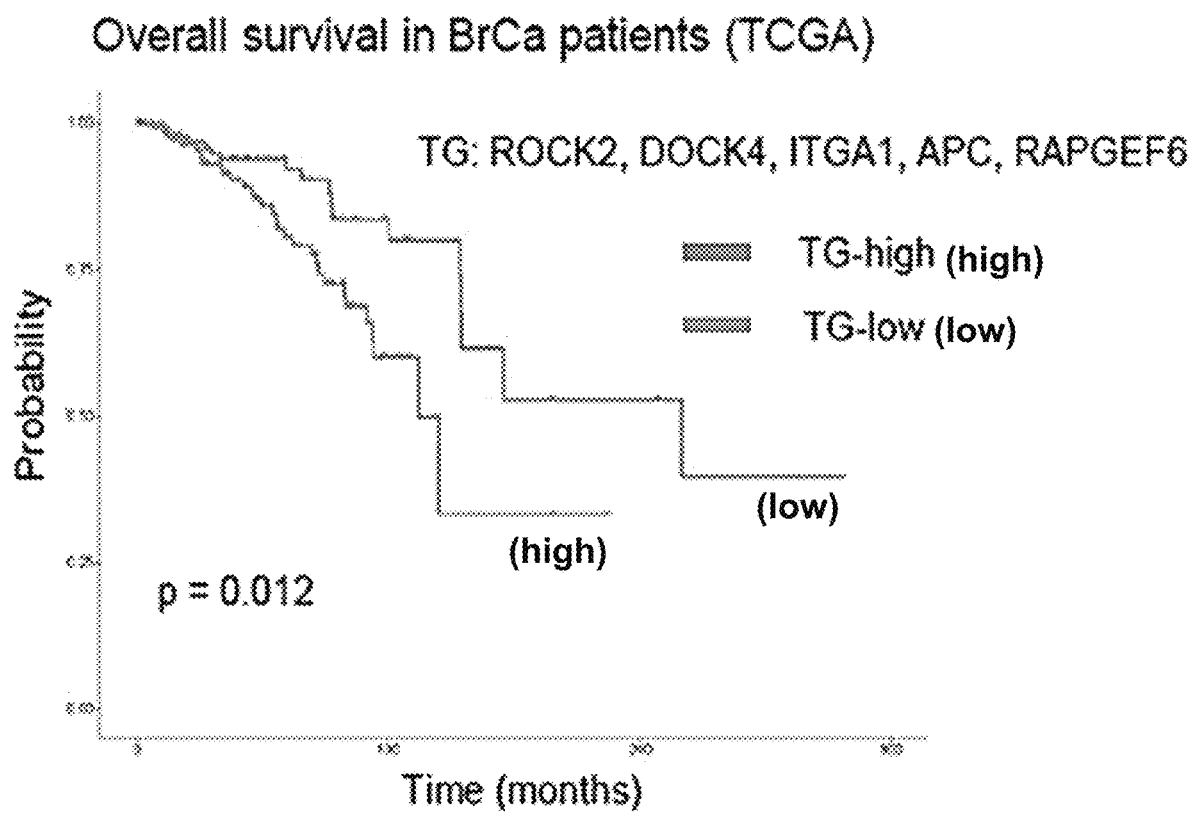

A gene signature consisting of 5 (ROCK2, DOCK4, ITGA1, APC, and RAPGEF6) of the motility/adhesion genes predicts overall survival in TCGA breast cancer patients (FIG. 14D). Kaplan-Meier analysis demonstrates that high expressors (TG-high) have significantly worse prognosis than low expressors (TG-low). This suggests that this 5 gene signature can identify high risk patients who might benefit from treatment with the RKIP-mimicking 4D-MAPKi.

Figure 14E:
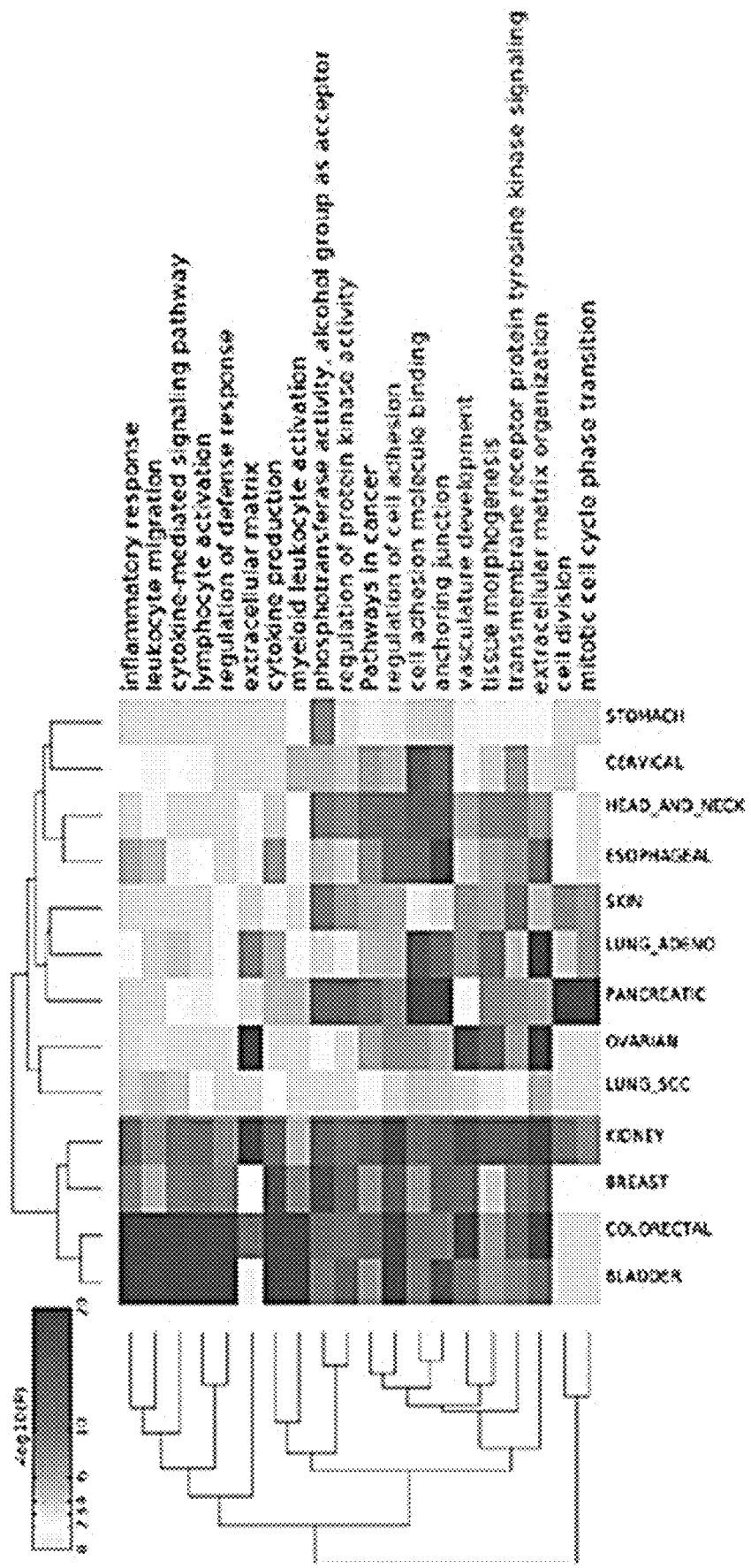
Figure 14F:
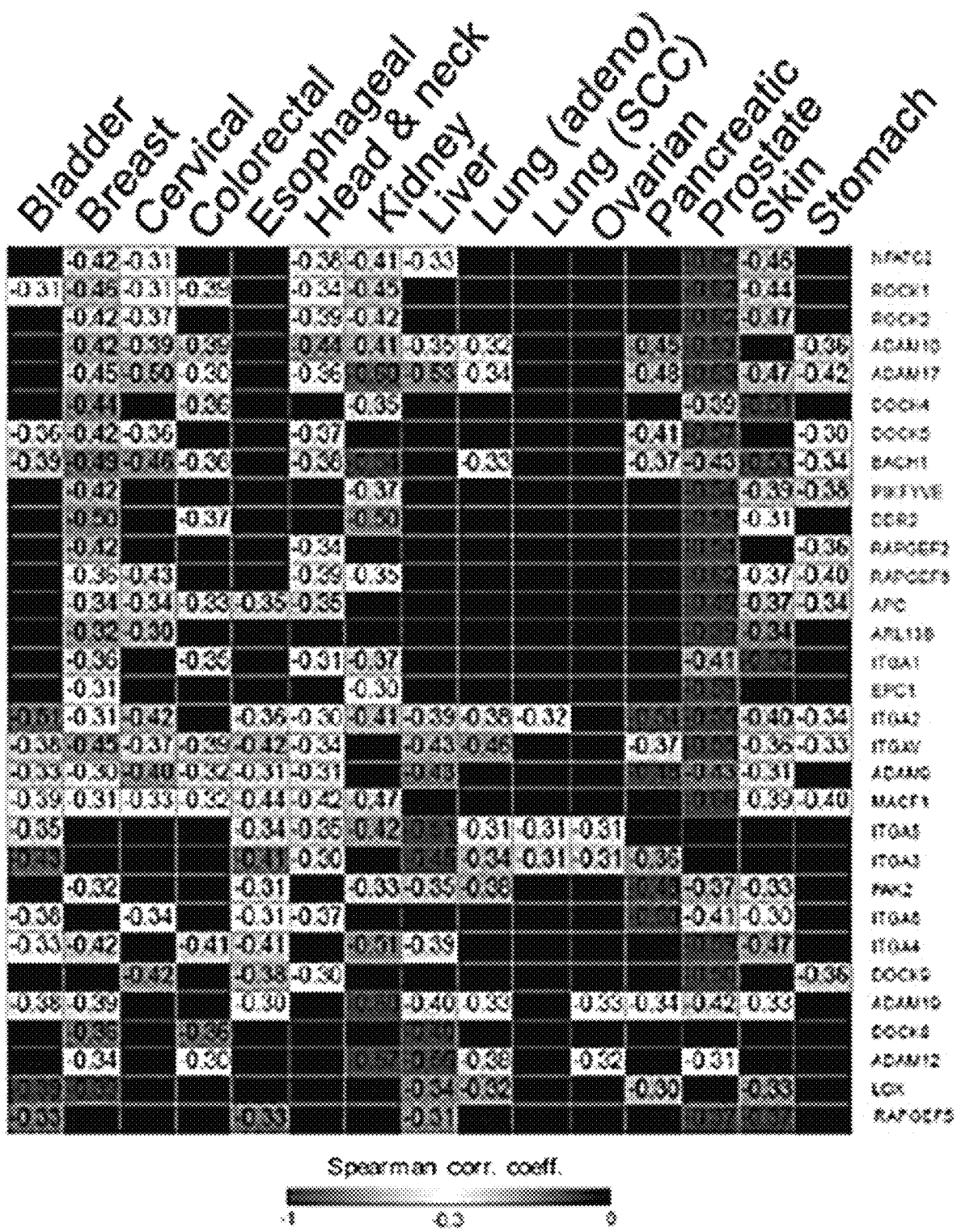
Figure 14G:
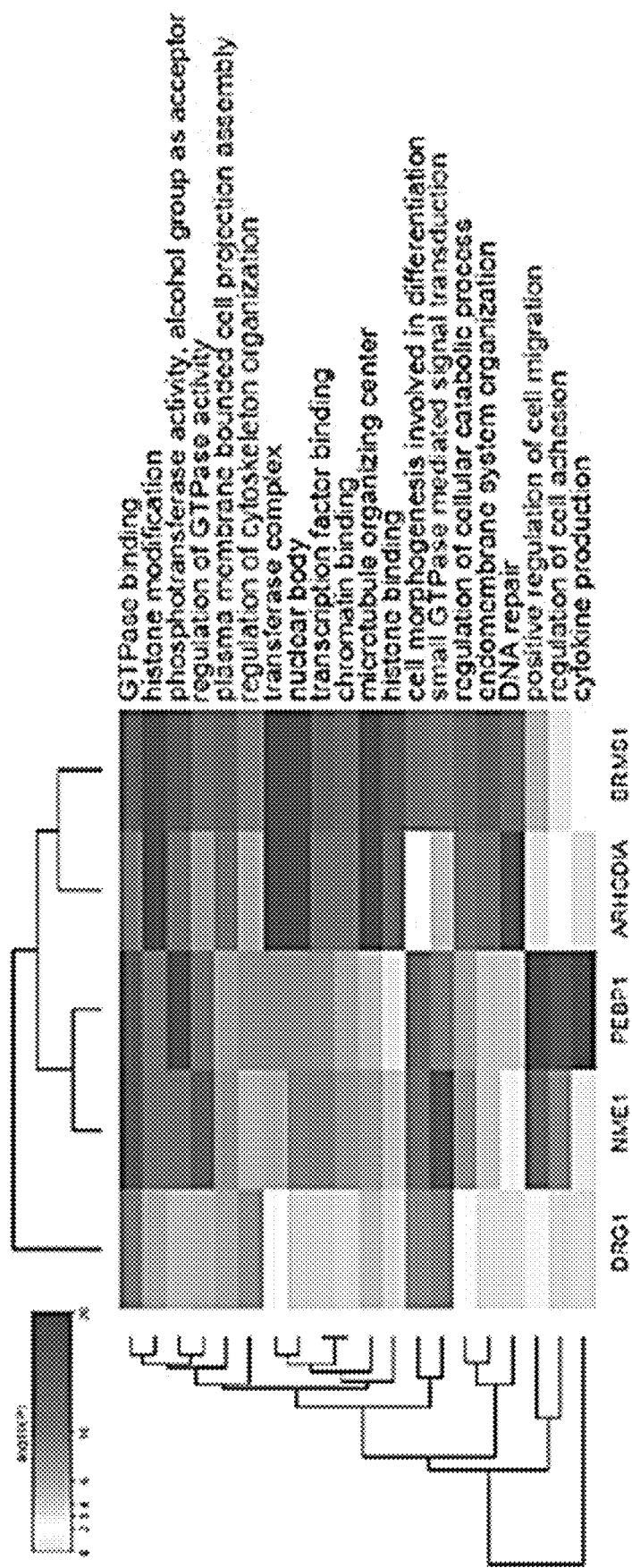
Figure 14H:
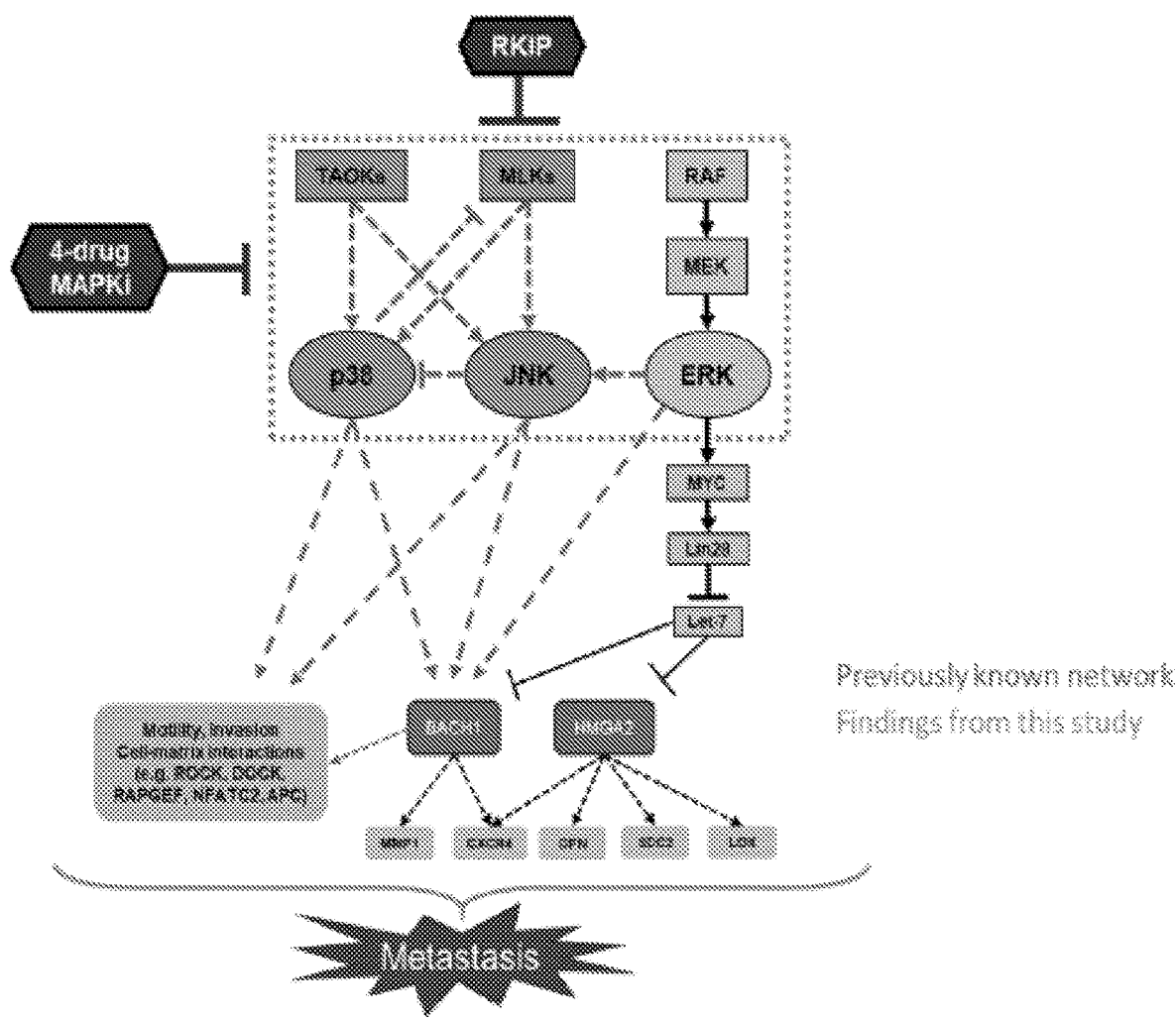
Figure 15A:
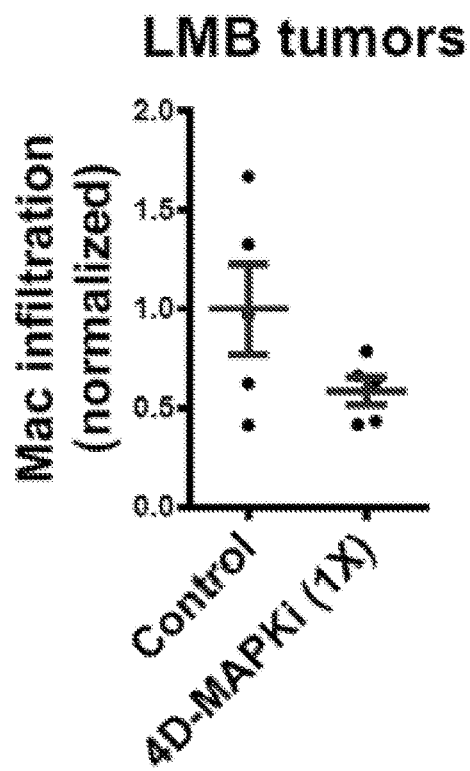
FIGS. 15A-15B: 4D-MAPKi treatment prevents macrophage infiltration.
Figure 15B:
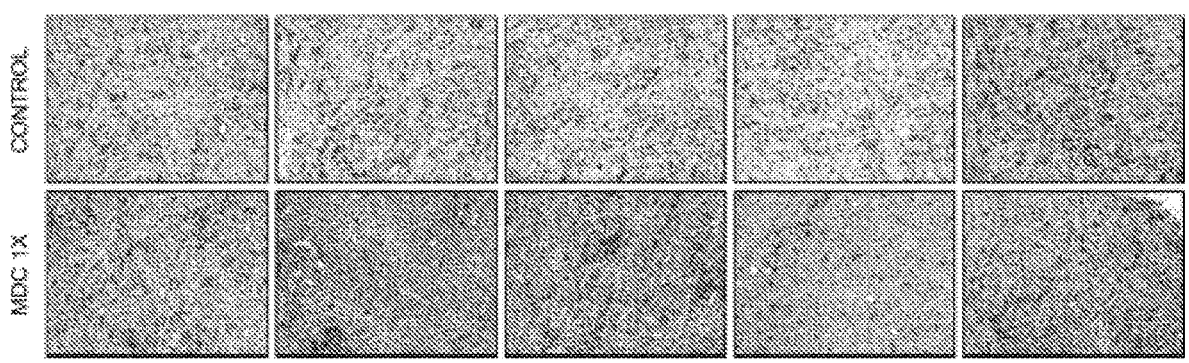

These findings prompted investigation into RKIP's potential association with these metastatic genes in other solid cancer types as well. Combined functional gene set analysis of genes inversely correlated with RKIP across TCGA cancers reveals the same adhesion/motility related gene sets across multiple TCGA cancer types including pancreatic, ovarian, lung, head and neck, and colorectal (FIG. 14E). In particular, genes highlighted here such as BACH1, ROCK1, and DOCK4 are significantly inversely correlated with RKIP in multiple cancer types (FIG. 14F), suggesting that the RKIP-regulated MAPK network is not limited to breast cancer. Of note, in cancers where no correlation to these specific genes was observed, a strong correlation to other members of the same gene families was observed (FIG. 14F). Finally, it was determined that inhibition of this motility gene set is associated with other metastasis suppressors as well as RKIP. Thus, expression of other experimentally validated metastasis suppressors (BRMS1, ARGHDIA, NME1, and DRG1) (Zhao et al., 2015) also negatively correlated with motility and adhesion gene sets (FIG. 14G). Together, these clinical analyses suggest that downregulation of cell-matrix interactions and cytoskeletal machinery is a hallmark of metastasis suppressors, and provides a broad-based therapeutic strategy against metastatic disease.

Discussion

This is the first kinome-level investigation to identify signaling networks targeted by the physiological metastasis suppressor RKIP in vivo. RKIP's inhibitory effect on stress signaling is at least partially mediated through the MAP3K kinases, TAOKs and MLK3. Targeting Raf-Mek-Erk cascade alone is not enough to inhibit stress kinase network in order to mimic RKIP. A combination of 4 kinase inhibitors that target the stress-kinase network blocks TNBC cells' ability to invade without affecting their growth properties in vitro, pheno-copying RKIP. Multi-drug combo (MDC) targeting the stress network abolishes orthotopic and metastatic growth of TNBC in both xenograft and syngeneic mouse models. MDC targets pro-invasive genes whose expression is inversely correlated with RKIP in human patients.

RKIP targets an extensive stress-kinase network but only partially inhibits the kinases to block metastasis. These results suggest that partially impairing kinases in this network in cancer is a viable anti-metastatic strategy. These results suggest that mimicking the metastasis suppressor RKIP by the use of multiple inhibitors that hit multiple targets in the stress kinase network is an effective anti-metastatic strategy.

RKIP's function was investigated at a systems level to unravel signaling events essential for blocking metastasis. RKIP is a specific metastasis suppressor that reprograms kinase networks, interfering with a tumor cell's ability to invade through tissue and enter the circulation for dissemination to secondary sites. This disclosure shows that RKIP, in addition to its known role as an inhibitor of the Raf-MEK-ERK signaling pathway, also targets the stress MAP kinases p38 and JNK in TNBC tumors in part through inhibition of the upstream kinases TAO1-3 and MLK1,3. The results highlight the importance of RKIP as well as the MAPK network as drivers of tumor cell motility leading to metastasis in both preclinical models and human cancer patients and identify a drug cocktail that can mimic RKIP regulation and has the potential to function as both a metastasis suppressor and a tumor suppressor depending on the context.

This disclosure also illustrates the utility of physiological metastasis suppressors in developing effective therapies against metastatic disease. The approach towards elucidating the mechanisms of RKIP not only identified novel signaling networks and target genes regulated by RKIP, but also revealed new treatment modalities that are different than current clinical practices. Namely, to mimic RKIP, the efficacy of combination therapies that are comprised of more than 2 small molecule inhibitors, each used at sub-therapeutic doses was investigated. The findings demonstrate that, by targeting the MAPK network and partially inhibiting three MAPK nodes (ERK, p38, and JNK), the metastatic phenotype can be reverted without causing toxicity in vitro or in vivo.

This research supports the idea that stress signaling is important for metastatic progression of cancers. In the TNBC model systems, RKIP does not regulate EMT markers, nor it correlates with EMT genes in the TCGA breast cancer patient data (Yesilkanal and Rosner, 2018), yet it blocks metastatic progression by inhibiting stress kinase signaling. This suggests that stress kinase signaling is important in later stages of metastasis as well, and a good therapeutic target for metastasis.

The results also significantly expand the knowledge of how RKIP functions as a metastasis suppressor. Using the MIB-MS method, this disclosure not only validated regulation of known RKIP targets such as ERK in tumors, but also identified other kinases that are regulated by RKIP independently of Raf signaling. In particular, stress MAPKs JNK, MLKs, and TAOKs have never been implicated as a part of the RKIP-network before. To our best knowledge, there is only one report that implicates p38 as an indirect RKIP target (Al-Mulla et al., 2011). This disclosure shows that when RKIP is depleted, p38 kinase becomes activated indirectly due to increased reactive oxygen species (ROS) in tumor cells. This work has identified an alternative route to p38 inhibition by RKIP which involves the upstream MAP3Ks TAOKs and MLKs. Whether RKIP directly binds to these MAP3Ks, or it has other binding partners that indirectly regulate the stress MAPK network remains to be explored.

The multi-drug combination disclosed herein targeting MEK, p38, JNK, and MLK is a novel combination. In the clinic, resistance to MEK inhibitors are associated with activation of PI3K and AKT pathways (Chen et al., 2017; McNeill et al., 2017), and therefore, most combination attempts have focused PI3K or AKT inhibitors along with MEK inhibitors (McNeill et al., 2017; Meng et al., 2010). Other approaches involve combining receptor tyrosine kinase inhibitors, HDAC inhibitors, and inhibitors of tumor-associated microenvironment (reviewed by (Smith and Wellbrock, 2016). p38 and JNK inhibitors as single agents yielded discouraging results in clinical trials (Messoussi et al., 2014). Some studies now focus on combining p38 inhibitors with chemotherapeutic agents such as gemcitibine and carboplatin (Cicenas et al., 2017) (e.g. clinical trial NCT01663857) or with EGFR/HER2 inhibitors (Mora Vidal et al., 2018). To date, very few JNK inhibitors made it to the clinical trial level. An early MLK inhibitor CEP-1347 was tested in Phase II-III clinical trials for Parkinson's disease and did not show efficacy, but now it is being considered as anti-cancer treatment for targeting stem cells (Okada et al., 2017). A more recent MLK inhibitor URMC-099 is still in its pre-clinical phases. The approach of targeting these four MAPKs is unique because, and to the inventor's knowledge, no other disclosure is considering such combination. This approach is not limited to the use of the four specific inhibitors used in this disclosure (SB203580, SP600125, Trametinib, and URMC-099). There can be other possible combinations of various number of inhibitors that target the RKIP-network. These findings would also justify development of multi-target kinase inhibitors that inhibit all three MAPKs p38, JNK, and MEK/ERK.

This disclosure illustrates the utility of physiological metastasis suppressors in developing effective therapies against metastatic disease. This approach towards elucidating the mechanisms of RKIP not only identified novel signaling networks and target genes regulated by RKIP, but also revealed new treatment modalities that are different than current clinical practices. Namely, to mimic RKIP, the efficacy of combination therapies that are comprised of two or more small molecule inhibitors were investigated, each used at sub-therapeutic doses. These findings demonstrate that, by targeting the MAPK network and partially inhibiting all three MAPK nodes (ERK, p38, and JNK), the metastatic phenotype can be reverted without causing toxicity in vitro or in vivo. This analysis of the RKIP-regulated kinome suggests that an effective strategy to suppress metastasis would be to use combinations of low dose inhibitors in order to target multiple nodes within a kinase network.

Having described the invention in detail and by reference to specific aspects and/or embodiments thereof, it will be apparent that modifications and variations are possible without departing from the scope of the invention defined in the appended claims. More specifically, although some aspects of the present invention may be identified herein as particularly advantageous, it is contemplated that the present invention is not limited to these particular aspects of the invention.

REFERENCES

Al-Mahmood, S., Sapiezynski, J., Garbuzenko, O. B., and Minko, T. (2018). Metastatic and triple-negative breast cancer: challenges and treatment options. Drug Deliv. Transl. Res. 8, 1483-1507. Al-Mulla, F., Bitar, M. S., Al-Maghrebi, M., Behbehani, A. I., Al-Ali, W., Rath, O., Doyle, B., Tan, K. Y., Pitt, A., and Kolch, W. (2011). Raf kinase inhibitor protein RKIP enhances signaling by glycogen synthase kinase-3β. Cancer Res. 71, 1334-1343.

Amano, M., Nakayama, M., and Kaibuchi, K. (2010). Rho-kinase/ROCK: A key regulator of the cytoskeleton and cell polarity. Cytoskelet. Hoboken NJ 67, 545-554.

Bainer, R., Frankenberger, C., Rabe, D., An, G., Gilad, Y., and Rosner, M. R. (2016). Gene expression in local stroma reflects breast tumor states and predicts patient outcome. Sci. Rep. 6, 39240.

Bonavida, B., Baritaki, S., Huerta-Yepez, S., Vega, M. I., Chatterjee, D., and Yeung, K. (2008). Novel therapeutic applications of nitric oxide donors in cancer: roles in chemo- and immunosensitization to apoptosis and inhibition of metastases. Nitric Oxide Biol. Chem. 19, 152-157.

Chatterjee, D., Bai, Y., Wang, Z., Beach, S., Mott, S., Roy, R., Braastad, C., Sun, Y., Mukhopadhyay, A., Aggarwal, B. B., et al. (2004). RKIP sensitizes prostate and breast cancer cells to drug-induced apoptosis. J. Biol. Chem. 279, 17515-17523.

Chen, C.-H., Hsia, T.-C., Yeh, M.-H., Chen, T.-W., Chen, Y.-J., Chen, J.-T., Wei, Y.-L., Tu, C.-Y., and Huang, W.-C. (2017). MEK inhibitors induce Akt activation and drug resistance by suppressing negative feedback ERK-mediated HER2 phosphorylation at Thr701. Mol. Oncol. 11, 1273-1287. Chen, Z., Hutchison, M., and Cobb, M. H. (1999). Isolation of the protein kinase TAO2 and identification of its mitogen-activated protein kinase/extracellular signal-regulated kinase kinase binding domain. J. Biol. Chem. 274, 28803-28807.

Choi, Y., Ko, Y. S., Park, J., Choi, Y., Kim, Y., Pyo, J.-S., Jang, B. G., Hwang, D. H., Kim, W. H., and Lee, B. L. (2016). HER2-induced metastasis is mediated by AKT/JNK/EMT signaling pathway in gastric cancer. World J. Gastroenterol. 22, 9141-9153.

Cicenas, J., Zalyte, E., Rimkus, A., Dapkus, D., Noreika, R., and Urbonavicius, S. (2017). JNK, p38, ERK, and SGK1 Inhibitors in Cancer. Cancers 10.

Dangi-Garimella, S., Yun, J., Eves, E. M., Newman, M., Erkeland, S. J., Hammond, S. M., Minn, A. J., and Rosner, M. R. (2009). Raf kinase inhibitory protein suppresses a metastasis signalling cascade involving LIN28 and let-7. EMBO J. 28, 347-358.

Dhillon, A. S., Hagan, S., Rath, O., and Kolch, W. (2007). MAP kinase signalling pathways in cancer. Oncogene 26, 3279-3290.

Duncan, J. S., Whittle, M. C., Nakamura, K., Abell, A. N., Midland, A. A., Zawistowski, J. S., Johnson, N. L., Granger, D. A., Jordan, N. V., Darr, D. B., et al. (2012). Dynamic reprogramming of the kinome in response to targeted MEK inhibition in triple-negative breast cancer. Cell 149, 307-321.

ENCODE Project Consortium (2012). An integrated encyclopedia of DNA elements in the human genome. Nature 489, 57-74.

Flockhart, R. J., Armstrong, J. L., Reynolds, N. J., and Lovat, P. E. (2009). NFAT signalling is a novel target of oncogenic BRAF in metastatic melanoma. Br. J. Cancer 101, 1448-1455.

Frankenberger, C., Rabe, D., Bainer, R., Sankarasharma, D., Chada, K., Krausz, T., Gilad, Y., Becker, L., and Rosner, M. R. (2015). Metastasis Suppressors Regulate the Tumor Microenvironment by Blocking Recruitment of Prometastatic Tumor-Associated Macrophages. Cancer Res. 75, 4063-4073. Gadea, G., and Blangy, A. (2014). Dock-family exchange factors in cell migration and disease. Eur. J. Cell Biol. 93, 466-477.

Gallo, K. A., and Johnson, G. L. (2002). Mixed-lineage kinase control of JNK and p38 MAPK pathways. Nat. Rev. Mol. Cell Biol. 3, 663-672.

Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Sci. Signal. 6, p11.

Harper, K. L., Sosa, M. S., Entenberg, D., Hosseini, H., Cheung, J. F., Nobre, R., Avivar-Valderas, A., Nagi, C., Girnius, N., Davis, R. J., et al. (2016). Mechanism of early dissemination and metastasis in Her2+ mammary cancer. Nature.

Hipp, S., Berg, D., Ergin, B., Schuster, T., Hapfelmeier, A., Walch, A., Avril, S., Schmalfeldt, B., Höfler, H., and Becker, K.-F. (2010). Interaction of Snail and p38 mitogen-activated protein kinase results in shorter overall survival of ovarian cancer patients. Virchows Arch. Int. J. Pathol. 457, 705-713.

Holzer, R. G., MacDougall, C., Cortright, G., Atwood, K., Green, J. E., and Jorcyk, C. L. (2003). Development and characterization of a progressive series of mammary adenocarcinoma cell lines derived from the C3(1)/SV40 Large T-antigen transgenic mouse model. Breast Cancer Res. Treat. 77, 65-76.

Hong, J., Zhou, J., Fu, J., He, T., Qin, J., Wang, L., Liao, L., and Xu, J. (2011). Phosphorylation of serine 68 of Twist1 by MAPKs stabilizes Twist1 protein and promotes breast cancer cell invasiveness. Cancer Res. 71, 3980-3990.

Isaeva, A. R., and Mitev, V. I. (2011). CK2 is acting upstream of MEK3/6 as a part of the signal control of ERK1/2 and p38 MAPK during keratinocytes autocrine differentiation. Z. Naturforschung C J. Biosci. 66, 83-86.

Johnstone, C. N., Smith, Y. E., Cao, Y., Burrows, A. D., Cross, R. S. N., Ling, X., Redvers, R. P., Doherty, J. P., Eckhardt, B. L., Natoli, A. L., et al. (2015). Functional and molecular characterisation of E0771.LMB tumours, a new C57BL/6-mouse-derived model of spontaneously metastatic mammary cancer. Dis. Model. Mech. 8, 237-251.

Kang, Y., Siegel, P. M., Shu, W., Drobnjak, M., Kakonen, S. M., Cordón-Cardo, C., Guise, T. A., and Massagué, J. (2003). A multigenic program mediating breast cancer metastasis to bone. Cancer Cell 3, 537-549.

Karoulia, Z., Gavathiotis, E., and Poulikakos, P. I. (2017). New perspectives for targeting RAF kinase in human cancer. Nat. Rev. Cancer 17, 676-691.

Kobayashi, M., Harada, K., Negishi, M., and Katoh, H. (2014). Dock4 forms a complex with SH3YL1 and regulates cancer cell migration. Cell. Signal. 26, 1082-1088.

Lamiman, K., Keller, J. M., Mizokami, A., Zhang, J., and Keller, E. T. (2014). Survey of Raf kinase inhibitor protein (RKIP) in multiple cancer types. Crit. Rev. Oncog. 19, 455-468.

Lawrence, M. C., Borenstein-Auerbach, N., McGlynn, K., Kunnathodi, F., Shahbazov, R., Syed, I., Kanak, M., Takita, M., Levy, M. F., and Naziruddin, B. (2015). NFAT targets signaling molecules to gene promoters in pancreatic β-cells. Mol. Endocrinol. Baltim. Md. 29, 274-288.

Lee, J., Lee, J., Farquhar, K. S., Yun, J., Frankenberger, C. A., Bevilacqua, E., Yeung, K., Kim, E.-J., Balázsi, G., and Rosner, M. R. (2014). Network of mutually repressive metastasis regulators can promote cell heterogeneity and metastatic transitions. Proc. Natl. Acad. Sci. U.S.A. 111, E364-373.

Lee, J., Yesilkanal, A. E., Wynne, J. P., Frankenberger, C., Liu, J., Yan, J., Elbaz, M., Rabe, D. C., Rustandy, F. D., Tiwari, P., et al. (2019). Effective breast cancer combination therapy targeting BACH1 and mitochondrial metabolism. Nature.

Lee, U., Frankenberger, C., Yun, J., Bevilacqua, E., Caldas, C., Chin, S.-F., Rueda, O. M., Reinitz, J., and Rosner, M. R. (2013). A prognostic gene signature for metastasis-free survival of triple negative breast cancer patients. PloS One 8, e82125.

McNeill, R. S., Canoutas, D. A., Stuhlmiller, T. J., Dhruv, H. D., Irvin, D. M., Bash, R. E., Angus, S. P., Herring, L. E., Simon, J. M., Skinner, K. R., et al. (2017). Combination therapy with potent PI3K and MAPK inhibitors overcomes adaptive kinome resistance to single agents in preclinical models of glioblastoma. Neuro-Oncol. 19, 1469-1480.

Meng, J., Dai, B., Fang, B., Bekele, B. N., Bornmann, W. G., Sun, D., Peng, Z., Herbst, R. S., Papadimitrakopoulou, V., Minna, J. D., et al. (2010). Combination treatment with MEK and AKT inhibitors is more effective than each drug alone in human non-small cell lung cancer in vitro and in vivo. PloS One 5, e14124.

Messoussi, A., Feneyrolles, C., Bros, A., Deroide, A., Daydé-Cazals, B., Chevé, G., Van Hijfte, N., Fauvel, B., Bougrin, K., and Yasri, A. (2014). Recent progress in the design, study, and development of c-Jun N-terminal kinase inhibitors as anticancer agents. Chem. Biol. 21, 1433-1443.

Mora Vidal, R., Regufe da Mota, S., Hayden, A., Markham, H., Douglas, J., Packham, G., and Crabb, S. J. (2018). Epidermal Growth Factor Receptor Family Inhibition Identifies P38 Mitogen-activated Protein Kinase as a Potential Therapeutic Target in Bladder Cancer. Urology 112, 225.e1-225.e7.

Odabaei, G., Chatterjee, D., Jazirehi, A. R., Goodglick, L., Yeung, K., and Bonavida, B. (2004). Raf-1 kinase inhibitor protein: structure, function, regulation of cell signaling, and pivotal role in apoptosis. Adv. Cancer Res. 91, 169-200.

Okada, M., Takeda, H., Sakaki, H., Kuramoto, K., Suzuki, S., Sanomachi, T., Togashi, K., Seino, S., and Kitanaka, C. (2017). Repositioning CEP-1347, a chemical agent originally developed for the treatment of Parkinson's disease, as an anti-cancer stem cell drug. Oncotarget 8, 94872-94882.

Ortega-Pérez, I., Cano, E., Were, F., Villar, M., Vázquez, J., and Redondo, J. M. (2005). c-Jun N-terminal kinase (JNK) positively regulates NFATc2 transactivation through phosphorylation within the N-terminal regulatory domain. J. Biol. Chem. 280, 20867-20878.

Piala, A. T., Akella, R., Potts, M. B., Dudics-Giagnocavo, S. A., He, H., Wei, S., White, M. A., Posner, B. A., and Goldsmith, E. J. (2016). Discovery of novel TAOK2 inhibitor scaffolds from high-throughput screening. Bioorg. Med. Chem. Lett. 26, 3923-3927.

Qin, J.-J., Nag, S., Wang, W., Zhou, J., Zhang, W.-D., Wang, H., and Zhang, R. (2014). NFAT as cancer target: mission possible? Biochim. Biophys. Acta 1846, 297-311.

Rattanasinchai, C., and Gallo, K. A. (2016). MLK3 Signaling in Cancer Invasion. Cancers 8.

Riento, K., and Ridley, A. J. (2003). Rocks: multifunctional kinases in cell behaviour. Nat. Rev. Mol. Cell Biol. 4, 446-456.

Sayed, M., Kim, S. O., Salh, B. S., Issinger, O.-G., and Pelech, S. L. (2000). Stress-induced Activation of Protein Kinase CK2 by Direct Interaction with p38 Mitogen-activated Protein Kinase. J. Biol. Chem. 275, 16569-16573.

Skinner, J. J., Wang, S., Lee, J., Ong, C., Sommese, R., Sivaramakrishnan, S., Koelmel, W., Hirschbeck, M., Schindelin, H., Kisker, C., et al. (2017). Conserved salt-bridge competition triggered by phosphorylation regulates the protein interactome. Proc. Natl. Acad. Sci. U.S.A. 114, 13453-13458.

Smith, M. P., and Wellbrock, C. (2016). Molecular Pathways: Maintaining MAPK Inhibitor Sensitivity by Targeting Nonmutational Tolerance. Clin. Cancer Res. Off. J. Am. Assoc. Cancer Res. 22, 5966-5970.

Steeg, P. S. (2016). Targeting metastasis. Nat. Rev. Cancer 16, 201-218.

Sun, M., Song, C.-X., Huang, H., Frankenberger, C. A., Sankarasharma, D., Gomes, S., Chen, P., Chen, J., Chada, K. K., He, C., et al. (2013). HMGA2/TET1/HOXA9 signaling pathway regulates breast cancer growth and metastasis. Proc. Natl. Acad. Sci. U.S.A. 110, 9920-9925.

Sun, M., Gomes, S., Chen, P., Frankenberger, C. A., Sankarasharma, D., Chung, C. H., Chada, K. K., and Rosner, M. R. (2014). RKIP and HMGA2 regulate breast tumor survival and metastasis through lysyl oxidase and syndecan-2. Oncogene 33, 3528-3537.

Tripathi, S., Pohl, M. O., Zhou, Y., Rodriguez-Frandsen, A., Wang, G., Stein, D. A., Moulton, H. M., DeJesus, P., Che, J., Mulder, L. C. F., et al. (2015). Meta- and Orthogonal Integration of Influenza "OMICs" Data Defines a Role for UBR4 in Virus Budding. Cell Host Microbe 18, 723-735.

Woods Ignatoski, K. M., Grewal, N. K., Markwart, S. M., Vellaichamy, A., Chinnaiyan, A. M., Yeung, K., Ray, M. E., and Keller, E. T. (2008). Loss of Raf Kinase Inhibitory Protein (RKIP) induces radioresistance in prostate cancer. Int. J. Radiat. Oncol. Biol. Phys. 72, 153-160.

Yesilkanal, A. E., and Rosner, M. R. (2018). Targeting Raf Kinase Inhibitory Protein Regulation and Function. Cancers 10.

Yeung, K., Seitz, T., Li, S., Janosch, P., McFerran, B., Kaiser, C., Fee, F., Katsanakis, K. D., Rose, D. W., Mischak, H., et al. (1999). Suppression of Raf-1 kinase activity and MAP kinase signalling by RKIP. Nature 401, 173-177.

Yeung, K. C., Rose, D. W., Dhillon, A. S., Yaros, D., Gustafsson, M., Chatterjee, D., McFerran, B., Wyche, J., Kolch, W., and Sedivy, J. M. (2001). Raf kinase inhibitor protein interacts with NF-kappaB-inducing kinase and TAK1 and inhibits NF-kappaB activation. Mol. Cell. Biol. 21, 7207-7217.

Yoeli-Lerner, M., Yiu, G. K., Rabinovitz, I., Erhardt, P., Jauliac, S., and Toker, A. (2005). Akt blocks breast cancer cell motility and invasion through the transcription factor NFAT. Mol. Cell 20, 539-550.

Yu, J.-R., Tai, Y., Jin, Y., Hammell, M. C., Wilkinson, J. E., Roe, J.-S., Vakoc, C. R., and Van Aelst, L. (2015). TGF-β/Smad signaling through DOCK4 facilitates lung adenocarcinoma metastasis. Genes Dev. 29, 250-261.

Yun, J., Frankenberger, C. A., Kuo, W.-L., Boelens, M. C., Eves, E. M., Cheng, N., Liang, H., Li, W.-H., Ishwaran, H., Minn, A. J., et al. (2011). Signalling pathway for RKIP and Let-7 regulates and predicts metastatic breast cancer. EMBO J. 30, 4500-4514.

Zhang, Y.-L., Wang, R.-C., Cheng, K., Ring, B. Z., and Su, L. (2017). Roles of Rap1 signaling in tumor cell migration and invasion. Cancer Biol. Med. 14, 90-99.

Zhao, M., Li, Z., and Qu, H. (2015). An evidence-based knowledgebase of metastasis suppressors to identify key pathways relevant to cancer metastasis. Sci. Rep. 5, 15478.

Zhou, B., Ritt, D. A., Morrison, D. K., Der, C. J., and Cox, A. D. (2016). Protein Kinase CK2α Maintains Extracellular Signal-regulated Kinase (ERK) Activity in a CK2α Kinase-independent Manner to Promote Resistance to Inhibitors of RAF and MEK but Not ERK in BRAF Mutant Melanoma. J. Biol. Chem. 291, 17804-17815.

Zhou, T., Raman, M., Gao, Y., Earnest, S., Chen, Z., Machius, M., Cobb, M. H., and Goldsmith, E. J. (2004). Crystal structure of the TAO2 kinase domain: activation and specificity of a Ste20p MAP3K. Struct. Lond. Engl. 1993 12, 1891-1900.

What is claimed is:

1. A method for treating a patient with cancer, comprising:
   (a) obtaining a cancer sample of a primary cancer from the patient;
   (b) measuring expression levels of ROCK2, DOCK4, ITGA1, APC, and RAPGEF2 in the cancer sample; and
   (c) administering a therapeutically effective amount of a composition comprising a MEK inhibitor, a p38MAPK inhibitor, a JNK inhibitor, and a MLK inhibitor to the patient when the expression levels of ROCK2, DOCK4, ITGA1, APC, and RAPGEF2 in the cancer sample are increased relative to the expression levels of the same genes in a control sample.

2. The method of claim 1, wherein the primary cancer is breast, pancreatic, ovarian, lung, head and neck, or colorectal cancer.

3. The method of claim 1 further comprising administering to the patient one or more of a chemotherapy, a radiation therapy, and an immunotherapy.

4. The method of claim 1, wherein the patient has a primary cancer with decreased RKIP (PEBP1) expression compared to the control sample.

5. The method of claim 1, wherein the primary cancer is triple-negative breast cancer (TNBC).

6. The method of claim 1, wherein the MEK inhibitor is trametinib, the p38MAPK inhibitor is SB203580, the JNK inhibitor is SP600125, and the MLK inhibitor is URMC-099.

7. The method of claim 6, wherein the composition comprises:
   (a) about 0.005 mg to about 200 mg of trametinib;
   (b) about 0.005 mg to about 200 mg SB203580;
   (c) about 0.005 mg to about 200 mg SP600125; and
   (d) about 0.005 mg to about 200 mg URMC-099.

* * * * *